US006235525B1

(12) United States Patent
van den Eynde et al.

(10) Patent No.: US 6,235,525 B1
(45) Date of Patent: May 22, 2001

(54) ISOLATED NUCLEIC ACID MOLECULES CODING FOR TUMOR REJECTION ANTIGEN PRECURSOR MAGE-3 AND USES THEREOF

(75) Inventors: Benoit van den Eynde; Pierre van der Bruggen; Thierry Boon-Falleur, all of Brussels (BE)

(73) Assignee: Ludwig Institute for Cancer Research, New York, NY (US)

( * ) Notice: Subject to any disclaimer, the term of this patent is extended or adjusted under 35 U.S.C. 154(b) by 0 days.

(21) Appl. No.: 08/037,230

(22) Filed: Mar. 26, 1993

Related U.S. Application Data

(63) Continuation-in-part of application No. PCT/US92/04354, filed on May 22, 1992, which is a continuation-in-part of application No. 07/807,043, filed on Dec. 12, 1991, now Pat. No. 5,342,774, which is a continuation-in-part of application No. 07/764,365, filed on Sep. 23, 1991, now abandoned, which is a continuation-in-part of application No. 07/728,838, filed on Jul. 9, 1991, now abandoned, which is a continuation-in-part of application No. 07/705,702, filed on May 23, 1991, now abandoned.

(51) Int. Cl.[7] .............................. C12N 5/10; C12N 15/12
(52) U.S. Cl. ....................... 435/325; 435/320.1; 435/334; 435/343.1; 435/343.2; 435/252.3; 536/23.5
(58) Field of Search .............................. 435/320.1, 252.3, 435/240.2, 325, 334, 343.1, 343.2, 69.3; 536/23.5

(56) References Cited

U.S. PATENT DOCUMENTS 5,342,774 * 8/1994 Boon et al. .

OTHER PUBLICATIONS

Zakut et al. Cancer Research 53:5–8 Jan. 1, 1993.*
Lazor et al. Mol. Cell Biology 8(3):1247–1252 1988.*
Burgess et al. J. Cell Biology 111:2129–37 1990.*
Herin et al., "Production of Stable Cytolytic T–Cell Clones Directed Against Autologous Human Melanoma", Ing. J. Cancer 39: 390–396 (1987).
Amichini et al., "Clonal analysis of the cytolytic T–cell response to human tumors", Immunol. Today 8(12): 385–389 (1987).
DePlaen et al., "Immunogenetic (tum⁻) variants of mouse tumor P815: Cloning of the gene of tum⁻antigen P91A and identification of the tum⁻mutation", Proc. Natl. Acad. Sci. USA 86: 2274–2278 (Apr. 1988).
Van den Eynde et al., "Presence on a Human Melanoma of Multiple Antigens Recognize by Autologous CTL".
Van Der Bruggen et al., "A Gene Encoding an Antigen Recognized by Cytolytic T Lymphocytes on a Human Melanoma", Science 254: 1643–1647 (Dec. 13, 1991).
Traversari et al., "A Nonapeptide Encoded by Human Gene Mage–1 is Recognized on HLA–A1 by Cytolytic T Lymphocytes Directed Against Tumor Antigen M2–E".
Brasseur et al., "Human gene Mage–1, which codes for a tumor rejection antigen, is expressed by some breast tumors", Int. J. Cancer 52: 839–841 (1992).
Traversari et al., Transfection and expression of a gene coding for a human Immunogenetic 35: 145–152 (1992).

\* cited by examiner

*Primary Examiner*—Anthony C. Caputa
(74) *Attorney, Agent, or Firm*—Felfe & Lynch

(57) ABSTRACT

The invention relates to nucleic acid molecules which code for the tumor rejection antigen precursor MAGE-3. Also disclosed are vectors, cell lines, and so forth, which utilize the nucleic acid molecule, and optionally, molecules coding for human leukocyte antigen HLA-A1. Uses of these materials in therapeutic and diagnostic contexts are also a part of the invention.

10 Claims, 18 Drawing Sheets

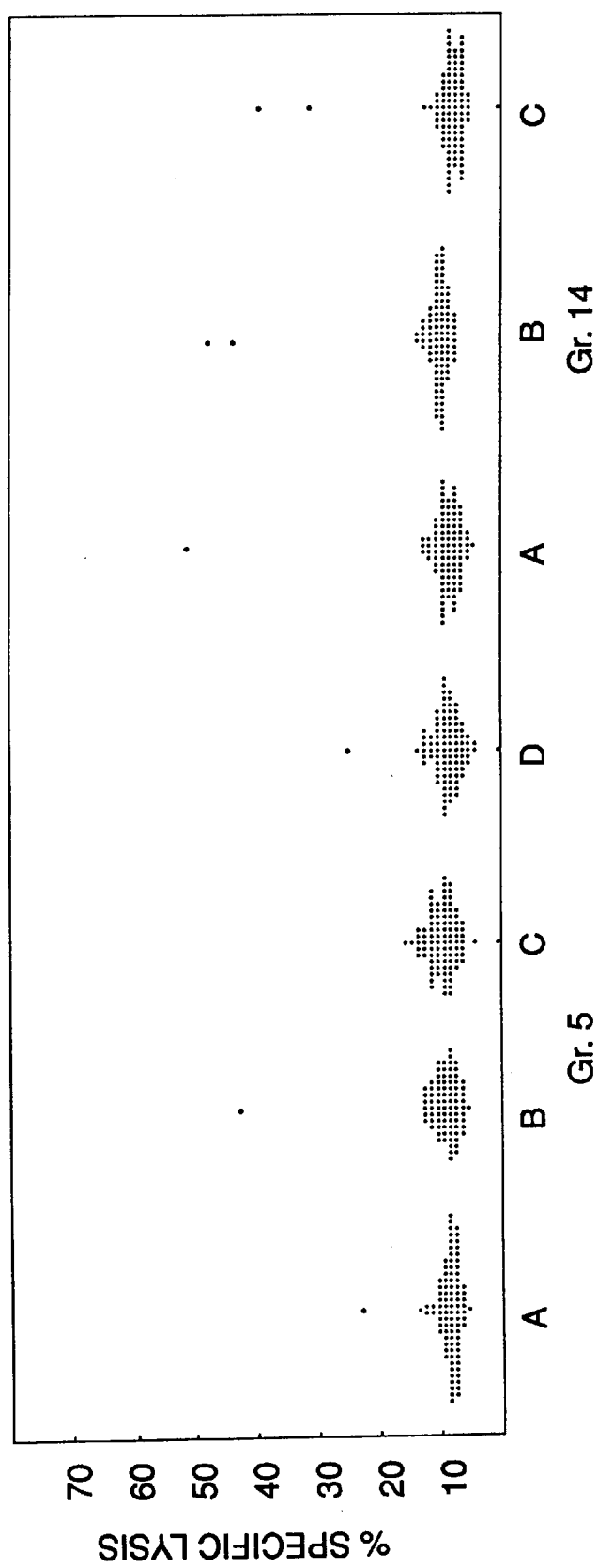

FIG. 9

```
MAGE-3 III    CCTCCCCAGAGTCCTCAGGGGAGCCTCCagCcTccCCACTACCATgAACTaCcCTCtctgGAGCCAATcCTaTGAGGaCTCCAGCAAcCaaGAAGAGGAGG
                                                                                                CHO-3
MAGE-2  II    CCTCCCCAcAGTCCTCAGGGGAGCCTCCagCTTctCgACTACCATCAACTaCACTCTttgGAGaCAATCCgaTGAGGGCTCCAGCAAcCaaGAAGAGGAGG
                                                                                                CHO-2
MAGE-1   I    CCTCCCCAGAGTCCTCAGGGGAGCCTCCgCCTTTCCCACTACCATCACTTCACTGACAGAGGCAACCCAGTGAGGGTTCCAGCAGCCGTGAAGAGGAGG
              225    CHO-8

III    GGCCAAGCACCTtcccTgaCC-TGGAGTCCgaGTTCCaAGCAGCAcTCAGTAGGAAGGTGGCcGAgTTGGTTcaTTTTCTGCTCCTCAAgTATCGAGCCA II    GGCCAAGaAtgTtTcccgaCCtTGGAGTCCGAGTTCCaAGCAGCAATCAGTAGAGAATCAGTGAgTTGGTcaTTTTCTGCTCCTCAAgTATCGAGCCA I    GGCCAAGCACCTCTTGTATCC-TGGAGTCCTTGTTCCGAGCAGTAATCACTAAGAAGGTGGCTGATTTGGTTTGTTTTCTGCTCCTCAAATATCGAGCCA
               325

III    GGGAGCCgGTCACAAAGGCAGAAATGCTGGgGAGTGTCgTCggAAATTggcAGTAtTtcTTTCCTGtGATCTTCAgCAAAGCTtCcagtTCCTTGCAGCT II    GGGAGCCgGTCACAAAGGCAGAAATGCTGGAGAGTGTCCTCAGAAATTgCcAGaCTTcCTTTCCgtGATCTTCAGCAAAGCCTCCGAGTaCTTGCAGCT I    GGGAGCCAGTCACAAAGGCAGAAATGCTGGAGAGTGTCATCAAAAATTACAAGCACTGTTTTCCTGAGATCTTCGGCAAAGCCTCTGAGTCCTTGCAGCT
               425     SEQ-4

III    GGTCTTTGGCATcGAgcTGAtGGAAGtgGACCCCATCGGCCACTtGTAcaTtCtTTGCCACCTGCCTgGGCCTCTCCTACgATGGCCTGCTGGGTGAcAAT

II    GGTCTTTGGCATcGAgGTGtGtGAAGTgtGCCCCATCAGCCACTtGTAcATCCTTGTCACCTGCCTgGGCCTCTCCTACgATGGCCTGCTGGGcGACAAT

I    GGTCTTTGGCATTGACGTGAAGGAAGCAGACCCCACCGGCCACTCCTATGTCCTTGTCACCTGCCTAGGTCTCTCCTATGATGGCCTGCTGGGTGATAAT
               525

III    CAGATCATGCCCAAGgCAGGCCTCCTGATAATCGTCCTGGCCATaAtCGCAAgaGAGGGCGaCTgTGCcCCTGAGGAGAaAAATCTGGGAGGAGCTGAGTG

II    CAGgTCATGCCCAAGaCAGGCCTCCTGATAATCGTC-TGGCCATaATCGCAATaGAGGGCGaCTgTGCcCCTGAGGAGAAAATCTGGGAGGAGCTGAGTa

I    CAGATCATGCCCAAGACACAGGCTTCCTGATAATTGTCCTGGTCATGATTGCAATGGAGGGCGGCCATGCTCCTGAGGAGAATCTGGGAGGAGCTGAGTG
               625                                                                                      CHO-9
```

FIG. 11A

| | | EXPRESSION OF MAGE GENE FAMILY | | | | RECOGNITION BY ANI-E CTL | | |
|---|---|---|---|---|---|---|---|---|
| | | Northern blot probed with cross-reactive MAGE-1 probe* | cDNA-PCR product probed with oligonucleotide specific for: | | | tested by: | | Expression of antigen MZ2-E after transfection** |
| | | | MAGE-1 | MAGE-2 | MAGE-3† | TNF release‡ | Lysis§ | |
| Cells of patient MZ2 | melanoma cell line MZ2-MEL.3.0 | + | +++ | +++ | +++ | + | + | |
| | tumor sample MZ2 (1982) | + | +++ | +++ | +++ | | | |
| | antigen-loss variant MZ2-MEL.2.2 | + | – | – | +++ | – | – | |
| | CTL clone MZ2-CTL.82/30 | – | – | – | – | | | |
| | PHA-activated blood lymphocytes | – | – | – | – | | | |
| Normal tissues | Liver | – | – | – | – | | | |
| | Muscle | – | – | – | – | | | |
| | Skin | – | – | – | – | | | |
| | Lung | – | – | – | – | | | |
| | Brain | – | – | – | – | | | |
| | Kidney | – | – | – | – | | | |
| Melanoma cell lines of HLA-A1 patients | LB34-MEL | + | ++ | +++ | +++ | + | +– | |
| | MI665/2-MEL | – | – | – | – | – | – | |
| | MI10221-MEL | + | +++ | ++ | +++ | – | – | |
| | MI13443-MEL | + | – | +++ | +++ | + | + | ++ |
| | SK33-MEL | + | – | +++ | +++ | – | – | – |
| | SK23-MEL | + | – | +++ | +++ | – | – | + |

\* Data obtained in the conditions of figure 5.
† Data obtained as described in figure 6.
‡ TNF release by CTL 82/30 after stimulation with the tumor cells as described in figure 1.
§ Lysis of 51 Cr labelled target by CTL 82/30 in the conditions of figure 1.
\*\* Cells transfected with the 2.4 kb fragment of gene MAGE-1 were tested for their ability to stimulate TNF release by CTL 82/30.

FIG. 11B

| | | Northern blot probed with cross-reactive MAGE-1 probe* | cDNA-PCR product probed with oligonucleotide specific for: | | | RECOGNITION BY ANTI-E CTL tested by: | | Expression of antigen MZ2-E after transfection** |
|---|---|---|---|---|---|---|---|---|
| | | | MAGE-1 | MAGE-2 | MAGE-3† | TNF release‡ | Lysis§ | |
| Melanoma cell lines of other patients | LB17-MEL | + | + | +++ | +++ | | | |
| | LB33-MEL | + | – | +++ | +++ | – | – | – |
| | LB4-MEL | – | – | – | – | – | – | – |
| | LB41-MEL | + | – | +++ | +++ | | | |
| | MI4024-MEL | – | +++ | +++ | +++ | – | – | |
| | SK29-MEL | + | – | +++ | – | – | – | |
| | MZ3-MEL | + | + | +++ | +++ | – | – | |
| | MZ5-MEL | + | – | +++ | +++ | – | – | |
| Melanoma tumor sample | BB5-MEL | + | +++ | ++ | +++ | – | – | |
| Other tumor cell lines | small cell lung cancer H209 | + | – | +++ | +++ | – | – | |
| | small cell lung cancer H345 | + | – | +++ | +++ | – | – | |
| | small cell lung cancer H510 | + | + | +++ | +++ | – | – | |
| | small cell lung cancer LB11 | + | – | +++ | +++ | – | – | |
| | bronchial squamous cell carcinoma LB37 | + | +++ | – | – | – | – | |
| | thyroid medullary carcinoma TT | + | – | +++ | +++ | – | – | |
| | colon carcinoma LB31 | + | – | +++ | +++ | – | – | |
| | colon carcinoma LS411 | – | – | – | – | – | | |
| Other tumor samples | chronic myeloid leukemia LLC5 | – | – | – | – | | | |
| | acute myeloid leukemia TA | – | – | – | – | | | |

\* Data obtained in the conditions of figure 5.
† Data obtained as described in figure 6.
‡ TNF release by CTL 82/30 after stimulation with the tumor cells as described in figure 1.
§ Lysis of 51 Cr labelled target by CTL 82/30 in the conditions of figure 1.
** Cells transfected with the 2.4 kb fragment of gene MAGE-1 were tested for their ability to stimulate TNF release by CTL 82/30

SEQUENCE LISTING (1) GENERAL INFORMATION:

(iii) NUMBER OF SEQUENCES: 30

(2) INFORMATION FOR SEQ ID NO: 1:

(i) SEQUENCE CHARACTERISTICS:
      (A) LENGTH: 462 base pairs
      (B) TYPE: nucleic acid
      (C) STRANDEDNESS: single
      (D) TOPOLOGY: linear (ii) MOLECULE TYPE: genomic DNA (xi) SEQUENCE DESCRIPTION: SEQ ID NO: 1:

```
ACCACAGGAG AATGAAAAGA ACCCGGGACT CCCAAAGACG CTAGATGTGT GAAGATCCTG      60

ATCACTCATT GGGTGTCTGA GTTCTGCGAT ATTCATCCCT CAGCCAATGA GCTTACTGTT     120

CTCGTGGGGG GTTTGTGAGC CTTGGGTAGG AAGTTTTGCA AGTTCCGCCT ACAGCTCTAG     180

CTTGTGAATT TGTACCCTTT CACGTAAAAA AGTAGTCCAG AGTTTACTAC ACCCTCCCTC     240

CCCCCTCCCA CCTCGTGCTG TGCTGAGTTT AGAAGTCTTC CTTATAGAAG TCTTCCGTAT     300

AGAACTCTTC CGGAGGAAGG AGGGAGGACC CCCCCCCTTT GCTCTCCCAG CATGCATTGT     360
```

```
GTCAACGCCA TTGCACTGAG CTGGTCGAAG AAGTAAGCCG CTAGCTTGCG ACTCTACTCT    420

TATCTTAACT TAGCTCGGCT TCCTGCTGGT ACCCTTTGTG CC                       462
```

(2) INFORMATION FOR SEQ ID NO: 2:

(i) SEQUENCE CHARACTERISTICS:
        (A) LENGTH: 675 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 2:

```
ATG TCT GAT AAC AAG AAA CCA GAC AAA GCC CAC AGT GGC TCA GGT GGT     48
Met Ser Asp Asn Lys Lys Pro Asp Lys Ala His Ser Gly Ser Gly Gly
              5                  10                  15

GAC GGT GAT GGG AAT AGG TGC AAT TTA TTG CAC CGG TAC TCC CTG GAA     96
Asp Gly Asp Gly Asn Arg Cys Asn Leu Leu His Arg Tyr Ser Leu Glu
             20                  25                  30

GAA ATT CTG CCT TAT CTA GGG TGG CTG GTC TTC GCT GTT GTC ACA ACA    144
Glu Ile Leu Pro Tyr Leu Gly Trp Leu Val Phe Ala Val Val Thr Thr
         35                  40                  45

AGT TTT CTG GCG CTC CAG ATG TTC ATA GAC GCC CTT TAT GAG GAG CAG    192
Ser Phe Leu Ala Leu Gln Met Phe Ile Asp Ala Leu Tyr Glu Glu Gln
     50                  55                  60

TAT GAA AGG GAT GTG GCC TGG ATA GCC AGG CAA AGC AAG CGC ATG TCC    240
Tyr Glu Arg Asp Val Ala Trp Ile Ala Arg Gln Ser Lys Arg Met Ser
 65                  70                  75                  80

TCT GTC GAT GAG GAT GAA GAC GAT GAG GAT GAT GAG GAT GAC TAC TAC    288
Ser Val Asp Glu Asp Glu Asp Asp Glu Asp Asp Glu Asp Asp Tyr Tyr
                 85                  90                  95

GAC GAC GAG GAC GAC GAC GAC GAT GCC TTC TAT GAT GAT GAG GAT GAT    336
Asp Asp Glu Asp Asp Asp Asp Asp Ala Phe Tyr Asp Asp Glu Asp Asp
            100                 105                 110

GAG GAA GAA GAA TTG GAG AAC CTG ATG GAT GAT GAA TCA GAA GAT GAG    384
Glu Glu Glu Glu Leu Glu Asn Leu Met Asp Asp Glu Ser Glu Asp Glu
        115                 120                 125

GCC GAA GAA GAG ATG AGC GTG GAA ATG GGT GCC GGA GCT GAG GAA ATG    432
Ala Glu Glu Glu Met Ser Val Glu Met Gly Ala Gly Ala Glu Glu Met
    130                 135                 140

GGT GCT GGC GCT AAC TGT GCC TGT GTT CCT GGC CAT CAT TTA AGG AAG    480
Gly Ala Gly Ala Asn Cys Ala Cys Val Pro Gly His His Leu Arg Lys
145                 150                 155                 160

AAT GAA GTG AAG TGT AGG ATG ATT TAT TTC TTC CAC GAC CCT AAT TTC    528
Asn Glu Val Lys Cys Arg Met Ile Tyr Phe Phe His Asp Pro Asn Phe
                165                 170                 175

CTG GTG TCT ATA CCA GTG AAC CCT AAG GAA CAA ATG GAG TGT AGG TGT    576
Leu Val Ser Ile Pro Val Asn Pro Lys Glu Gln Met Glu Cys Arg Cys
            180                 185                 190

GAA AAT GCT GAT GAA GAG GTT GCA ATG GAA GAG GAA GAA GAA GAG        624
Glu Asn Ala Asp Glu Glu Val Ala Met Glu Glu Glu Glu Glu Glu
        195                 200                 210

GAG GAG GAG GAG GAA GAG GAA ATG GGA AAC CCG GAT GGC TTC TCA CCT    672
Glu Glu Glu Glu Glu Glu Glu Met Gly Asn Pro Asp Gly Phe Ser Pro
220                 225                 230                 235

TAG                                                                675
```

(2) INFORMATION FOR SEQ ID NO: 3:

```
    (i) SEQUENCE CHARACTERISTICS:
        (A) LENGTH:  228 base pairs
        (B) TYPE:  nucleic acid
        (C) STRANDEDNESS:  single
        (D) TOPOLOGY:  linear (ii) MOLECULE TYPE:  genomic DNA (xi) SEQUENCE DESCRIPTION:  SEQ ID NO: 3:

GCATGCAGTT GCAAAGCCCA AAGAAAGAA ATGGACAGCG GAAGAAGTGG TTGTTTTTTT      60
TTCCCCTTCA TTAATTTTCT AGTTTTTAGT AATCCAGAAA ATTTGATTTT GTTCTAAAGT   120
TCATTATGCA AAGATGTCAC CAACAGACTT CTGACTGCAT GGTGAACTTT CATATGATAC   180
ATAGGATTAC ACTTGTACCT GTTAAAAATA AAGTTTGAC TTGCATAC                 228

(2) INFORMATION FOR SEQ ID NO: 4:

(i) SEQUENCE CHARACTERISTICS:
        (A) LENGTH:  1365 base pairs
        (B) TYPE:  nucleic acid
        (C) STRANDEDNESS:  single
        (D) TOPOLOGY:  linear (ii) MOLECULE TYPE:  genomic DNA (xi) SEQUENCE DESCRIPTION:  SEQ ID NO: 4:

ACCACAGGAG AATGAAAAGA ACCCGGGACT CCCAAAGACG CTAGATGTGT                50
GAAGATCCTG ATCACTCATT GGGTGTCTGA GTTCTGCGAT ATTCATCCCT              100
CAGCCAATGA GCTTACTGTT CTCGTGGGGG GTTTGTGAGC CTTGGGTAGG              150
AAGTTTTGCA AGTTCCGCCT ACAGCTCTAG CTTGTGAATT TGTACCCTTT              200
CACGTAAAAA AGTAGTCCAG AGTTTACTAC ACCCTCCCTC CCCCCTCCCA              250
CCTCGTGCTG TGCTGAGTTT AGAAGTCTTC CTTATAGAAG TCTTCCGTAT              300
AGAACTCTTC CGGAGGAAGG AGGGAGGACC CCCCCCCTTT GCTCTCCCAG              350
CATGCATTGT GTCAACGCCA TTGCACTGAG CTGGTCGAAG AAGTAAGCCG              400
CTAGCTTGCG ACTCTACTCT TATCTTAACT TAGCTCGGCT TCCTGCTGGT              450
ACCCTTTGTG CC                                                      462
ATG TCT GAT AAC AAG AAA CCA GAC AAA GCC CAC AGT GGC TCA             504
GGT GGT GAC GGT GAT GGG AAT AGG TGC AAT TTA TTG CAC CGG             546
TAC TCC CTG GAA GAA ATT CTG CCT TAT CTA GGG TGG CTG GTC             588
TTC GCT GTT GTC ACA ACA AGT TTT CTG GCG CTC CAG ATG TTC             630
ATA GAC GCC CTT TAT GAG GAG CAG TAT GAA AGG GAT GTG GCC             672
TGG ATA GCC AGG CAA AGC AAG CGC ATG TCC TCT GTC GAT GAG             714
GAT GAA GAC GAT GAG GAT GAT GAG GAT GAC TAC TAC GAC GAC             756
GAG GAC GAC GAC GAC GAT GCC TTC TAT GAT GAT GAG GAT GAT             798
GAG GAA GAA GAA TTG GAG AAC CTG ATG GAT GAT GAA TCA GAA             840
GAT GAG GCC GAA GAA GAG ATG AGC GTG GAA ATG GGT GCC GGA             882
GCT GAG GAA ATG GGT GCT GGC GCT AAC TGT GCC TGT GTT CCT             924
GGC CAT CAT TTA AGG AAG AAT GAA GTG AAG TGT AGG ATG ATT             966
TAT TTC TTC CAC GAC CCT AAT TTC CTG GTG TCT ATA CCA GTG            1008
AAC CCT AAG GAA CAA ATG GAG TGT AGG TGT GAA AAT GCT GAT            1050
```

```
GAA GAG GTT GCA ATG GAA GAG GAA GAA GAA GAA GAG GAG GAG                1092

GAG GAG GAA GAG GAA ATG GGA AAC CCG GAT GGC TTC TCA CCT                1134

TAG                                                                    1137

GCATGCAGTT GCAAAGCCCA GAAGAAAGAA ATGGACAGCG GAAGAAGTGG                 1187

TTGTTTTTTT TTCCCCTTCA TTAATTTTCT AGTTTTTAGT AATCCAGAAA                 1237

ATTTGATTTT GTTCTAAAGT TCATTATGCA AAGATGTCAC CAACAGACTT                 1287

CTGACTGCAT GGTGAACTTT CATATGATAC ATAGGATTAC ACTTGTACCT                 1337

GTTAAAAATA AAGTTTGAC TTGCATAC                                          1365

(2) INFORMATION FOR SEQ ID NO: 5:

(i) SEQUENCE CHARACTERISTICS:
        (A) LENGTH: 4698 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 5:

ACCACAGGAG AATGAAAAGA ACCCGGGACT CCCAAAGACG CTAGATGTGT                   50

GAAGATCCTG ATCACTCATT GGGTGTCTGA GTTCTGCGAT ATTCATCCCT                  100

CAGCCAATGA GCTTACTGTT CTCGTGGGGG GTTTGTGAGC CTTGGGTAGG                  150

AAGTTTTGCA AGTTCCGCCT ACAGCTCTAG CTTGTGAATT TGTACCCTTT                  200

CACGTAAAAA AGTAGTCCAG AGTTTACTAC ACCCTCCCTC CCCCCTCCCA                  250

CCTCGTGCTG TGCTGAGTTT AGAAGTCTTC CTTATAGAAG TCTTCCGTAT                  300

AGAACTCTTC CGGAGGAAGG AGGGAGGACC CCCCCCCTTT GCTCTCCCAG                  350

CATGCATTGT GTCAACGCCA TTGCACTGAG CTGGTCGAAG AAGTAAGCCG                  400

CTAGCTTGCG ACTCTACTCT TATCTTAACT TAGCTCGGCT TCCTGCTGGT                  450

ACCCTTTGTG CC                                                          462

ATG TCT GAT AAC AAG AAA CCA GAC AAA GCC CAC AGT GGC TCA                 504

GGT GGT GAC GGT GAT GGG AAT AGG TGC AAT TTA TTG CAC CGG                 546

TAC TCC CTG GAA GAA ATT CTG CCT TAT CTA GGG TGG CTG GTC                 588

TTC GCT GTT GTC ACA ACA AGT TTT CTG GCG CTC CAG ATG TTC                 630

ATA GAC GCC CTT TAT GAG GAG CAG TAT GAA AGG GAT GTG GCC                 672

TGG ATA GCC AGG CAA AGC AAG CGC ATG TCC TCT GTC GAT GAG                 714

GAT GAA GAC GAT GAG GAT GAT GAG GAT GAC TAC TAC GAC GAC                 756

GAG GAC GAC GAC GAC GAT GCC TTC TAT GAT GAT GAG GAT GAT                 798

GAG GAA GAA GAA TTG GAG AAC CTG ATG GAT GAT GAA TCA GAA                 840

GAT GAG GCC GAA GAA GAG ATG AGC GTG GAA ATG GGT GCC GGA                 882

GCT GAG GAA ATG GGT GCT GGC GCT AAC TGT GCC T                          916

GTGAGTAACC CGTGGTCTTT ACTCTAGATT CAGGTGGGGT GCATTCTTTA                  966

CTCTTGCCCA CATCTGTAGT AAAGACCACA TTTTGGTTGG GGGTCATTGC                 1016

TGGAGCCATT CCTGGCTCTC CTGTCCACGC CTATCCCCGC TCCTCCCATC                 1066

CCCCACTCCT TGCTCCGCTC TCTTTCCTTT TCCCACCTTG CCTCTGGAGC                 1116
```

| | |
|---|---|
| TTCAGTCCAT CCTGCTCTGC TCCCTTTCCC CTTTGCTCTC CTTGCTCCCC | 1166 |
| TCCCCCTCGG CTCAACTTTT CGTGCCTTCT GCTCTCTGAT CCCCACCCTC | 1216 |
| TTCAGGCTTC CCCATTTGCT CCTCTCCCGA AACCCTCCCC TTCCTGTTCC | 1266 |
| CCTTTTCGCG CCTTTTCTTT CCTGCTCCCC TCCCCCTCCC TATTTACCTT | 1316 |
| TCACCAGCTT TGCTCTCCCT GCTCCCCTCC CCCTTTTGCA CCTTTTCTTT | 1366 |
| TCCTGCTCCC CTCCCCCTCC CCTCCCTGTT TACCCTTCAC CGCTTTTCCT | 1416 |
| CTACCTGCTT CCCTCCCCCT TGCTGCTCCC TCCCTATTTG CATTTTCGGG | 1466 |
| TGCTCCTCCC TCCCCCTCCC CCTCCCTCCC TATTTGCATT TTCGGGTGCT | 1516 |
| CCTCCCTCCC CCTCCCCAGG CCTTTTTTTT TTTTTTTTT TTTTTTTTT | 1566 |
| TTGGTTTTTC GAGACAGGGT TTCTCTTTGT ATCCCTGGCT GTCCTGGCAC | 1616 |
| TCACTCTGTA GACCAGGCTG GCCTCAAACT CAGAAATCTG CCTGCCTCTG | 1666 |
| CCTCCCAAAT GCTGGGATTA AAGGCTTGCA CCAGGACTGC CCCAGTGCAG | 1716 |
| GCCTTTCTTT TTTCTCCTCT CTGGTCTCCC TAATCCCTTT TCTGCATGTT | 1766 |
| AACTCCCCTT TTGGCACCTT TCCTTTACAG GACCCCCTCC CCCTCCCTGT | 1816 |
| TTCCCTTCCG GCACCCTTCC TAGCCCTGCT CTGTTCCCTC TCCCTGCTCC | 1866 |
| CCTCCCCCTC TTTGCTCGAC TTTTAGCAGC CTTACCTCTC CCTGCTTTCT | 1916 |
| GCCCCGTTCC CCTTTTTTGT GCCTTTCCTC CTGGCTCCCC TCCACCTTCC | 1966 |
| AGCTCACCTT TTTGTTTGTT TGGTTGTTTG GTTGTTTGGT TTGCTTTTTT | 2016 |
| TTTTTTTTTT GCACCTTGTT TTCCAAGATC CCCCTCCCCC TCCGGCTTCC | 2066 |
| CCTCTGTGTG CCTTTCCTGT TCCCTCCCCC TCGCTGGCTC CCCCTCCCTT | 2116 |
| TCTGCCTTTC CTGTCCCTGC TCCCTTCTCT GCTAACCTTT TAATGCCTTT | 2166 |
| CTTTTCTAGA CTCCCCCCTC CAGGCTTGCT GTTTGCTTCT GTGCACTTTT | 2216 |
| CCTGACCCTG CTCCCCTTCC CCTCCCAGCT CCCCCCTCTT TTCCCACCTC | 2266 |
| CCTTTCTCCA GCCTGTCACC CCTCCTTCTC TCCTCTCTGT TTCTCCCACT | 2316 |
| TCCTGCTTCC TTTACCCCTT CCCTCTCCCT ACTCTCCTCC CTGCCTGCTG | 2366 |
| GACTTCCTCT CCAGCCGCCC AGTTCCCTGC AGTCCTGGAG TCTTTCCTGC | 2416 |
| CTCTCTGTCC ATCACTTCCC CCTAGTTTCA CTTCCCTTTC ACTCTCCCCT | 2466 |
| ATGTGTCTCT CTTCCTATCT ATCCCTTCCT TTCTGTCCCC TCTCCTCTGT | 2516 |
| CCATCACCTC TCTCCTCCCT TCCCTTTCCT CTCTCTTCCA TTTTCTTCCA | 2566 |
| CCTGCTTCTT TACCCTGCCT CTCCCATTGC CCTCTTACCT TTATGCCCAT | 2616 |
| TCCATGTCCC CTCTCAATTC CCTGTCCCAT TGTGCTCCCT CACATCTTCC | 2666 |
| ATTTCCCTCT TTCTCCCTTA GCCTCTTCTT CCTCTTCTCT TGTATCTCCC | 2716 |
| TTCCCTTTGC TTCTCCCTCC TCCTTTCCCC TTCCCCTATG CCCTCTACTC | 2766 |
| TACTTGATCT TCTCTCCTCT CCACATACCC TTTTTCCTTT CCACCCTGCC | 2816 |
| CTTTGTCCCC AGACCCTACA GTATCCTGTG CACAGGAAGT GGGAGGTGCC | 2866 |
| ATCAACAACA AGGAGGCAAG AAACAGAGCA AAATCCCAAA ATCAGCAGGA | 2916 |
| AAGGCTGGAT GAAAATAAGG CCAGGTTCTG AGGACAGCTG GAATCTAGCC | 2966 |
| AAGTGGCTCC TATAACCCTA AGTACCAAGG GAGAAAGTGA TGGTGAAGTT | 3016 |
| CTTGATCCTT GCTGCTTCTT TTACATATGT TGGCACATCT TTCTCAAATG | 3066 |
| CAGGCCATGC TCCATGCTTG GCGCTTGCTC AGCGTGGTTA AGTAATGGGA | 3116 |

```
GAATCTGAAA ACTAGGGGCC AGTGGTTTGT TTTGGGGACA AATTAGCACG        3166

TAGTGATATT TCCCCCTAAA AATTATAACA AACAGATTCA TGATTTGAGA        3216

TCCTTCTACA GGTGAGAAGT GGAAAAATTG TCACTATGAA GTTCTTTTTA        3266

GGCTAAAGAT ACTTGGAACC ATAGAAGCGT TGTTAAAATA CTGCTTTCTT        3316

TTGCTAAAAT ATTCTTTCTC ACATATTCAT ATTCTCCAG                    3355

GT GTT CCT GGC CAT CAT TTA AGG AAG AAT GAA GTG AAG TGT        3396

AGG ATG ATT TAT TTC TTC CAC GAC CCT AAT TTC CTG GTG TCT       3438

ATA CCA GTG AAC CCT AAG GAA CAA ATG GAG TGT AGG TGT GAA       3480

AAT GCT GAT GAA GAG GTT GCA ATG GAA GAG GAA GAA GAA GAA       3522

GAG GAG GAG GAG GAG GAA GAG GAA ATG GGA AAC CCG GAT GGC       3564

TTC TCA CCT TAG                                               3576

GCATGCAGGT ACTGGCTTCA CTAACCAACC ATTCCTAACA TATGCCTGTA        3626

GCTAAGAGCA TCTTTTTAAA AAATATTATT GGTAAACTAA ACAATTGTTA        3676

TCTTTTTACA TTAATAAGTA TTAAATTAAT CCAGTATACA GTTTTAAGAA        3726

CCCTAAGTTA AACAGAAGTC AATGATGTCT AGATGCCTGT TCTTTAGATT        3776

GTAGTGAGAC TACTTACTAC AGATGAGAAG TTGTTAGACT CGGGAGTAGA        3826

GACCAGTAAA AGATCATGCA GTGAAATGTG GCCATGAAAA TCGCATATTG        3876

TTCTTATAGT ACCTTTGAGA CAGCTGATAA CAGCTGACAA AAATAAGTGT        3926

TTCAAGAAAG ATCACACGCC ATGGTTCACA TGCAAATTAT TATTTTGTCG        3976

TTCTGATTTT TTTCATTTCT AGACCTGTGG TTTTAAAGAG ATGAAAATCT        4026

CTTAAAATTT CCTTCATCTT TAATTTTCCT TAACTTTAGT TTTTTTCACT        4076

TAGAATTCAA TTCAAATTCT TAATTCAATC TTAATTTTTA GATTTCTTAA        4126

AATGTTTTTT AAAAAAAATG CAAATCTCAT TTTTAAGAGA TGAAAGCAGA        4176

GTAACTGGGG GGCTTAGGGA ATCTGTAGGG TTGCGGTATA GCAATAGGGA        4226

GTTCTGGTCT CTGAGAAGCA GTCAGAGAGA ATGGAAAACC AGGCCCTTGC        4276

CAGTAGGTTA GTGAGGTTGA TATGATCAGA TTATGGACAC TCTCCAAATC        4326

ATAAATACTC TAACAGCTAA GGATCTCTGA GGGAAACACA ACAGGGAAAT        4376

ATTTTAGTTT CTCCTTGAGA AACAATGACA AGACATAAAA TTGGCAAGAA        4426

AGTCAGGAGT GTATTCTAAT AAGTGTTGCT TATCTCTTAT TTTCTTCTAC        4476

AGTTGCAAAG CCCAGAAGAA AGAAATGGAC AGCGGAAGAA GTGGTTGTTT        4526

TTTTTTCCCC TTCATTAATT TTCTAGTTTT TAGTAATCCA GAAAATTTGA        4576

TTTTGTTCTA AAGTTCATTA TGCAAAGATG TCACCAACAG ACTTCTGACT        4626

GCATGGTGAA CTTTCATATG ATACATAGGA TTACACTTGT ACCTGTTAAA        4676

AATAAAAGTT TGACTTGCAT AC                                     4698
```

(2) INFORMATION FOR SEQ ID NO: 6:

(i) SEQUENCE CHARACTERISTICS:
        (A) LENGTH: 9 amino acids
        (B) TYPE: amino acid
        (D) TOPOLOGY: linear (ii) MOLECULE TYPE: protein (xi) SEQUENCE DESCRIPTION: SEQ ID NO: 6:

Leu Pro Tyr Leu Gly Trp Leu Val Phe
                5

(2) INFORMATION FOR SEQ ID NO: 7:

(i) SEQUENCE CHARACTERISTICS:
        (A) LENGTH: 2419 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 7:

```
GGATCCAGGC CCTGCCAGGA AAAATATAAG GGCCCTGCGT GAGAACAGAG           50

GGGGTCATCC ACTGCATGAG AGTGGGGATG TCACAGAGTC CAGCCCACCC          100

TCCTGGTAGC ACTGAGAAGC CAGGGCTGTG CTTGCGGTCT GCACCCTGAG          150

GGCCCGTGGA TTCCTCTTCC TGGAGCTCCA GGAACCAGGC AGTGAGGCCT          200

TGGTCTGAGA CAGTATCCTC AGGTCACAGA GCAGAGGATG CACAGGGTGT          250

GCCAGCAGTG AATGTTTGCC CTGAATGCAC ACCAAGGGCC CCACCTGCCA          300

CAGGACACAT AGGACTCCAC AGAGTCTGGC CTCACCTCCC TACTGTCAGT          350

CCTGTAGAAT CGACCTCTGC TGGCCGGCTG TACCCTGAGT ACCCTCTCAC          400

TTCCTCCTTC AGGTTTTCAG GGGACAGGCC AACCCAGAGG ACAGGATTCC          450

CTGGAGGCCA CAGAGGAGCA CCAAGGAGAA GATCTGTAAG TAGGCCTTTG          500

TTAGAGTCTC CAAGGTTCAG TTCTCAGCTG AGGCCTCTCA CACACTCCCT          550

CTCTCCCCAG GCCTGTGGGT CTTCATTGCC CAGCTCCTGC CCACACTCCT          600

GCCTGCTGCC CTGACGAGAG TCATCATGTC TCTTGAGCAG AGGAGTCTGC          650

ACTGCAAGCC TGAGGAAGCC CTTGAGGCCC AACAAGAGGC CCTGGGCCTG          700

GTGTGTGTGC AGGCTGCCAC CTCCTCCTCC TCTCCTCTGG TCCTGGGCAC          750

CCTGGAGGAG GTGCCCACTG CTGGGTCAAC AGATCCTCCC CAGAGTCCTC          800

AGGGAGCCTC CGCCTTTCCC ACTACCATCA ACTTCACTCG ACAGAGGCAA          850

CCCAGTGAGG GTTCCAGCAG CCGTGAAGAG GAGGGGCCAA GCACCTCTTG          900

TATCCTGGAG TCCTTGTTCC GAGCAGTAAT CACTAAGAAG GTGGCTGATT          950

TGGTTGGTTT TCTGCTCCTC AAATATCGAG CCAGGGAGCC AGTCACAAAG         1000

GCAGAAATGC TGGAGAGTGT CATCAAAAAT TACAAGCACT GTTTTCCTGA         1050

GATCTTCGGC AAAGCCTCTG AGTCCTTGCA GCTGGTCTTT GGCATTGACG         1100

TGAAGGAAGC AGACCCCACC GGCCACTCCT ATGTCCTTGT CACCTGCCTA         1150

GGTCTCTCCT ATGATGGCCT GCTGGGTGAT AATCAGATCA TGCCCAAGAC         1200

AGGCTTCCTG ATAATTGTCC TGGTCATGAT TGCAATGGAG GGCGGCCATG         1250

CTCCTGAGGA GGAAATCTGG GAGGAGCTGA GTGTGATGGA GGTGTATGAT         1300

GGGAGGGAGC ACAGTGCCTA TGGGGAGCCC AGGAAGCTGC TCACCCAAGA         1350

TTTGGTGCAG GAAAAGTACC TGGAGTACGG CAGGTGCCGG ACAGTGATCC         1400

CGCACGCTAT GAGTTCCTGT GGGGTCCAAG GGCCCTCGCT GAAACCAGCT         1450

ATGTGAAAGT CCTTGAGTAT GTGATCAAGG TCAGTGCAAG AGTTCGCTTT         1500

TTCTTCCCAT CCCTGCGTGA AGCAGCTTTG AGAGAGGAGG AAGAGGGAGT         1550
```

-continued

```
CTGAGCATGA GTTGCAGCCA AGGCCAGTGG GAGGGGGACT GGGCCAGTGC    1600

ACCTTCCAGG GCCGCGTCCA GCAGCTTCCC CTGCCTCGTG TGACATGAGG    1650

CCCATTCTTC ACTCTGAAGA GAGCGGTCAG TGTTCTCAGT AGTAGGTTTC    1700

TGTTCTATTG GGTGACTTGG AGATTTATCT TTGTTCTCTT TTGGAATTGT    1750

TCAAATGTTT TTTTTTAAGG GATGGTTGAA TGAACTTCAG CATCCAAGTT    1800

TATGAATGAC AGCAGTCACA CAGTTCTGTG TATATAGTTT AAGGGTAAGA    1850

GTCTTGTGTT TTATTCAGAT TGGGAAATCC ATTCTATTTT GTGAATTGGG    1900

ATAATAACAG CAGTGGAATA AGTACTTAGA AATGTGAAAA ATGAGCAGTA    1950

AAATAGATGA GATAAAGAAC TAAAGAAATT AAGAGATAGT CAATTCTTGC    2000

CTTATACCTC AGTCTATTCT GTAAAATTTT TAAAGATATA TGCATACCTG    2050

GATTTCCTTG GCTTCTTTGA GAATGTAAGA GAAATTAAAT CTGAATAAAG    2100

AATTCTTCCT GTTCACTGGC TCTTTTCTTC TCCATGCACT GAGCATCTGC    2150

TTTTTGGAAG GCCCTGGGTT AGTAGTGGAG ATGCTAAGGT AAGCCAGACT    2200

CATACCCACC CATAGGGTCG TAGAGTCTAG GAGCTGCAGT CACGTAATCG    2250

AGGTGGCAAG ATGTCCTCTA AAGATGTAGG GAAAAGTGAG AGAGGGGTGA    2300

GGGTGTGGGG CTCCGGGTGA GAGTGGTGGA GTGTCAATGC CCTGAGCTGG    2350

GGCATTTTGG GCTTTGGGAA ACTGCAGTTC CTTCTGGGGG AGCTGATTGT    2400

AATGATCTTG GGTGGATCC                                      2419
```

(2) INFORMATION FOR SEQ ID NO: 8:

(i) SEQUENCE CHARACTERISTICS:
        (A) LENGTH: 5674 base pairs
        (B) TYPE: nucleic acid
        (C) STRANDEDNESS: single
        (D) TOPOLOGY: linear (ii) MOLECULE TYPE: genomic DNA (ix) FEATURE:
        (A) NAME/KEY: MAGE-1 gene (xi) SEQUENCE DESCRIPTION: SEQ ID NO: 8:

```
CCCGGGGCAC CACTGGCATC CCTCCCCCTA CCACCCCCAA TCCCTCCCTT      50

TACGCCACCC ATCCAAACAT CTTCACGCTC ACCCCCAGCC CAAGCCAGGC     100

AGAATCCGGT TCCACCCCTG CTCTCAACCC AGGGAAGCCC AGGTGCCCAG     150

ATGTGACGCC ACTGACTTGA GCATTAGTGG TTAGAGAGAA GCGAGGTTTT     200

CGGTCTGAGG GGCGGCTTGA GATCGGTGGA GGGAAGCGGG CCCAGCTCTG     250

TAAGGAGGCA AGGTGACATG CTGAGGGAGG ACTGAGGACC CACTTACCCC     300

AGATAGAGGA CCCAAATAA TCCCTTCATG CCAGTCCTGG ACCATCTGGT     350

GGTGGACTTC TCAGGCTGGG CCACCCCCAG CCCCCTTGCT GCTTAAACCA     400

CTGGGGACTC GAAGTCAGAG CTCCGTGTGA TCAGGGAAGG GCTGCTTAGG     450

AGAGGGCAGC GTCCAGGCTC TGCCAGACAT CATGCTCAGG ATTCTCAAGG     500

AGGGCTGAGG GTCCCTAAGA CCCCACTCCC GTGACCCAAC CCCCACTCCA     550

ATGCTCACTC CCGTGACCCA ACCCCCTCTT CATTGTCATT CCAACCCCCA     600

CCCCACATCC CCCACCCCAT CCCTCAACCC TGATGCCCAT CCGCCCAGCC     650
```

```
ATTCCACCCT CACCCCCACC CCCACCCCCA CGCCCACTCC CACCCCCACC         700

CAGGCAGGAT CCGGTTCCCG CCAGGAAACA TCCGGGTGCC CGGATGTGAC         750

GCCACTGACT TGCGCATTGT GGGGCAGAGA GAAGCGAGGT TTCCATTCTG         800

AGGGACGGCG TAGAGTTCGG CCGAAGGAAC CTGACCCAGG CTCTGTGAGG         850

AGGCAAGGTG AGAGGCTGAG GGAGGACTGA GGACCCCGCC ACTCCAAATA         900

GAGAGCCCCA AATATTCCAG CCCCGCCCTT GCTGCCAGCC CTGGCCCACC         950

CGCGGGAAGA CGTCTCAGCC TGGGCTGCCC CCAGACCCCT GCTCCAAAAG        1000

CCTTGAGAGA CACCAGGTTC TTCTCCCCAA GCTCTGGAAT CAGAGGTTGC        1050

TGTGACCAGG GCAGGACTGG TTAGGAGAGG GCAGGGCACA GGCTCTGCCA        1100

GGCATCAAGA TCAGCACCCA AGAGGGAGGG CTGTGGGCCC CCAAGACTGC        1150

ACTCCAATCC CCACTCCCAC CCCATTCGCA TTCCCATTCC CCACCCAACC        1200

CCCATCTCCT CAGCTACACC TCCACCCCCA TCCCTACTCC TACTCCGTCA        1250

CCTGACCACC ACCCTCCAGC CCCAGCACCA GCCCCAACCC TTCTGCCACC        1300

TCACCCTCAC TGCCCCCAAC CCCACCCTCA TCTCTCTCAT GTGCCCCACT        1350

CCCATCGCCT CCCCCATTCT GGCAGAATCC GGTTTGCCCC TGCTCTCAAC        1400

CCAGGGAAGC CCTGGTAGGC CCGATGTGAA ACCACTGACT TGAACCTCAC        1450

AGATCTGAGA GAAGCCAGGT TCATTTAATG GTTCTGAGGG GCGGCTTGAG        1500

ATCCACTGAG GGGAGTGGTT TTAGGCTCTG TGAGGAGGCA AGGTGAGATG        1550

CTGAGGGAGG ACTGAGGAGG CACACACCCC AGGTAGATGG CCCCAAAATG        1600

ATCCAGTACC ACCCCTGCTG CCAGCCCTGG ACCACCCGGC CAGGACAGAT        1650

GTCTCAGCTG GACCACCCCC CGTCCCGTCC CACTGCCACT TAACCCACAG        1700

GGCAATCTGT AGTCATAGCT TATGTGACCG GGGCAGGGTT GGTCAGGAGA        1750

GGCAGGGCCC AGGCATCAAG GTCCAGCATC CGCCCGGCAT TAGGGTCAGG        1800

ACCCTGGGAG GGAACTGAGG GTTCCCCACC CACACCTGTC TCCTCATCTC        1850

CACCGCCACC CCACTCACAT TCCCATACCT ACCCCCTACC CCCAACCTCA        1900

TCTTGTCAGA ATCCCTGCTG TCAACCCACG GAAGCCACGG GAATGGCGGC        1950

CAGGCACTCG GATCTTGACG TCCCCATCCA GGGTCTGATG GAGGGAAGGG        2000

GCTTGAACAG GGCCTCAGGG GAGCAGAGGG AGGGCCCTAC TGCGAGATGA        2050

GGGAGGCCTC AGAGGACCCA GCACCCTAGG ACACCGCACC CCTGTCTGAG        2100

ACTGAGGCTG CCACTTCTGG CCTCAAGAAT CAGAACGATG GGGACTCAGA        2150

TTGCATGGGG GTGGGACCCA GGCCTGCAAG GCTTACGCGG AGGAAGAGGA        2200

GGGAGGACTC AGGGGACCTT GGAATCCAGA TCAGTGTGGA CCTCGGCCCT        2250

GAGAGGTCCA GGGCACGGTG GCCACATATG GCCCATATTT CCTGCATCTT        2300

TGAGGTGACA GGACAGAGCT GTGGTCTGAG AAGTGGGGCC TCAGGTCAAC        2350

AGAGGGAGGA GTTCCAGGAT CCATATGGCC CAAGATGTGC CCCCTTCATG        2400

AGGACTGGGG ATATCCCCGG CTCAGAAAGA AGGGACTCCA CACAGTCTGG        2450

CTGTCCCCTT TTAGTAGCTC TAGGGGGACC AGATCAGGGA TGGCGGTATG        2500

TTCCATTCTC ACTTGTACCA CAGGCAGGAA GTTGGGGGGC CCTCAGGGAG        2550

ATGGGGTCTT GGGGTAAAGG GGGGATGTCT ACTCATGTCA GGGAATTGGG        2600

GGTTGAGGAA GCACAGGCGC TGGCAGGAAT AAAGATGAGT GAGACAGACA        2650
```

-continued

```
AGGCTATTGG AATCCACACC CCAGAACCAA AGGGGTCAGC CCTGGACACC        2700

TCACCCAGGA TGTGGCTTCT TTTTCACTCC TGTTTCCAGA TCTGGGGCAG        2750

GTGAGGACCT CATTCTCAGA GGGTGACTCA GGTCAACGTA GGGACCCCCA        2800

TCTGGTCTAA AGACAGAGCG GTCCCAGGAT CTGCCATGCG TTCGGGTGAG        2850

GAACATGAGG GAGGACTGAG GGTACCCCAG GACCAGAACA CTGAGGGAGA        2900

CTGCACAGAA ATCAGCCCTG CCCCTGCTGT CACCCCAGAG AGCATGGGCT        2950

GGGCCGTCTG CCGAGGTCCT TCCGTTATCC TGGGATCATT GATGTCAGGG        3000

ACGGGGAGGC CTTGGTCTGA GAAGGCTGCG CTCAGGTCAG TAGAGGGAGC        3050

GTCCCAGGCC CTGCCAGGAG TCAAGGTGAG GACCAAGCGG GCACCTCACC        3100

CAGGACACAT TAATTCCAAT GAATTTTGAT ATCTCTTGCT GCCCTTCCCC        3150

AAGGACCTAG GCACGTGTGG CCAGATGTTT GTCCCCTCCT GTCCTTCCAT        3200

TCCTTATCAT GGATGTGAAC TCTTGATTTG GATTTCTCAG ACCAGCAAAA        3250

GGGCAGGATC CAGGCCCTGC CAGGAAAAAT ATAAGGGCCC TGCGTGAGAA        3300

CAGAGGGGGT CATCCACTGC ATGAGAGTGG GGATGTCACA GAGTCCAGCC        3350

CACCCTCCTG GTAGCACTGA GAAGCCAGGG CTGTGCTTGC GGTCTGCACC        3400

CTGAGGGCCC GTGGATTCCT CTTCCTGGAG CTCCAGGAAC CAGGCAGTGA        3450

GGCCTTGGTC TGAGACAGTA TCCTCAGGTC ACAGAGCAGA GGATGCACAG        3500

GGTGTGCCAG CAGTGAATGT TTGCCCTGAA TGCACACCAA GGGCCCCACC        3550

TGCCACAGGA CACATAGGAC TCCACAGAGT CTGGCCTCAC CTCCCTACTG        3600

TCAGTCCTGT AGAATCGACC TCTGCTGGCC GGCTGTACCC TGAGTACCCT        3650

CTCACTTCCT CCTTCAGGTT TTCAGGGGAC AGGCCAACCC AGAGGACAGG        3700

ATTCCCTGGA GGCCACAGAG GAGCACCAAG GAGAAGATCT GTAAGTAGGC        3750

CTTTGTTAGA GTCTCCAAGG TTCAGTTCTC AGCTGAGGCC TCTCACACAC        3800

TCCCTCTCTC CCCAGGCCTG TGGGTCTTCA TTGCCCAGCT CCTGCCCACA        3850

CTCCTGCCTG CTGCCCTGAC GAGAGTCATC                             3880

ATG TCT CTT GAG CAG AGG AGT CTG CAC TGC AAG CCT GAG GAA      3922

GCC CTT GAG GCC CAA CAA GAG GCC CTG GGC CTG GTG TGT GTG      3964

CAG GCT GCC ACC TCC TCC TCC TCT CCT CTG GTC CTG GGC ACC      4006

CTG GAG GAG GTG CCC ACT GCT GGG TCA ACA GAT CCT CCC CAG      4048

AGT CCT CAG GGA GCC TCC GCC TTT CCC ACT ACC ATC AAC TTC      4090

ACT CGA CAG AGG CAA CCC AGT GAG GGT TCC AGC AGC CGT GAA      4132

GAG GAG GGG CCA AGC ACC TCT TGT ATC CTG GAG TCC TTG TTC      4174

CGA GCA GTA ATC ACT AAG AAG GTG GCT GAT TTG GTT GGT TTT      4216

CTG CTC CTC AAA TAT CGA GCC AGG GAG CCA GTC ACA AAG GCA      4258

GAA ATG CTG GAG AGT GTC ATC AAA AAT TAC AAG CAC TGT TTT      4300

CCT GAG ATC TTC GGC AAA GCC TCT GAG TCC TTG CAG CTG GTC      4342

TTT GGC ATT GAC GTG AAG GAA GCA GAC CCC ACC GGC CAC TCC      4384

TAT GTC CTT GTC ACC TGC CTA GGT CTC TCC TAT GAT GGC CTG      4426

CTG GGT GAT AAT CAG ATC ATG CCC AAG ACA GGC TTC CTG ATA      4468
```

-continued

| | |
|---|---|
| ATT GTC CTG GTC ATG ATT GCA ATG GAG GGC GGC CAT GCT CCT | 4510 |
| GAG GAG GAA ATC TGG GAG GAG CTG AGT GTG ATG GAG GTG TAT | 4552 |
| GAT GGG AGG GAG CAC AGT GCC TAT GGG GAG CCC AGG AAG CTG | 4594 |
| CTC ACC CAA GAT TTG GTG CAG GAA AAG TAC CTG GAG TAC GGC | 4636 |
| AGG TGC CGG ACA GTG ATC CCG CAC GCT ATG AGT TCC TGT GGG | 4678 |
| GTC CAA GGG CCC TCG CTG AAA CCA GCT ATG TGA | 4711 |
| AAGTCCTTGA GTATGTGATC AAGGTCAGTG CAAGAGTTC | 4750 |
| GCTTTTTCTT CCCATCCCTG CGTGAAGCAG CTTTGAGAGA GGAGGAAGAG | 4800 |
| GGAGTCTGAG CATGAGTTGC AGCCAAGGCC AGTGGGAGGG GGACTGGGCC | 4850 |
| AGTGCACCTT CCAGGGCCGC GTCCAGCAGC TTCCCCTGCC TCGTGTGACA | 4900 |
| TGAGGCCCAT TCTTCACTCT GAAGAGACG GTCAGTGTTC TCAGTAGTAG | 4950 |
| GTTTCTGTTC TATTGGGTGA CTTGGAGATT TATCTTTGTT CTCTTTTGGA | 5000 |
| ATTGTTCAAA TGTTTTTTTT TAAGGGATGG TTGAATGAAC TTCAGCATCC | 5050 |
| AAGTTTATGA ATGACAGCAG TCACACAGTT CTGTGTATAT AGTTTAAGGG | 5100 |
| TAAGAGTCTT GTGTTTTATT CAGATTGGGA AATCCATTCT ATTTTGTGAA | 5150 |
| TTGGATAAT AACAGCAGTG GAATAAGTAC TTAGAAATGT GAAAAATGAG | 5200 |
| CAGTAAAATA GATGAGATAA AGAACTAAAG AAATTAAGAG ATAGTCAATT | 5250 |
| CTTGCCTTAT ACCTCAGTCT ATTCTGTAAA ATTTTTAAAG ATATATGCAT | 5300 |
| ACCTGGATTT CCTTGGCTTC TTTGAGAATG TAAGAGAAAT TAAATCTGAA | 5350 |
| TAAAGAATTC TTCCTGTTCA CTGGCTCTTT TCTTCTCCAT GCACTGAGCA | 5400 |
| TCTGCTTTTT GGAAGGCCCT GGGTTAGTAG TGGAGATGCT AAGGTAAGCC | 5450 |
| AGACTCATAC CCACCCATAG GGTCGTAGAG TCTAGGAGCT GCAGTCACGT | 5500 |
| AATCGAGGTG GCAAGATGTC CTCTAAAGAT GTAGGGAAAA GTGAGAGAGG | 5550 |
| GGTGAGGGTG TGGGGCTCCG GGTGAGAGTG GTGGAGTGTC AATGCCCTGA | 5600 |
| GCTGGGGCAT TTTGGGCTTT GGGAAACTGC AGTTCCTTCT GGGGGAGCTG | 5650 |
| ATTGTAATGA TCTTGGGTGG ATCC | 5674 |

(2) INFORMATION FOR SEQ ID NO: 9:

(i) SEQUENCE CHARACTERISTICS:
        (A) LENGTH: 4157 base pairs
        (B) TYPE: nucleic acid
        (C) STRANDEDNESS: single
        (D) TOPOLOGY: linear (ii) MOLECULE TYPE: genomic DNA (ix) FEATURE:
        (A) NAME/KEY: MAGE-2 gene (xi) SEQUENCE DESCRIPTION: SEQ ID NO: 9:

| | |
|---|---|
| CCCATCCAGA TCCCCATCCG GCAGAATCC GGTTCCACCC TTGCCGTGAA | 50 |
| CCCAGGGAAG TCACGGGCCC GGATGTGACG CCACTGACTT GCACATTGGA | 100 |
| GGTCAGAGGA CAGCGAGATT CTCGCCCTGA GCAACGGCCT GACGTCGGCG | 150 |
| GAGGGAAGCA GGCGCAGGCT CCGTGAGGAG GCAAGGTAAG ACGCCGAGGG | 200 |
| AGGACTGAGG CGGGCCTCAC CCCAGACAGA GGGCCCCCAA TTAATCCAGC | 250 |
| GCTGCCTCTG CTGCCGGGCC TGGACCACCC TGCAGGGGAA GACTTCTCAG | 300 |

-continued

| | |
|---|---|
| GCTCAGTCGC CACCACCTCA CCCCGCCACC CCCCGCCGCT TTAACCGCAG | 350 |
| GGAACTCTGG CGTAAGAGCT TTGTGTGACC AGGGCAGGGC TGGTTAGAAG | 400 |
| TGCTCAGGGC CCAGACTCAG CCAGGAATCA AGGTCAGGAC CCCAAGAGGG | 450 |
| GACTGAGGGC AACCCACCCC CTACCCTCAC TACCAATCCC ATCCCCCAAC | 500 |
| ACCAACCCCA CCCCCATCCC TCAAACACCA ACCCCACCCC CAAACCCCAT | 550 |
| TCCCATCTCC TCCCCCACCA CCATCCTGGC AGAATCCGGC TTTGCCCCTG | 600 |
| CAATCAACCC ACGGAAGCTC CGGGAATGGC GGCCAAGCAC GCGGATCCTG | 650 |
| ACGTTCACAT GTACGGCTAA GGGAGGGAAG GGGTTGGGTC TCGTGAGTAT | 700 |
| GGCCTTTGGG ATGCAGAGGA AGGGCCCAGG CCTCCTGGAA GACAGTGGAG | 750 |
| TCCTTAGGGG ACCCAGCATG CCAGGACAGG GGGCCCACTG TACCCCTGTC | 800 |
| TCAAACTGAG CCACCTTTTC ATTCAGCCGA GGGAATCCTA GGGATGCAGA | 850 |
| CCCACTTCAG GGGGTTGGGG CCCAGCCTGC GAGGAGTCAA GGGGAGGAAG | 900 |
| AAGAGGGAGG ACTGAGGGGA CCTTGGAGTC CAGATCAGTG GCAACCTTGG | 950 |
| GCTGGGGGAT CCTGGGCACA GTGGCCGAAT GTGCCCCGTG CTCATTGCAC | 1000 |
| CTTCAGGGTG ACAGAGAGTT GAGGGCTGTG GTCTGAGGGC TGGGACTTCA | 1050 |
| GGTCAGCAGA GGGAGGAATC CCAGGATCTG CCGGACCCAA GGTGTGCCCC | 1100 |
| CTTCATGAGG ACTCCCCATA CCCCCGGCCC AGAAAGAAGG GATGCCACAG | 1150 |
| AGTCTGGAAG TAAATTGTTC TTAGCTCTGG GGAACCTGA TCAGGGATGG | 1200 |
| CCCTAAGTGA CAATCTCATT TGTACCACAG GCAGGAGGTT GGGGAACCCT | 1250 |
| CAGGGAGATA AGGTGTTGGT GTAAAGAGGA GCTGTCTGCT CATTTCAGGG | 1300 |
| GGTTCCCCCT TGAGAAAGGG CAGTCCCTGG CAGGAGTAAA GATGAGTAAC | 1350 |
| CCACAGGAGG CCATCATAAC GTTCACCCTA GAACCAAAGG GGTCAGCCCT | 1400 |
| GGACAACGCA CGTGGGGTAA CAGGATGTGG CCCCTCCTCA CTTGTCTTTC | 1450 |
| CAGATCTCAG GGAGTTGATG ACCTTGTTTT CAGAAGGTGA CTCAGTCAAC | 1500 |
| ACAGGGCCC CTCTGGTCGA CAGATGCAGT GGTTCTAGGA TCTGCCAAGC | 1550 |
| ATCCAGGTGG AGAGCCTGAG GTAGGATTGA GGGTACCCCT GGGCCAGAAT | 1600 |
| GCAGCAAGGG GGCCCCATAG AAATCTGCCC TGCCCCTGCG GTTACTTCAG | 1650 |
| AGACCCTGGG CAGGGCTGTC AGCTGAAGTC CCTCCATTAT CTGGGATCTT | 1700 |
| TGATGTCAGG GAAGGGGAGG CCTTGGTCTG AAGGGGCTGG AGTCAGGTCA | 1750 |
| GTAGAGGGAG GGTCTCAGGC CCTGCCAGGA GTGGACGTGA GGACCAAGCG | 1800 |
| GACTCGTCAC CCAGGACACC TGGACTCCAA TGAATTTGAC ATCTCTCGTT | 1850 |
| GTCCTTCGCG GAGGACCTGG TCACGTATGG CCAGATGTGG GTCCCCTCTA | 1900 |
| TCTCCTTCTG TACCATATCA GGGATGTGAG TTCTTGACAT GAGAGATTCT | 1950 |
| CAAGCCAGCA AAAGGGTGGG ATTAGGCCCT ACAAGGAGAA AGGTGAGGGC | 2000 |
| CCTGAGTGAG CACAGAGGGG ACCCTCCACC CAAGTAGAGT GGGGACCTCA | 2050 |
| CGGAGTCTGG CCAACCCTGC TGAGACTTCT GGGAATCCGT GGCTGTGCTT | 2100 |
| GCAGTCTGCA CACTGAAGGC CCGTGCATTC CTCTCCCAGG AATCAGGAGC | 2150 |
| TCCAGGAACC AGGCAGTGAG GCCTTGGTCT GAGTCAGTGC CTCAGGTCAC | 2200 |
| AGAGCAGAGG GGACGCAGAC AGTGCCAACA CTGAAGGTTT GCCTGGAATG | 2250 |

| | |
|---|---|
| CACACCAAGG GCCCCACCCG CCCAGAACAA ATGGGACTCC AGAGGGCCTG | 2300 |
| GCCTCACCCT CCCTATTCTC AGTCCTGCAG CCTGAGCATG TGCTGGCCGG | 2350 |
| CTGTACCCTG AGGTGCCCTC CCACTTCCTC CTTCAGGTTC TGAGGGGAC | 2400 |
| AGGCTGACAA GTAGGACCCG AGGCACTGGA GGAGCATTGA AGGAGAAGAT | 2450 |
| CTGTAAGTAA GCCTTTGTCA GAGCCTCCAA GGTTCAGTTC AGTTCTCACC | 2500 |
| TAAGGCCTCA CACACGCTCC TTCTCTCCCC AGGCCTGTGG GTCTTCATTG | 2550 |
| CCCAGCTCCT GCCCGCACTC CTGCCTGCTG CCCTGACCAG AGTCATC | 2597 |
| ATG CCT CTT GAG CAG AGG AGT CAG CAC TGC AAG CCT GAA GAA | 2639 |
| GGC CTT GAG GCC CGA GGA GAG GCC CTG GGC CTG GTG GGT GCG | 2681 |
| CAG GCT CCT GCT ACT GAG GAG CAG CAG ACC GCT TCT TCC TCT | 2723 |
| TCT ACT CTA GTG GAA GTT ACC CTG GGG GAG GTG CCT GCT GCC | 2765 |
| GAC TCA CCG AGT CCT CCC CAC AGT CCT CAG GGA GCC TCC AGC | 2807 |
| TTC TCG ACT ACC ATC AAC TAC ACT CTT TGG AGA CAA TCC GAT | 2849 |
| GAG GGC TCC AGC AAC CAA GAA GAG GAG GGG CCA AGA ATG TTT | 2891 |
| CCC GAC CTG GAG TCC GAG TTC CAA GCA GCA ATC AGT AGG AAG | 2933 |
| ATG GTT GAG TTG GTT CAT TTT CTG CTC CTC AAG TAT CGA GCC | 2975 |
| AGG GAG CCG GTC ACA AAG GCA GAA ATG CTG GAG AGT GTC CTC | 3017 |
| AGA AAT TGC CAG GAC TTC TTT CCC GTG ATC TTC AGC AAA GCC | 3059 |
| TCC GAG TAC TTG CAG CTG GTC TTT GGC ATC GAG GTG GTG AAA | 3101 |
| GTG GTC CCC ATC AGC CAC TTG TAC ATC CTT GTC ACC TGC CTG | 3143 |
| GGC CTC TCC TAC GAT GGC CTG CTG GGC GAC AAT CAG GTC ATG | 3185 |
| CCC AAG ACA GGC CTC CTG ATA ATC GTC CTG GCC ATA ATC GCA | 3227 |
| ATA GAG GGC GAC TGT GCC CCT GAG GAG AAA ATC TGG GAG GAG | 3269 |
| CTG AGT ATG TTG GAG GTG TTT GAG GGG AGG GAG GAC AGT GTC | 3311 |
| TTC GCA CAT CCC AGG AAG CTG CTC ATG CAA GAT CTG GTG CAG | 3353 |
| GAA AAC TAC CTG GAG TAC CGG CAG GTG CCC GGC AGT GAT CCT | 3395 |
| GCA TGC TAC GAG TTC CTG TGG GGT CCA AGG GCC CTC ATT GAA | 3437 |
| ACC AGC TAT GTG AAA GTC CTG CAC CAT ACA CTA AAG ATC GGT | 3479 |
| GGA GAA CCT CAC ATT TCC TAC CCA CCC CTG CAT GAA CGG GCT | 3521 |
| TTG AGA GAG GGA GAA GAG TGA | 3542 |
| GTCTCAGCAC ATGTTGCAGC CAGGGCCAGT GGGAGGGGGT CTGGGCCAGT | 3592 |
| GCACCTTCCA GGGCCCCATC CATTAGCTTC CACTGCCTCG TGTGATATGA | 3642 |
| GGCCCATTCC TGCCTCTTTG AAGAGAGCAG TCAGCATTCT TAGCAGTGAG | 3692 |
| TTTCTGTTCT GTTGGATGAC TTTGAGATTT ATCTTTCTTT CCTGTTGGAA | 3742 |
| TTGTTCAAAT GTTCCTTTTA ACAAATGGTT GGATGAACTT CAGCATCCAA | 3792 |
| GTTTATGAAT GACAGTAGTC ACACATAGTG CTGTTTATAT AGTTTAGGGG | 3842 |
| TAAGAGTCCT GTTTTTTATT CAGATTGGGA AATCCATTCC ATTTTGTGAG | 3892 |
| TTGTCACATA ATAACAGCAG TGGAATATGT ATTTGCCTAT ATTGTGAACG | 3942 |
| AATTAGCAGT AAAATACATG ATACAAGGAA CTCAAAAGAT AGTTAATTCT | 3992 |
| TGCCTTATAC CTCAGTCTAT TATGTAAAAT TAAAATATG TGTATGTTTT | 4042 |

```
TGCTTCTTTG AGAATGCAAA AGAAATTAAA TCTGAATAAA TTCTTCCTGT           4092

TCACTGGCTC ATTTCTTTAC CATTCACTCA GCATCTGCTC TGTGGAAGGC           4142

CCTGGTAGTA GTGGG                                                 4157
```

(2) INFORMATION FOR SEQ ID NO: 10:

(i) SEQUENCE CHARACTERISTICS:
        (A) LENGTH: 662 base pairs
        (B) TYPE: nucleic acid
        (C) STRANDEDNESS: single
        (D) TOPOLOGY: linear (ii) MOLECULE TYPE: genomic DNA (ix) FEATURE:
        (A) NAME/KEY: MAGE-21 gene (xi) SEQUENCE DESCRIPTION: SEQ ID NO: 10:

```
GGATCCCCAT GGATCCAGGA AGAATCCAGT TCCACCCCTG CTGTGAACCC             50

AGGGAAGTCA CGGGGCCGGA TGTGACGCCA CTGACTTGCG CGTTGGAGGT            100

CAGAGAACAG CGAGATTCTC GCCCTGAGCA ACGGCCTGAC GTCGGCGGAG            150

GGAAGCAGGC GCAGGCTCCG TGAGGAGGCA AGGTAAGATG CCGAGGGAGG            200

ACTGAGGCGG GCCTCACCCC AGACAGAGGG CCCCCAATAA TCCAGCGCTG            250

CCTCTGCTGC CAGGCCTGGA CCACCCTGCA GGGGAAGACT TCTCAGGCTC            300

AGTCGCCACC ACCTCACCCC GCCACCCCCC GCCGCTTTAA CCGCAGGGAA            350

CTCTGGTGTA AGAGCTTTGT GTGACCAGGG CAGGGCTGGT TAGAAGTGCT            400

CAGGGCCCAG ACTCAGCCAG GAATCAAGGT CAGGACCCCA AGAGGGGACT            450

GAGGGTAACC CCCCCGCACC CCCACCACCA TTCCCATCCC CAACACCAA             500

CCCCACCCCC ATCCCCCAAC ACCAAACCCA CCACCATCGC TCAAACATCA            550

ACGGCACCCC CAAACCCCGA TTCCCATCCC CACCCATCCT GGCAGAATCG            600

GAGCTTTGCC CCTGCAATCA ACCCACGGAA GCTCCGGGAA TGGCGGCCAA            650

GCACGCGGAT CC                                                    662
```

(2) INFORMATION FOR SEQ ID NO: 11:

(i) SEQUENCE CHARACTERISTICS:
        (A) LENGTH: 1640 base pairs
        (B) TYPE: nucleic acid
        (C) STRANDEDNESS: single
        (D) TOPOLOGY: linear (ii) MOLECULE TYPE: cDNA to mRNA (ix) FEATURE:
        (A) NAME/KEY: cDNA MAGE-3

(xi) SEQUENCE DESCRIPTION: SEQ ID NO: 11:

```
GCCGCGAGGG AAGCCGGCCC AGGCTCGGTG AGGAGGCAAG GTTCTGAGGG             50

GACAGGCTGA CCTGGAGGAC CAGAGGCCCC CGGAGGAGCA CTGAAGGAGA            100

AGATCTGCCA GTGGGTCTCC ATTGCCCAGC TCCTGCCCAC ACTCCCGCCT            150

GTTGCCCTGA CCAGAGTCAT C                                          171

ATG CCT CTT GAG CAG AGG AGT CAG CAC TGC AAG CCT GAA GAA           213

GGC CTT GAG GCC CGA GGA GAG GCC CTG GGC CTG GTG GGT GCG           255

CAG GCT CCT GCT ACT GAG GAG CAG GAG GCT GCC TCC TCC TCT           297
```

| | |
|---|---|
| TCT ACT CTA GTT GAA GTC ACC CTG GGG GAG GTG CCT GCT GCC | 339 |
| GAG TCA CCA GAT CCT CCC CAG AGT CCT CAG GGA GCC TCC AGC | 381 |
| CTC CCC ACT ACC ATG AAC TAC CCT CTC TGG AGC CAA TCC TAT | 423 |
| GAG GAC TCC AGC AAC CAA GAA GAG GAG GGG CCA AGC ACC TTC | 465 |
| CCT GAC CTG GAG TCC GAG TTC CAA GCA GCA CTC AGT AGG AAG | 507 |
| GTG GCC GAG TTG GTT CAT TTT CTG CTC CTC AAG TAT CGA GCC | 549 |
| AGG GAG CCG TCA ACA AAG GCA GAA ATG CTG GGG AGT GTC GTC | 591 |
| GGA AAT TGG CAG TAT TTC TTT CCT GTG ATC TTC AGC AAA GCT | 633 |
| TCC AGT TCC TTG CAG CTG GTC TTT GGC ATC GAG CTG ATG GAA | 675 |
| GTG GAC CCC ATC GGC CAC TTG TAC ATC TTT GCC ACC TGC CTG | 717 |
| GGC CTC TCC TAC GAT GGC CTG CTG GGT GAC AAT CAG ATC ATG | 759 |
| CCC AAG GCA GGC CTC CTG ATA ATC GTC CTG GCC ATA ATC GCA | 801 |
| AGA GAG GGC GAC TGT GCC CCT GAG GAG AAA ATC TGG GAG GAG | 843 |
| CTG AGT GTG TTA GAG GTG TTT GAG GGG AGG GAA GAC AGT ATG | 885 |
| TTG GGG GAT CCC AAG AAG CTG CTC ACC CAA CAT TTC GTG CAG | 927 |
| GAA AAC TAC CTG GAG TAC CGG CAG GTC CCC GGC AGT GAT CCT | 969 |
| GCA TGT TAT GAA TTC CTG TGG GGT CCA AGG GCC CTC GTT GAA | 1011 |
| ACC AGC TAT GTG AAA GTC CTG CAC CAT ATG GTA AAG ATC AGT | 1053 |
| GGA GGA CCT CAC ATT TCC TAC CCA CCC CTG CAT GAG TGG GTT | 1095 |
| TTG AGA GAG GGG GAA GAG TGA | 1116 |
| GTCTGAGCAC GAGTTGCAGC CAGGGCCAGT GGGAGGGGGT CTGGGCCAGT | 1166 |
| GCACCTTCCG GGGCCGCATC CCTTAGTTTC CACTGCCTCC TGTGACGTGA | 1216 |
| GGCCCATTCT TCACTCTTTG AAGCGAGCAG TCAGCATTCT TAGTAGTGGG | 1266 |
| TTTCTGTTCT GTTGGATGAC TTTGAGATTA TTCTTTGTTT CCTGTTGGAG | 1316 |
| TTGTTCAAAT GTTCCTTTTA ACGGATGGTT GAATGAGCGT CAGCATCCAG | 1366 |
| GTTTATGAAT GACAGTAGTC ACACATAGTG CTGTTTATAT AGTTTAGGAG | 1416 |
| TAAGAGTCTT GttTTTTACT CAAATTgGGA AATCCATTCC ATTTTGTGAA | 1466 |
| TTGTGACATA ATAATAGCAG TGGTAAAAGT ATTTGCTTAA AATTGTGAGC | 1516 |
| GAATTAGCAA TAACATACAT GAGATAACTC AAGAAATCAA AAGATAGTTG | 1566 |
| ATTCTTGCCT TGTACCTCAA TCTATTCTGT AAAATTAAAC AAATATGCAA | 1616 |
| ACCAGGATTT CCTTGACTTC TTTG | 1640 |

(2) INFORMATION FOR SEQ ID NO: 12:

(i) SEQUENCE CHARACTERISTICS:
        (A) LENGTH: 943 base pairs
        (B) TYPE: nucleic acid
        (C) STRANDEDNESS: single
        (D) TOPOLOGY: linear (ii) MOLECULE TYPE: genomic DNA (ix) FEATURE:
        (A) NAME/KEY: MAGE-31 gene (xi) SEQUENCE DESCRIPTION: SEQ ID NO: 12:

| | |
|---|---|
| GGATCCTCCA CCCCAGTAGA GTGGGGACCT CACAGAGTCT GGCCAACCCT | 50 |

```
CCTGACAGTT CTGGGAATCC GTGGCTGCGT TTGCTGTCTG CACATTGGGG         100

GCCCGTGGAT TCCTCTCCCA GGAATCAGGA GCTCCAGGAA CAAGGCAGTG         150

AGGACTTGGT CTGAGGCAGT GTCCTCAGGT CACAGAGTAG AGGGGgCTCA         200

GATAGTGCCA ACGGTGAAGG TTTGCCTTGG ATTCAAACCA AGGGCCCCAC         250

CTGCCCCAGA ACACATGGAC TCCAGAGCGC CTGGCCTCAC CCTCAATACT         300

TTCAGTCCTG CAGCCTCAGC ATGCGCTGGC CGGATGTACC CTGAGGTGCC         350

CTCTCACTTC CTCCTTCAGG TTCTGAGGGG ACAGGCTGAC CTGGAGGACC         400

AGAGGCCCCC GGAGGAGCAC TGAAGGAGAA GATCTGTAAG TAAGCCTTTG         450

TTAGAGCCTC CAAGGTTCCA TTCAGTACTC AGCTGAGGTC TCTCACATGC         500

TCCCTCTCTC CCCAGGCCAG TGGGTCTCCA TTGCCCAGCT CCTGCCCACA         550

CTCCCGCCTG TTGCCCTGAC CAGAGTCATC                               580

ATG CCT CTT GAG CAG AGG AGT CAG CAC TGC AAG CCT GAA GAA        622

GGC CTT GAG GCC CGA GGA GAg GCC CTG GGC CTG GTG GGT GCG        664

CAG GCT CCT GCT ACT GAG GAG CAG GAG GCT GCC TCC TCC TCT        706

TCT AGT GTA GTT GAA GTC ACC CTG GGG GAG GTG CCT GCT GCC        748

GAG TCA CCA GAT CCT CCC CAG AGT CCT CAG GGA GCC TCC AGC        790

CTC CCC ACT ACC ATG AAC TAC CCT CTC TGG AGC CAA TCC TAT        832

GAG GAC TCC AGC AAC CAA GAA GAG GAG GGG CCA AGC ACC TTC        874

CCT GAC CTG GAG TCT GAG TTC CAA GCA GCA CTC AGT AGG AAG        916

GTG GCC AAG TTG GTT CAT TTT CTG CTC                            943

(2) INFORMATION FOR SEQ ID NO: 13:

(i) SEQUENCE CHARACTERISTICS:
        (A) LENGTH:  2531 base pairs
        (B) TYPE:    nucleic acid
        (C) STRANDEDNESS:  single
        (D) TOPOLOGY:  linear (ii) MOLECULE TYPE:  genomic DNA (ix) FEATURE:
        (A) NAME/KEY:  MAGE-4 gene (xi) SEQUENCE DESCRIPTION:  SEQ ID NO: 13:

GGATCCAGGC CCTGCCTGGA GAAATGTGAG GGCCCTGAGT GAACACAGTG          50

GGGATCATCC ACTCCATGAG AGTGGGGACC TCACAGAGTC CAGCCTACCC         100

TCTTGATGGC ACTGAGGGAC CGGGGCTGTG CTTACAGTCT GCACCCTAAG         150

GGCCCATGGA TTCCTCTCCT AGGAGCTCCA GGAACAAGGC AGTGAGGCCT         200

TGGTCTGAGA CAGTGTCCTC AGGTTACAGA GCAGAGGATG CACAGGCTGT         250

GCCAGCAGTG AATGTTTGCC CTGAATGCAC ACCAAGGGCC CCACCTGCCA         300

CAAGACACAT AGGACTCCAA AGAGTCTGGC CTCACCTCCC TACCATCAAT         350

CCTGCAGAAT CGACCTCTGC TGGCCGGCTA TACCCTGAGG TGCTCTCTCA         400

CTTCCTCCTT CAGGTTCTGA GCAGACAGGC CAACCGGAGA CAGGATTCCC         450

TGGAGGCCAC AGAGGAGCAC CAAGGAGAAG ATCTGTAAGT AAGCCTTTGT         500

TAGAGCCTCT AAGATTTGGT TCTCAGCTGA GGTCTCTCAC ATGCTCCCTC         550
```

-continued

| | |
|---|---|
| TCTCCGTAGG CCTGTGGGTC CCCATTGCCC AGCTTTTGCC TGCACTCTTG | 600 |
| CCTGCTGCCC TGACCAGAGT CATC | 624 |
| ATG TCT TCT GAG CAG AAG AGT CAG CAC TGC AAG CCT GAG GAA | 666 |
| GGC GTT GAG GCC CAA GAA GAG GCC CTG GGC CTG GTG GGT GCA | 708 |
| CAG GCT CCT ACT ACT GAG GAG CAG GAG GCT GCT GTC TCC TCC | 750 |
| TCC TCT CCT CTG GTC CCT GGC ACC CTG GAG GAA GTG CCT GCT | 792 |
| GCT GAG TCA GCA GGT CCT CCC CAG AGT CCT CAG GGA GCC TCT | 834 |
| GCC TTA CCC ACT ACC ATC AGC TTC ACT TGC TGG AGG CAA CCC | 876 |
| AAT GAG GGT TCC AGC AGC CAA GAA GAG GAG GGG CCA AGC ACC | 918 |
| TCG CCT GAC GCA GAG TCC TTG TTC CGA GAA GCA CTC AGT AAC | 960 |
| AAG GTG GAT GAG TTG GCT CAT TTT CTG CTC CGC AAG TAT CGA | 1002 |
| GCC AAG GAG CTG GTC ACA AAG GCA GAA ATG CTG GAG AGA GTC | 1044 |
| ATC AAA AAT TAC AAG CGC TGC TTT CCT GTG ATC TTC GGC AAA | 1086 |
| GCC TCC GAG TCC CTG AAG ATG ATC TTT GGC ATT GAC GTG AAG | 1128 |
| GAA GTG GAC CCC GCC AGC AAC ACC TAC ACC CTT GTC ACC TGC | 1170 |
| CTG GGC CTT TCC TAT GAT GGC CTG CTG GGT AAT AAT CAG ATC | 1212 |
| TTT CCC AAG ACA GGC CTT CTG ATA ATC GTC CTG GGC ACA ATT | 1254 |
| GCA ATG GAG GGC GAC AGC GCC TCT GAG GAG GAA ATC TGG GAG | 1296 |
| GAG CTG GGT GTG ATG GGG GTG TAT GAT GGG AGG GAG CAC ACT | 1338 |
| GTC TAT GGG GAG CCC AGG AAA CTG CTC ACC CAA GAT TGG GTG | 1380 |
| CAG GAA AAC TAC CTG GAG TAC CGG CAG GTA CCC GGC AGT AAT | 1422 |
| CCT GCG CGC TAT GAG TTC CTG TGG GGT CCA AGG GCT CTG GCT | 1464 |
| GAA ACC AGC TAT GTG AAA GTC CTG GAG CAT GTG GTC AGG GTC | 1506 |
| AAT GCA AGA GTT CGC ATT GCC TAC CCA TCC CTG CGT GAA GCA | 1548 |
| GCT TTG TTA GAG GAG GAA GAG GGA GTC TGA | 1578 |
| GCATGAGTTG CAGCCAGGGC TGTGGGGAAG GGGCAGGGCT GGGCCAGTGC | 1628 |
| ATCTAACAGC CCTGTGCAGC AGCTTCCCTT GCCTCGTGTA ACATGAGGCC | 1678 |
| CATTCTTCAC TCTGTTTGAA GAAAATAGTC AGTGTTCTTA GTAGTGGGTT | 1728 |
| TCTATTTTGT TGGATGACTT GGAGATTTAT CTCTGTTTCC TTTTACAATT | 1778 |
| GTTGAAATGT TCCTTTTAAT GGATGGTTGA ATTAACTTCA GCATCCAAGT | 1828 |
| TTATGAATCG TAGTTAACGT ATATTGCTGT TAATATAGTT TAGGAGTAAG | 1878 |
| AGTCTTGTTT TTTATTCAGA TTGGGAAATC CGTTCTATTT TGTGAATTTG | 1928 |
| GGACATAATA ACAGCAGTGG AGTAAGTATT TAGAAGTGTG AATTCACCGT | 1978 |
| GAAATAGGTG AGATAAATTA AAAGATACTT AATTCCCGCC TTATGCCTCA | 2028 |
| GTCTATTCTG TAAAATTTAA AAATATATAT GCATACCTGG ATTTCCTTGG | 2078 |
| CTTCGTGAAT GTAAGAGAAA TTAAATCTGA ATAAATAATT CTTTCTGTTA | 2128 |
| ACTGGCTCAT TTCTTCTCTA TGCACTGAGC ATCTGCTCTG TGGAAGGCCC | 2178 |
| AGGATTAGTA GTGGAGATAC TAGGGTAAGC CAGACACACA CCTACCGATA | 2228 |
| GGGTATTAAG AGTCTAGGAG CGCGGTCATA TAATTAAGGT GACAAGATGT | 2278 |
| CCTCTAAGAT GTAGGGGAAA AGTAACGAGT GTGGGTATGG GGCTCCAGGT | 2328 |

```
GAGAGTGGTC GGGTGTAAAT TCCCTGTGTG GGGCCTTTTG GGCTTTGGGA        2378

AACTGCATTT TCTTCTGAGG GATCTGATTC TAATGAAGCT TGGTGGGTCC        2428

AGGGCCAGAT TCTCAGAGGG AGAGGGAAAA GCCCAGATTG GAAAAGTTGC        2478

TCTGAGCAGT TCCTTTGTGA CAATGGATGA ACAGAGAGGA GCCTCTACCT        2528

GGG                                                          2531

(2) INFORMATION FOR SEQ ID NO: 14:

(i) SEQUENCE CHARACTERISTICS:
        (A) LENGTH: 2531 base pairs
        (B) TYPE: nucleic acid
        (C) STRANDEDNESS: single
        (D) TOPOLOGY: linear (ii) MOLECULE TYPE: genomic DNA (ix) FEATURE:
        (A) NAME/KEY: MAGE-41 gene (xi) SEQUENCE DESCRIPTION: SEQ ID NO: 14:

GGATCCAGGC CCTGCCTGGA GAAATGTGAG GGCCCTGAGT GAACACAGTG          50

GGGATCATCC ACTCCATGAG AGTGGGGACC TCACAGAGTC CAGCCTACCC         100

TCTTGATGGC ACTGAGGGAC CGGGGCTGTG CTTACAGTCT GCACCCTAAG         150

GGCCCATGGA TTCCTCTCCT AGGAGCTCCA GGAACAAGGC AGTGAGGCCT         200

TGGTCTGAGA CAGTGTCCTC AGGTTACAGA GCAGAGGATG CACAGGCTGT         250

GCCAGCAGTG AATGTTTGCC CTGAATGCAC ACCAAGGGCC CCACCTGCCA         300

CAAGACACAT AGGACTCCAA AGAGTCTGGC CTCACCTCCC TACCATCAAT         350

CCTGCAGAAT CGACCTCTGC TGGCCGGCTA TACCCTGAGG TGCTCTCTCA         400

CTTCCTCCTT CAGGTTCTGA GCAGACAGGC CAACCGGAGA CAGGATTCCC         450

TGGAGGCCAC AGAGGAGCAC CAAGGAGAAG ATCTGTAAGT AAGCCTTTGT         500

TAGAGCCTCT AAGATTTGGT TCTCAGCTGA GGTCTCTCAC ATGCTCCCTC         550

TCTCCGTAGG CCTGTGGGTC CCCATTGCCC AGCTTTTGCC TGCACTCTTG         600

CCTGCTGCCC TGAGCAGAGT CATC                                    624

ATG TCT TCT GAG CAG AAG AGT CAG CAC TGC AAG CCT GAG GAA        666

GGC GTT GAG GCC CAA GAA GAG GCC CTG GCC CTG GTG GGT GCG        708

CAG GCT CCT ACT ACT GAG GAG CAG GAG GCT GCT GTC TCC TCC        750

TCC TCT CCT CTG GTC CCT GGC ACC CTG GAG GAA GTG CCT GCT        792

GCT GAG TCA GCA GGT CCT CCC CAG AGT CCT CAG GGA GCC TCT        834

GCC TTA CCC ACT ACC ATC AGC TTC ACT GCT GGG AGG CAA CCC        876

AAT GAG GGT TCC AGC AGC CAA GAA GAG GAG GGG CCA AGC ACC        918

TCG CCT GAC GCA GAG TCC TTG TTC CGA GAA GCA CTC AGT AAC        960

AAG GTG GAT GAG TTG GCT CAT TTT CTG CTC CGC AAG TAT CGA       1002

GCC AAG GAG CTG GTC ACA AAG GCA GAA ATG CTG GAG AGA GTC       1044

ATC AAA AAT TAC AAG CGC TGC TTT CCT GTG ATC TTC GGC AAA       1086

GCC TCC GAG TCC CTG AAG ATG ATC TTT GGC ATT GAC GTG AAG       1128

GAA GTG GAC CCC ACC AGC AAC ACC TAC ACC CTT GTC ACC TGC       1170

CTG GGC CTT TCC TAT GAT GGC CTG CTG GGT AAT AAT CAG ATC       1212
```

```
TTT CCC AAG ACA GGC CTT CTG ATA ATC GTC CTG GGC ACA ATT       1254

GCA ATG GAG GGC GAC AGC GCC TCT GAG GAG GAA ATC TGG GAG       1296

GAG CTG GGT GTG ATG GGG GTG TAT GAT GGG AGG GAG CAC ACT       1338

GTC TAT GGG GAG CCC AGG AAA CTG CTC ACC CAA GAT TGG GTG       1380

CAG GAA AAC TAC CTG GAG TAC CGG CAG GTA CCC GGC AGT AAT       1422

CCT GCG CGC TAT GAG TTC CTG TGG GGT CCA AGG GCT CTG GCT       1464

GAA ACC AGC TAT GTG AAA GTC CTG GAG CAT GTG GTC AGG GTC       1506

AAT GCA AGA GTT CGC ATT GCC TAC CCA TCC CTG CGT GAA GCA       1548

GCT TTG TTA GAG GAG GAA GAG GGA GTC TGA                      1578

GCATGAGTTG CAGCCAGGGC TGTGGGAAG GGGCAGGGCT GGGCCAGTGC         1628

ATCTAACAGC CCTGTGCAGC AGCTTCCCTT GCCTCGTGTA ACATGAGGCC        1678

CATTCTTCAC TCTGTTTGAA GAAAATAGTC AGTGTTCTTA GTAGTGGGTT        1728

TCTATTTTGT TGGATGACTT GGAGATTTAT CTCTGTTTCC TTTTACAATT        1778

GTTGAAATGT TCCTTTTAAT GGATGGTTGA ATTAACTTCA GCATCCAAGT        1828

TTATGAATCG TAGTTAACGT ATATTGCTGT TAATATAGTT TAGGAGTAAG        1878

AGTCTTGTTT TTTATTCAGA TTGGGAAATC CGTTCTATTT TGTGAATTTG        1928

GGACATAATA ACAGCAGTGG AGTAAGTATT TAGAAGTGTG AATTCACCGT        1978

GAAATAGGTG AGATAAATTA AAAGATACTT AATTCCCGCC TTATGCCTCA        2028

GTCTATTCTG TAAAATTTAA AAATATATAT GCATACCTGG ATTTCCTTGG        2078

CTTCGTGAAT GTAAGAGAAA TTAAATCTGA ATAAATAATT CTTTCTGTTA        2128

ACTGGCTCAT TTCTTCTCTA TGCACTGAGC ATCTGCTCTG TGGAAGGCCC        2178

AGGATTAGTA GTGGAGATAC TAGGGTAAGC CAGACACACA CCTACCGATA        2228

GGGTATTAAG AGTCTAGGAG CGCGGTCATA TAATTAAGGT GACAAGATGT        2278

CCTCTAAGAT GTAGGGAAAA AGTAACGAGT GTGGGTATGG GGCTCCAGGT        2328

GAGAGTGGTC GGGTGTAAAT TCCCTGTGTG GGGCCTTTTG GGCTTTGGGA        2378

AACTCCATTT TCTTCTGAGG GATCTGATTC TAATGAAGCT TGGTGGGTCC        2428

AGGGCCAGAT TCTCAGAGGG AGAGGGAAAA GCCCAGATTG GAAAAGTTGC        2478

TCTGAGCGGT TCCTTTGTGA CAATGGATGA ACAGAGAGGA GCCTCTACCT        2528

GGG                                                           2531

(2) INFORMATION FOR SEQ ID NO: 15:

(i) SEQUENCE CHARACTERISTICS:
        (A) LENGTH:  1068 base pairs
        (B) TYPE:    nucleic acid
        (C) STRANDEDNESS:  single
        (D) TOPOLOGY:  linear (ii) MOLECULE TYPE:  cDNA to mRNA (ix) FEATURE:
        (A) NAME/KEY:  cDNA MAGE-4

(xi) SEQUENCE DESCRIPTION:  SEQ ID NO: 15:

G GGG CCA AGC ACC TCG CCT GAC GCA GAG TCC TTG TTC CGA          40

GAA GCA CTC AGT AAC AAG GTG GAT GAG TTG GCT CAT TTT CTG        82
```

-continued

| | |
|---|---|
| CTC CGC AAG TAT CGA GCC AAG GAG CTG GTC ACA AAG GCA GAA | 124 |
| ATG CTG GAG AGA GTC ATC AAA AAT TAC AAG CGC TGC TTT CCT | 166 |
| GTG ATC TTC GGC AAA GCC TCC GAG TCC CTG AAG ATG ATC TTT | 208 |
| GGC ATT GAC GTG AAG GAA GTG GAC CCC GCC AGC AAC ACC TAC | 250 |
| ACC CTT GTC ACC TGC CTG GGC CTT TCC TAT GAT GGC CTG CTG | 292 |
| GGT AAT AAT CAG ATC TTT CCC AAG ACA GGC TTT CTG ATA ATC | 334 |
| GTC CTG GGC ACA ATT GCA ATG GAG GGC GAC AGC GCC TCT GAG | 376 |
| GAG GAA ATC TGG GAG GAG CTG GGT GTG ATG GGG GTG TAT GAT | 418 |
| GGG AGG GAG CAC ACT GTC TAT GGG GAG CCC AGG AAA CTG CTC | 460 |
| ACC CAA GAT TGG GTG CAG GAA AAC TAC CTG GAG TAC CGG CAG | 502 |
| GTA CCC GGC AGT AAT CCT GCG CGC TAT GAG TTC CTG TGG GGT | 544 |
| CCA AGG GCT CTG GCT GAA ACC AGC TAT GTG AAA GTC CTG GAG | 586 |
| CAT GTG GTC AGG GTC AAT GCA AGA GTT CGC ATT GCC TAC CCA | 628 |
| TCC CTG CGT GAA GCA GCT TTG TTA GAG GAG GAA GAG GGA GTC | 670 |
| TGAGCATGAG TTGCAGCCAG GGCTGTGGGG AAGGGGCAGG GCTGGGCCAG | 720 |
| TGCATCTAAC AGCCCTGTGC AGCAGCTTCC CTTGCCTCGT GTAACATGAG | 770 |
| GCCCATTCTT CACTCTGTTT GAAGAAAATA GTCAGTGTTC TTAGTAGTGG | 820 |
| GTTTCTATTT TGTTGGATGA CTTGGAGATT TATCTCTGTT TCCTTTTACA | 870 |
| ATTGTTGAAA TGTTCCTTTT AATGGATGGT TGAATTAACT TCAGCATCCA | 920 |
| AGTTTATGAA TCGTAGTTAA CGTATATTGC TGTTAATATA GTTTAGGAGT | 970 |
| AAGAGTCTTG TTTTTTATTC AGATTGGGAA ATCCGTTCTA TTTTGTGAAT | 1020 |
| TTGGGACATA ATAACAGCAG TGGAGTAAGT ATTTAGAAGT GTGAATTC | 1068 |

(2) INFORMATION FOR SEQ ID NO: 16:

(i) SEQUENCE CHARACTERISTICS:
        (A) LENGTH: 2226 base pairs
        (B) TYPE: nucleic acid
        (C) STRANDEDNESS: single
        (D) TOPOLOGY: linear (ii) MOLECULE TYPE: genomic DNA (ix) FEATURE:
        (A) NAME/KEY: MAGE-5 gene (xi) SEQUENCE DESCRIPTION: SEQ ID NO: 16:

| | |
|---|---|
| GGATCCAGGC CTTGCCAGGA GAAAGGTGAG GGCCCTGTGT GAGCACAGAG | 50 |
| GGGACCATTC ACCCCAAGAG GGTGGAGACC TCACAGATTC CAGCCTACCC | 100 |
| TCCTGTTAGC ACTGGGGGCC TGAGGCTGTG CTTGCAGTCT GCACCCTGAG | 150 |
| GGCCCATGCA TTCCTCTTCC AGGAGCTCCA GGAAACAGAC ACTGAGGCCT | 200 |
| TGGTCTGAGG CCGTGCCCTC AGGTCACAGA GCAGAGGAGA TGCAGACGTC | 250 |
| TAGTGCCAGC AGTGAACGTT TGCCTTGAAT GCACACTAAT GGCCCCCATC | 300 |
| GCCCCAGAAC ATATGGGACT CCAGAGCACC TGGCCTCACC CTCTCTACTG | 350 |
| TCAGTCCTGC AGAATCAGCC TCTGCTTGCT TGTGTACCCT GAGGTGCCCT | 400 |
| CTCACTTTTT CCTTCAGGTT CTCAGGGGAC AGGCTGACCA GGATCACCAG | 450 |
| GAAGCTCCAG AGGATCCCCA GGAGGCCCTA GAGGAGCACC AAAGGAGAAG | 500 |

```
ATCTGTAAGT AAGCCTTTGT TAGAGCCTCC AAGGTTCAGT TTTTAGCTGA            550
GGCTTCTCAC ATGCTCCCTC TCTCTCCAGG CCAGTGGGTC TCCATTGCCC            600
AGCTCCTGCC CACACTCCTG CCTGTTGCGG TGACCAGAGT CGTC                  644
ATG TCT CTT GAG CAG AAG AGT CAG CAC TGC AAG CCT GAG GAA           686
CTC CTC TGG TCC CAG GCA CCC TGG GGG AGG TGC CTG CTG CTG           728
GGT CAC CAG GTC CTC TCA AGA GTC CTC AGG GAG CCT CCG CCA           770
TCC CCA CTG CCA TCG ATT TCA CTC TAT GGA GGC AAT CCA TTA           812
AGG GCT CCA GCA ACC AAG AAG AGG AGG GGC AAA GCA CCT CCC           854
CTG ACC CAG AGT CTG TGT TCC GAG CAG CAC TCA GTA AGA AGG           896
TGG CTG ACT TGA                                                   908
TTCATTTTCT GCTCCTCAAG TATTAAGTCA AGGAGCTGGT CACAAAGGCA            958
GAAATGCTGG AGAGCGTCAT CAAAAATTAC AAGCGCTGCT TTCCTGAGAT            1008
CTTCGGCAAA GCCTCCGAGT CCTTGCAGCT GGTCTTTGGC ATTGACGTGA            1058
AGGAAGCGGA CCCCACCAGC AACACCTACA CCCTTGTCAC CTGCCTGGGA            1108
CTCCTATGAT GGCCTGCTGG TTGATAATAA TCAGATCATG CCCAAGACGG            1158
GCCTCCTGAT AATCGTCTTG GGCATGATTG CAATGGAGGG CAAATGCGTC            1208
CCTGAGGAGA AAATCTGGGA GGAGCTGAGT GTGATGAAGG TGTATGTTGG            1258
GAGGGAGCAC AGTGTCTGTG GGGAGCCCAG GAAGCTGCTC ACCCAAGATT            1308
TGGTGCAGGA AAACTACCTG GAGTACCGGC AGGTGCCCAG CAGTGATCCC            1358
ATATGCTATG AGTTACTGTG GGTCCAAGG GCACTCGCTG CTTGAAAGTA             1408
CTGGAGCACG TGGTCAGGGT CAATGCAAGA GTTCTCATTT CCTACCCATC            1458
CCTGCGTGAA GCAGCTTTGA GAGAGGAGGA AGAGGGAGTC TGAGCATGAG            1508
CTGCAGCCAG GGCCACTGCG AGGGGGGCTG GGCCAGTGCA CCTTCCAGGG            1558
CTCCGTCCAG TAGTTTCCCC TGCCTTAATG TGACATGAGG CCCATTCTTC            1608
TCTCTTTGAA GAGAGCAGTC AACATTCTTA GTAGTGGGTT TCTGTTCTAT            1658
TGGATGACTT TGAGATTTGT CTTTGTTTCC TTTTGGAATT GTTCAAATGT            1708
TTCTTTTAAT GGGTGGTTGA ATGAACTTCA GCATTCAAAT TTATGAATGA            1758
CAGTAGTCAC ACATAGTGCT GTTTATATAG TTTAGGAGTA AGAGTCTTGT            1808
TTTTTATTCA GATTGGGAAA TCCATTCCAT TTTGTGAATT GGGACATAGT            1858
TACAGCAGTG GAATAAGTAT TCATTTAGAA ATGTGAATGA GCAGTAAAAC            1908
TGATGACATA AAGAAATTAA AAGATATTTA ATTCTTGCTT ATACTCAGTC            1958
TATTCGGTAA AATTTTTTTT AAAAAATGTG CATACCTGGA TTTCCTTGGC            2008
TTCTTTGAGA ATGTAAGACA AATTAAATCT GAATAAATCA TTCTCCCTGT            2058
TCACTGGCTC ATTTATTCTC TATGCACTGA GCATTTGCTC TGTGGAAGGC            2108
CCTGGGTTAA TAGTGGAGAT GCTAAGGTAA GCCAGACTCA CCCCTACCCA            2158
CAGGGTAGTA AGTCTAGGA GCAGCAGTCA TATAATTAAG GTGGAGAGAT             2208
GCCCTCTAAG ATGTAGAG                                               2226
```

(2) INFORMATION FOR SEQ ID NO: 17:

(i) SEQUENCE CHARACTERISTICS:

(A) LENGTH: 2305 base pairs
         (B) TYPE: nucleic acid
         (C) STRANDEDNESS: single
         (D) TOPOLOGY: linear (ii) MOLECULE TYPE: genomic DNA (ix) FEATURE:
         (A) NAME/KEY: MAGE-51 gene (xi) SEQUENCE DESCRIPTION: SEQ ID NO: 17:

| | |
|---|---|
| GGATCCAGGC CTTGCCAGGA GAAAGGTGAG GGCCCTGTGT GAGCACAGAG | 50 |
| GGGACCATTC ACCCCAAGAG GGTGGAGACC TCACAGATTC CAGCCTACCC | 100 |
| TCCTGTTAGC ACTGGGGCC TGAGGCTGTG CTTGCAGTCT GCACCCTGAG | 150 |
| GGCCCATGCA TTCCTCTTCC AGGAGCTCCA GGAAACAGAC ACTGAGGCCT | 200 |
| TGGTCTGAGG CCGTGCCCTC AGGTCACAGA GCAGAGGAGA TGCAGACGTC | 250 |
| TAGTGCCAGC AGTGAACGTT TGCCTTGAAT GCACACTAAT GGCCCCCATC | 300 |
| GCCCCAGAAC ATATGGGACT CCAGAGCACC TGGCCTCACC CTCTCTACTG | 350 |
| TCAGTCCTGC AGAATCAGCC TCTGCTTGCT TGTGTACCCT GAGGTGCCCT | 400 |
| CTCACTTTTT CCTTCAGGTT CTCAGGGGAC AGGCTGACCA GGATCACCAG | 450 |
| GAAGCTCCAG AGGATCCCCA GGAGGCCCTA GAGGAGCACC AAAGGAGAAG | 500 |
| ATCTGTAAGT AAGCCTTTGT TAGAGCCTCC AAGGTTCAGT TTTTAGCTGA | 550 |
| GGCTTCTCAC ATGCTCCCTC TCTCTCCAGG CCAGTGGGTC TCCATTGCCC | 600 |
| AGCTCCTGCC CACACTCCTG CCTGTTGCGG TGACCAGAGT CGTC | 644 |
| ATG TCT CTT GAG CAG AAG AGT CAG CAC TGC AAG CCT GAG GAA | 686 |
| GGC CTT GAC ACC CAA GAA GAG CCC TGG GCC TGG TGG GTG TGC | 728 |
| AGG CTG CCA CTA CTG AGG AGC AGG AGG CTG TGT CCT CCT CCT | 770 |
| CTC CTC TGG TCC CAG GCA CCC TGG GGG AGG TGC CTG CTG CTG | 812 |
| GGT CAC CAG GTC CTC TCA AGA GTC CTC AGG GAG CCT CCG CCA | 854 |
| TCC CCA CTG CCA TCG ATT TCA CTC TAT GGA GGC AAT CCA TTA | 896 |
| AGG GCT CCA GCA ACC AAG AAG AGG AGG GGC CAA GCA CCT CCC | 938 |
| CTG ACC CAG AGT CTG TGT TCC GAG CAG CAC TCA GTA AGA AGG | 980 |
| TGG CTG ACT TGA | 992 |
| TTCATTTTCT GCTCCTCAAG TATTAAGTCA AGGAGCCGGT CACAAAGGCA | 1042 |
| GAAATGCTGG AGAGCGTCAT CAAAAATTAC AAGCGCTGCT TCCTGAGAT | 1092 |
| CTTCGGCAAA GCCTCCGAGT CCTTGCAGCT GGTCTTTGGC ATTGACGTGA | 1142 |
| AGGAAGCGGA CCCCACCAGC AACACCTACA CCCTTGTCAC CTGCCTGGGA | 1192 |
| CTCCTATGAT GGCCTGGTGG TTTAATCAGA TCATGCCCAA GACGGGCCTC | 1242 |
| CTGATAATCG TCTTGGGCAT GATTGCAATG GAGGGCAAAT GCGTCCCTGA | 1292 |
| GGAGAAAATC TGGGAGGAGC TGGGTGTGAT GAAGGTGTAT GTTGGGAGGG | 1342 |
| AGCACAGTGT CTGTGGGGAG CCCAGGAAGC TGCTCACCCA AGATTTGGTG | 1392 |
| CAGGAAAACT ACCTGGAGTA CCGCAGGTGC CCAGCAGTGA TCCCATATGC | 1442 |
| TATGAGTTAC TGTGGGGTCC AAGGGCACTC GCTGCTTGAA AGTACTGGAG | 1492 |
| CACGTGGTCA GGGTCAATGC AAGAGTTCTC ATTTCCTACC CATCCCTGCA | 1542 |
| TGAAGCAGCT TTGAGAGAGG AGGAAGAGGG AGTCTGAGCA TGAGCTGCAG | 1592 |

```
CCAGGGCCAC TGCGAGGGGG GCTGGGCCAG TGCACCTTCC AGGGCTCCGT              1642

CCAGTAGTTT CCCCTGCCTT AATGTGACAT GAGGCCCATT CTTCTCTCTT              1692

TGAAGAGAGC AGTCAACATT CTTAGTAGTG GGTTTCTGTT CTATTGGATG              1742

ACTTTGAGAT TTGTCTTTGT TTCCTTTTGG AATTGTTCAA ATGTTCCTTT              1792

TAATGGGTGG TTGAATGAAC TTCAGCATTC AAATTTATGA ATGACAGTAG              1842

TCACACATAG TGCTGTTTAT ATAGTTTAGG AGTAAGAGTC TTGTTTTTTA              1892

TTCAGATTGG GAAATCCATT CCATTTTGTG AATTGGGACA TAGTTACAGC              1942

AGTGGAATAA GTATTCATTT AGAAATGTGA ATGAGCAGTA AAACTGATGA              1992

GATAAAGAAA TTAAAAGATA TTTAATTCTT GCCTTATACT CAGTCTATTC              2042

GGTAAAATTT TTTTTTAAAA ATGTGCATAC CTGGATTTCC TTGGCTTCTT              2092

TGAGAATGTA AGACAAATTA AATCTGAATA AATCATTCTC CCTGTTCACT              2142

GGCTCATTTA TTCTCTATGC ACTGAGCATT TGCTCTGTGG AAGGCCCTGG              2192

GTTAATAGTG GAGATGCTAA GGTAAGCCAG ACTCACCCCT ACCCACAGGG              2242

TAGTAAAGTC TAGGAGCAGC AGTCATATAA TTAAGGTGGA GAGATGCCCT              2292

CTAAGATGTA GAG                                                     2305

(2) INFORMATION FOR SEQ ID NO: 18:

(i) SEQUENCE CHARACTERISTICS:
        (A) LENGTH:  225 base pairs
        (B) TYPE:    nucleic acid
        (C) STRANDEDNESS:  single
        (D) TOPOLOGY:  linear (ii) MOLECULE TYPE:  cDNA (ix) FEATURE:
        (A) NAME/KEY:  MAGE-6 gene (xi) SEQUENCE DESCRIPTION:  SEQ ID NO: 18:

TAT TTC TTT CCT GTG ATC TTC AGC AAA GCT TCC GAT TCC TTG              42

CAG CTG GTC TTT GGC ATC GAG CTG ATG GAA GTG GAC CCC ATC              84

GGC CAC GTG TAC ATC TTT GCC ACC TGC CTG GGC CTC TCC TAC             126

GAT GGC CTG CTG GGT GAC AAT CAG ATC ATG CCC AGG ACA GGC             168

TTC CTG ATA ATC ATC CTG GCC ATA ATC GCA AGA GAG GGC GAC             210

TGT GCC CCT GAG GAG                                                 225

(2) INFORMATION FOR SEQ ID NO: 19:

(i) SEQUENCE CHARACTERISTICS:
        (A) LENGTH:  1947 base pairs
        (B) TYPE:    nucleic acid
        (C) STRANDEDNESS:  single
        (D) TOPOLOGY:  linear (ii) MOLECULE TYPE:  genomic DNA (ix) FEATURE:
        (A) NAME/KEY:  MAGE-7 gene (xi) SEQUENCE DESCRIPTION:  SEQ ID NO: 19:

TGAATGGACA ACAAGGGCCC CACACTCCCC AGAACACAAG GGACTCCAGA               50

GAGCCCAGCC TCACCTTCCC TACTGTCAGT CCTGCAGCCT CAGCCTCTGC              100
```

-continued

| | |
|---|---|
| TGGCCGGCTG TACCCTGAGG TGCCCTCTCA CTTCCTCCTT CAGGTTCTCA | 150 |
| GCGGACAGGC CGGCCAGGAG GTCAGAAGCC CCAGGAGGCC CCAGAGGAGC | 200 |
| ACCGAAGGAG AAGATCTGTA AGTAGGCCTT TGTTAGGGCC TCCAGGGCGT | 250 |
| GGTTCACAAA TGAGGCCCCT CACAAGCTCC TTCTCTCCCC AGATCTGTGG | 300 |
| GTTCCTCCCC ATCGCCCAGC TGCTGCCCGC ACTCCAGCCT GCTGCCCTGA | 350 |
| CCAGAGTCAT CATGTCTTCT GAGCAGAGGA GTCAGCACTG CAAGCCTGAG | 400 |
| GATGCCTTGA GGCCCAAGGA CAGGAGGCTC TGGGCCTGGT GGGTGCGCAG | 450 |
| GCTCCCGCCA CCGAGGAGCA CGAGGCTGCC TCCTCCTTCA CTCTGATTGA | 500 |
| AGGCACCCTG GAGGAGGTGC CTGCTGCTGG GTCCCCCAGT CCTCCCCTGA | 550 |
| GTCTCAGGGT TCCTCCTTTT CCCTGACCAT CAGCAACAAC ACTCTATGGA | 600 |
| GCCAATCCAG TGAGGGCACC AGCAGCCGGG AAGAGGAGGG GCCAACCACC | 650 |
| TAGACACACC CCGCTCACCT GGCGTCCTTG TTCCA | 685 |
| ATG GGA AGG TGG CTG AGT TGG TTC GCT TCC TGC TGC ACA AGT | 727 |
| ATC GAG TCA AGG AGC TGG TCA CAA AGG CAG AAA TGC TGG ACA | 769 |
| GTG TCA TCA AAA ATT ACA AGC ACT AGT TTC CTT GTG ATC TAT | 811 |
| GGC AAA GCC TCA GAG TGC ATG CAG GTG ATG TTT GGC ATT GAC | 853 |
| ATG AAG GAA GTG GAC CCC GCG GCC ACT CCT ACG TCC TTG TCA | 895 |
| CCT GCT TGG GCC TCT CCT ACA ATG GCC TGC TGG GTG ATG ATC | 937 |
| AGA GCA TGC CCG AGA CCG GCC TTC TGA | 964 |
| TTATGGTCTT GACCATGATC TTAATGGAGG GCCACTGTGC CCCTGAGGAG | 1014 |
| GCAATCTGGG AAGCGTTGAG TGTAATGGTG TATGATGGGA TGGAGCAGTT | 1064 |
| TCTTTGGGCA GCTGAGGAAG CTGCTCACCC AAGATTGGGT GCAGGAAAAC | 1114 |
| TACCTGCAAT ACCGCCAGGT GCCCAGCAGT GATCCCCCGT GCTACCAGTT | 1164 |
| CCTGTGGGGT CCAAGGGCCC TCATTGAAAC CAGCTATGTG AAAGTCCTGG | 1214 |
| AGTATGCAGC CAGGGTCAGT ACTAAAGAGA GCATTTCCTA CCCATCCCTG | 1264 |
| CATGAAGAGG CTTTGGGAGA GGAGGAAGAG GGAGTCTGAG CAGAAGTTGC | 1314 |
| AGCCAGGGCC AGTGGGGCAG ATTGGGGGAG GGCCTGGGCA GTGCACGTTC | 1364 |
| CACACATCCA CCACCTTCCC TGTCCTGTTA CATGAGGCCC ATTCTTCACT | 1414 |
| CTGTGTTTGA AGAGAGCAGT CAATGTTCTC AGTAGCGGGG AGTGTGTTGG | 1464 |
| GTGTGAGGGA ATACAAGGTG GACCATCTCT CAGTTCCTGT TCTCTTGGGC | 1514 |
| GATTTGGAGG TTTATCTTTG TTTCCTTTTG CAGTCGTTCA AATGTTCCTT | 1564 |
| TTAATGGATG GTGTAATGAA CTTCAACATT CATTTCATGT ATGACAGTAG | 1614 |
| GCAGACTTAC TGTTTTTTAT ATAGTTAAAA GTAAGTGCAT TGTTTTTTAT | 1664 |
| TTATGTAAGA AAATCTATGT TATTTCTTGA ATTGGGACAA CATAACATAG | 1714 |
| CAGAGGATTA AGTACCTTTT ATAATGTGAA AGAACAAAGC GGTAAAATGG | 1764 |
| GTGAGATAAA GAAATAAAGA AATTAAATTG GCTGGGCACG GTGGCTCACG | 1814 |
| CCTGTAATCC CAGCACTTTA GGAGGCAGAG GCACGGGGAT CACGAGGTCA | 1864 |
| GGAGATCGAG ACCATTCTGG CTAACACAGT GAAACACCAT CTCTATTAAA | 1914 |
| AATACAAAAC TTAGCCGGGC GTGGTGGCGG GTG | 1947 |

(2) INFORMATION FOR SEQ ID NO: 20:

(i) SEQUENCE CHARACTERISTICS:
        (A) LENGTH: 1810 base pairs
        (B) TYPE: nucleic acid
        (C) STRANDEDNESS: single
        (D) TOPOLOGY: linear (ii) MOLECULE TYPE: genomic DNA (ix) FEATURE:
        (A) NAME/KEY: MAGE-8 gene (xi) SEQUENCE DESCRIPTION: SEQ ID NO: 20:

```
GAGCTCCAGG AACCAGGCTG TGAGGTCTTG GTCTGAGGCA GTATCTTCAA         50

TCACAGAGCA TAAGAGGCCC AGGCAGTAGT AGCAGTCAAG CTGAGGTGGT        100

GTTTCCCCTG TATGTATACC AGAGGCCCCT CTGGCATCAG AACAGCAGGA        150

ACCCCACAGT TCCTGGCCCT ACCAGCCCTT TTGTCAGTCC TGGAGCCTTG        200

GCCTTTGCCA GGAGGCTGCA CCCTGAGATG CCCTCTCAAT TTCTCCTTCA        250

GGTTCGCAGA GAACAGGCCA GCCAGGAGGT CAGGAGGCCC CAGAGAAGCA        300

CTGAAGAAGA CCTGTAAGTA GACCTTTGTT AGGGCATCCA GGGTGTAGTA        350

CCCAGCTGAG GCCTCTCACA CGCTTCCTCT CTCCCCAGGC CTGTGGGTCT        400

CAATTGCCCA GCTCCGGCCC ACACTCTCCT GCTGCCCTGA CCTGAGTCAT        450

C                                                            451

ATG CTT CTT GGG CAG AAG AGT CAG CGC TAC AAG GCT GAG GAA       493

GGC CTT CAG GCC CAA GGA GAG GCA CCA GGG CTT ATG GAT GTG       535

CAG ATT CCC ACA GCT GAG GAG CAG AAG GCT GCA TCC TCC TCC       577

TCT ACT CTG ATC ATG GGA ACC CTT GAG GAG GTG ACT GAT TCT       619

GGG TCA CCA AGT CCT CCC CAG AGT CCT GAG GGT GCC TCC TCT       661

TCC CTG ACT GTC ACC GAC AGC ACT CTG TGG AGC CAA TCC GAT       703

GAG GGT TCC AGC AGC AAT GAA GAG GAG GGG CCA AGC ACC TCC       745

CCG GAC CCA GCT CAC CTG GAG TCC CTG TTC CGG GAA GCA CTT       787

GAT GAG AAA GTG GCT GAG TTA GTT CGT TTC CTG CTC CGC AAA       829

TAT CAA ATT AAG GAG CCG GTC ACA AAG GCA GAA ATG CTT GAG       871

AGT GTC ATC AAA AAT TAC AAG AAC CAC TTT CCT GAT ATC TTC       913

AGC AAA GCC TCT GAG TGC ATG CAG GTG ATC TTT GGC ATT GAT       955

GTG AAG GAA GTG GAC CCT GCC GGC CAC TCC TAC ATC CTT GTC       997

ACC TGC CTG GGC CTC TCC TAT GAT GGC CTG CTG GGT GAT GAT      1039

CAG AGT ACG CCC AAG ACC GGC CTC CTG ATA ATC GTC CTG GGC      1081

ATG ATC TTA ATG GAG GGC AGC CGC GCC CCG GAG GAG GCA ATC      1123

TGG GAA GCA TTG AGT GTG ATG GGG GCT GTA TGA                  1156

TGGGAGGGAG CACAGTGTCT ATTGGAAGCT CAGGAAGCTG CTCACCCAAG       1206

AGTGGGTGCA GGAGAACTAC CTGGAGTACC GCCAGGCGCC CGGCAGTGAT       1256

CCTGTGCGCT ACGAGTTCCT GTGGGGTCCA AGGGCCCTTG CTGAAACCAG       1306

CTATGTGAAA GTCCTGGAGC ATGTGGTCAG GGTCAATGCA AGAGTTCGCA       1356

TTTCCTACCC ATCCCTGCAT GAAGAGGCTT TGGGAGAGGA GAAAGGAGTT       1406
```

-continued

| | |
|---|---|
| TGAGCAGGAG TTGCAGCTAG GGCCAGTGGG GCAGGTTGTG GGAGGGCCTG | 1456 |
| GGCCAGTGCA CGTTCCAGGG CCACATCCAC CACTTTCCCT GCTCTGTTAC | 1506 |
| ATGAGGCCCA TTCTTCACTC TGTGTTTGAA GAGAGCAGTC ACAGTTCTCA | 1556 |
| GTAGTGGGGA GCATGTTGGG TGTGAGGGAA CACAGTGTGG ACCATCTCTC | 1606 |
| AGTTCCTGTT CTATTGGGCG ATTTGGAGGT TTATCTTTGT TTCCTTTTGG | 1656 |
| AATTGTTCCA ATGTTCCTTC TAATGGATGG TGTAATGAAC TTCAACATTC | 1706 |
| ATTTTATGTA TGACAGTAGA CAGACTTACT GCTTTTTATA TAGTTTAGGA | 1756 |
| GTAAGAGTCT TGCTTTTCAT TTATACTGGG AAACCCATGT TATTTCTTGA | 1806 |
| ATTC | 1810 |

(2) INFORMATION FOR SEQ ID NO: 21:

(i) SEQUENCE CHARACTERISTICS:
        (A) LENGTH: 1412 base pairs
        (B) TYPE: nucleic acid
        (C) STRANDEDNESS: single
        (D) TOPOLOGY: linear (ii) MOLECULE TYPE: genomic DNA (ix) FEATURE:
        (A) NAME/KEY: MAGE-9 gene (xi) SEQUENCE DESCRIPTION: SEQ ID NO: 21:

| | |
|---|---|
| TCTGAGACAG TGTCCTCAGG TCGCAGAGCA GAGGAGACCC AGGCAGTGTC | 50 |
| AGCAGTGAAG GTGAAGTGTT CACCCTGAAT GTGCACCAAG GGCCCCACCT | 100 |
| GCCCCAGCAC ACATGGGACC CCATAGCACC TGGCCCCATT CCCCCTACTG | 150 |
| TCACTCATAG AGCCTTGATC TCTGCAGGCT AGCTGCACGC TGAGTAGCCC | 200 |
| TCTCACTTCC TCCCTCAGGT TCTCGGGACA GGCTAACCAG GAGGACAGGA | 250 |
| GCCCAAGAG GCCCCAGAGC AGCACTGACG AAGACCTGTA AGTCAGCCTT | 300 |
| TGTTAGAACC TCCAAGGTTC GGTTCTCAGC TGAAGTCTCT CACACACTCC | 350 |
| CTCTCTCCCC AGGCCTGTGG GTCTCCATCG CCCAGCTCCT GCCCACGCTC | 400 |
| CTGACTGCTG CCCTGACCAG AGTCATC | 427 |
| ATG TCT CTC GAG CAG AGG AGT CCG CAC TGC AAG CCT GAT GAA | 469 |
| GAC CTT GAA GCC CAA GGA GAG GAC TTG GGC CTG ATG GGT GCA | 511 |
| CAG GAA CCC ACA GGC GAG GAG GAG GAG ACT ACC TCC TCC TCT | 553 |
| GAC AGC AAG GAG GAG GAG GTG TCT GCT GCT GGG TCA TCA AGT | 595 |
| CCT CCC CAG AGT CCT CAG GGA GGC GCT TCC TCC TCC ATT TCC | 637 |
| GTC TAC TAC ACT TTA TGG AGC CAA TTC GAT GAG GGC TCC AGC | 679 |
| AGT CAA GAA GAG GAA GAG CCA AGC TCC TCG GTC GAC CCA GCT | 721 |
| CAG CTG GAG TTC ATG TTC CAA GAA GCA CTG AAA TTG AAG GTG | 763 |
| GCT GAG TTG GTT CAT TTC CTG CTC CAC AAA TAT CGA GTC AAG | 805 |
| GAG CCG GTC ACA AAG GCA GAA ATG CTG GAG AGC GTC ATC AAA | 847 |
| AAT TAC AAG CGC TAC TTT CCT GTG ATC TTC GGC AAA GCC TCC | 889 |
| GAG TTC ATG CAG GTG ATC TTT GGC ACT GAT GTG AAG GAG GTG | 931 |
| GAC CCC GCC GGC CAC TCC TAC ATC CTT GTC ACT GCT CTT GGC | 973 |
| CTC TCG TGC GAT AGC ATG CTG GGT GAT GGT CAT AGC ATG CCC | 1015 |

```
AAG GCC GCC CTC CTG ATC ATT GTC CTG GGT GTG ATC CTA ACC          1057

AAA GAC AAC TGC GCC CCT GAA GAG GTT ATC TGG GAA GCG TTG          1099

AGT GTG ATG GGG GTG TAT GTT GGG AAG GAG CAC ATG TTC TAC          1141

GGG GAG CCC AGG AAG CTG CTC ACC CAA GAT TGG GTG CAG GAA          1183

AAC TAC CTG GAG TAC CGG CAG GTG CCC GGC AGT GAT CCT GCG          1225

CAC TAC GAG TTC CTG TGG GGT TCC AAG GCC CAC GCT GAA ACC          1267

AGC TAT GAG AAG GTC ATA AAT TAT TTG GTC ATG CTC AAT GCA          1309

AGA GAG CCC ATC TGC TAC CCA TCC CTT TAT GAA GAG GTT TTG          1351

GGA GAG GAG CAA GAG GGA GTC TGA                                 1375

GCACCAGCCG CAGCCGGGGC CAAAGTTTGT GGGGTCA                        1412

(2) INFORMATION FOR SEQ ID NO: 22:

(i) SEQUENCE CHARACTERISTICS:
        (A) LENGTH: 920 base pairs
        (B) TYPE: nucleic acid
        (C) STRANDEDNESS: single
        (D) TOPOLOGY: linear (ii) MOLECULE TYPE: genomic DNA (ix) FEATURE:
        (A) NAME/KEY: MAGE-10 gene (xi) SEQUENCE DESCRIPTION: SEQ ID NO: 22:

ACCTGCTCCA GGACAAAGTG GACCCCACTG CATCAGCTCC ACCTACCCTA            50

CTGTCAGTCC TGGAGCCTTG GCCTCTGCCG GCTGCATCCT GAGGAGCCAT           100

CTCTCACTTC CTTCTTCAGG TTCTCAGGGG ACAGGGAGAG CAAGAGGTCA           150

AGAGCTGTGG GACACCACAG AGCAGCACTG AAGGAGAAGA CCTGTAAGTT           200

GGCCTTTGTT AGAACCTCCA GGGTGTGGTT CTCAGCTGTG GCCACTTACA           250

CCCTCCCTCT CTCCCCAGGC CTGTGGGTCC CCATCGCCCA AGTCCTGCCC           300

ACACTCCCAC CTGCTACCCT GATCAGAGTC ATC                             333

ATG CCT CGA GCT CCA AAG CGT CAG CGC TGC ATG CCT GAA GAA          375

GAT CTT CAA TCC CAA AGT GAG ACA CAG GGC CTC GAG GGT GCA          417

CAG GCT CCC CTG GCT GTG GAG GAG GAT GCT TCA TCA TCC ACT          459

TCC ACC AGC TCC TCT TTT CCA TCC TCT TTT CCC TCC TCC TCC          501

TCT TCC TCC TCC TCC TCC TGC TAT CCT CTA ATA CCA AGC ACC          543

CCA GAG GAG GTT TCT GCT GAT GAT GAG ACA CCA AAT CCT CCC          585

CAG AGT GCT CAG ATA GCC TGC TCC TCC CCC TCG TCG TTG CT           627

TCC CTT CCA TTA GAT CAA TCT GAT GAG GGC TCC AGC AGC CAA          669

AAG GAG GAG AGT CCA AGC ACC CTA CAG GTC CTG CCA GAC AGT          711

GAG TCT TTA CCC AGA AGT GAG ATA GAT GAA AAG GTG ACT GAT          753

TTG GTG CAG TTT CTG CTC TTC AAG TAT CAA ATG AAG GAG CCG          795

ATC ACA AAG GCA GAA ATA CTG GAG AGT GTC ATA AAA AAT TAT          837

GAA GAC CAC TTC CCT TTG TTG TTT AGT GAA GCC TCC GAG TGC          879

ATG CTG CTG GTC TTT GGC ATT GAT GTA AAG GAA GTG GAT CC           920
```

(2) INFORMATION FOR SEQ ID NO: 23:

(i) SEQUENCE CHARACTERISTICS:
        (A) LENGTH: 1107 base pairs
        (B) TYPE: nucleic acid
        (C) STRANDEDNESS: single
        (D) TOPOLOGY: linear (ii) MOLECULE TYPE: genomic DNA (ix) FEATURE:
        (A) NAME/KEY: MAGE-11 gene (xi) SEQUENCE DESCRIPTION: SEQ ID NO: 23:

```
AGAGAACAGG CCAACCTGGA GGACAGGAGT CCCAGGAGAA CCCAGAGGAT          50

CACTGGAGGA GAACAAGTGT AAGTAGGCCT TTGTTAGATT CTCCATGGTT         100

CATATCTCAT CTGAGTCTGT TCTCACGCTC CCTCTCTCCC CAGGCTGTGG         150

GGCCCCATCA CCCAGATATT TCCCACAGTT CGGCCTGCTG ACCTAACCAG         200

AGTCATCATG CCTCTTGAGC AAAGAAGTCA GCACTGCAAG CCTGAGGAAG         250

CCTTCAGGCC AAGAAGAAG ACCTGGGCCT GGTGGGTGCA CAGGCTCTCC          300

AAGCTGAGGA GCAGGAGGCT GCCTTCTTCT CCTCTACTCT GAATGTGGGC         350

ACTCTAGAGG AGTTGCCTGC TGCTGAGTCA CCAAGTCCTC CCCAGAGTCC         400

TCAGGAAGAG TCCTTCTCTC CCACTGCCAT GGATGCCATC TTTGGGAGCC         450

TATCTGATGA GGGCTCTGGC AGCCAAGAAA AGGAGGGGCC AAGTACCTCG         500

CCTGACCTGA TAGACCCTGA GTCCTTTTCC CAAGATATAC TACATGACAA         550

GATAATTGAT TTGGTTCATT TATTCTCCGC AAGTATCGAG TCAAGGGGCT         600

GATCACAAAG GCAGAA                                              616

ATG CTG GGG AGT GTC ATC AAA AAT TAT GAG GAC TAC TTT CCT        658

GAG ATA TTT AGG GAA GCC TCT GTA TGC ATG CAA CTG CTC TTT        700

GGC ATT GAT GTG AAG GAA GTG GAC CCC ACT AGC CAC TCC TAT        742

GTC CTT GTC ACC TCC CTC AAC CTC TCT TAT GAT GGC ATA CAG        784

TGT AAT GAG CAG AGC ATG CCC AAG TCT GGC CTC CTG ATA ATA        826

GTC CTG GGT GTA ATC TTC ATG GAG GGG AAC TGC ATC CCT GAA        868

GAG GTT ATG TGG GAA GTC CTG AGC ATT ATG GGG GTG TAT GCT        910

GGA AGG GAG CAC TTC CTC TTT GGG GAG CCC AAG AGG CTC CTT        952

ACC CAA AAT TGG GTG CAG GAA AAG TAC CTG GTG TAC CGG CAG        994

GTG CCC GGC ACT GAT CCT GCA TGC TAT GAG TTC CTG TGG GGT       1036

CCA AGG GCC CAC GCT GAG ACC AGC AAG ATG AAA GTT CTT GAG       1078

TAC ATA GCC AAT GCC AAT GGG AGG GAT CC                        1107
```

(2) INFORMATION FOR SEQ ID NO: 24:

(i) SEQUENCE CHARACTERISTICS:
        (A) LENGTH: 2150 base pairs
        (B) TYPE: nucleic acid
        (C) STRANDEDNESS: single
        (D) TOPOLOGY: linear (ii) MOLECULE TYPE: genomic DNA (ix) FEATURE:
        (A) NAME/KEY: smage-I (xi) SEQUENCE DESCRIPTION: SEQ ID NO: 24:

| | |
|---|---|
| TCTGTCTGCA TATGCCTCCA CTTGTGTGTA GCAGTCTCAA ATGGATCTCT | 50 |
| CTCTACAGAC CTCTGTCTGT GTCTGGCACC CTAAGTGGCT TTGCATGGGC | 100 |
| ACAGGTTTCT GCCCCTGCAT GGAGCTTAAA TAGATCTTTC TCCACAGGCC | 150 |
| TATACCCCTG CATTGTAAGT TTAAGTGGCT TTATGTGGAT ACAGGTCTCT | 200 |
| GCCCTTGTAT GCAGGCCTAA GTTTTTCTGT CTGCTTAACC CCTCCAAGTG | 250 |
| AAGCTAGTGA AAGATCTAAC CCACTTTTGG AAGTCTGAAA CTAGACTTTT | 300 |
| ATGCAGTGGC CTAACAAGTT TTAATTTCTT CCACAGGGTT TGCAGAAAAG | 350 |
| AGCTTGATCC ACGAGTTCAG AAGTCCTGGT ATGTTCCTAG AAAG | 394 |
| ATG TTC TCC TGG AAA GCT TCA AAA GCC AGG TCT CCA TTA AGT | 436 |
| CCA AGG TAT TCT CTA CCT GGT AGT ACA GAG GTA CTT ACA GGT | 478 |
| TGT CAT TCT TAT CCT TCC AGA TTC CTG TCT GCC AGC TCT TTT | 520 |
| ACT TCA GCC CTG AGC ACA GTC AAC ATG CCT AGG GGT CAA AAG | 562 |
| AGT AAG ACC CGC TCC CGT GCA AAA CGA CAG CAG TCA CGC AGG | 604 |
| GAG GTT CCA GTA GTT CAG CCC ACT GCA GAG GAA GCA GGG TCT | 646 |
| TCT CCT GTT GAC CAG AGT GCT GGG TCC AGC TTC CCT GGT GGT | 688 |
| TCT GCT CCT CAG GGT GTG AAA ACC CCT GGA TCT TTT GGT GCA | 730 |
| GGT GTA TCC TGC ACA GGC TCT GGT ATA GGT GGT AGA AAT GCT | 772 |
| GCT GTC CTG CCT GAT ACA AAA AGT TCA GAT GGC ACC CAG GCA | 814 |
| GGG ACT TCC ATT CAG CAC ACA CTG AAA GAT CCT ATC ATG AGG | 856 |
| AAG GCT AGT GTG CTG ATA GAA TTC CTG CTA GAT AAA TTT AAG | 898 |
| ATG AAA GAA GCA GTT ACA AGG AGT GAA ATG CTG GCA GTA GTT | 940 |
| AAC AAG AAG TAT AAG GAG CAA TTC CCT GAG ATC CTC AGG AGA | 982 |
| ACT TCT GCA CGC CTA GAA TTA GTC TTT GGT CTT GAG TTG AAG | 1024 |
| GAA ATT GAT CCC AGC ACT CAT TCC TAT TTG CTG GTA GGC AAA | 1066 |
| CTG GGT CTT TCC ACT GAG GGA AGT TTG AGT AGT AAC TGG GGG | 1108 |
| TTG CCT AGG ACA GGT CTC CTA ATG TCT GTC CTA GGT GTG ATC | 1150 |
| TTC ATG AAG GGT AAC CGT GCC ACT GAG CAA GAG GTC TGG CAA | 1192 |
| TTT CTG CAT GGA GTG GGG TAT GCT GGG AAG AAG CAC TTG | 1234 |
| ATC TTT GGC GAG CCT GAG GAG TTT ATA AGA GAT GTA GTG CGG | 1276 |
| GAA AAT TAC CTG GAG TAC CGC CAG GTA CCT GGC AGT GAT CCC | 1318 |
| CCA AGC TAT GAG TTC CTG TGG GGA CCC AGA GCC CAT GCT GAA | 1360 |
| ACA ACC AAG ATG AAA GTC CTG GAA GTT TTA GCT AAA GTC AAT | 1402 |
| GGC ACA GTC CCT AGT GCC TTC CCT AAT CTC TAC CAG TTG GCT | 1444 |
| CTT AGA GAT CAG GCA GGA GGG GTG CCA AGA AGG AGA GTT CAA | 1486 |
| GGC AAG GGT GTT CAT TCC AAG GCC CCA TCC CAA AAG TCC TCT | 1528 |
| AAC ATG TAG | 1537 |
| TTGAGTCTGT TCTGTTGTGT TTGAAAAACA GTCAGGCTCC TAATCAGTAG | 1587 |
| AGAGTTCATA GCCTACCAGA ACCAACATGC ATCCATTCTT GGCCTGTTAT | 1637 |

-continued

| | |
|---|---|
| ACATTAGTAG AATGGAGGCT ATTTTTGTTA CTTTTCAAAT GTTTGTTTAA | 1687 |
| CTAAACAGTG CTTTTTGCCA TGCTTCTTGT TAACTGCATA AAGAGGTAAC | 1737 |
| TGTCACTTGT CAGATTAGGA CTTGTTTTGT TATTTGCAAC AAACTGGAAA | 1787 |
| ACATTATTTT GTTTTTACTA AAACATTGTG TAACATTGCA TTGGAGAAGG | 1837 |
| GATTGTCATG GCAATGTGAT ATCATACAGT GGTGAAACAA CAGTGAAGTG | 1887 |
| GGAAAGTTTA TATTGTTAAT TTTGAAAATT TTATGAGTGT GATTGCTGTA | 1937 |
| TACTTTTTTC TTTTTTGTAT AATGCTAAGT GAAATAAAGT TGGATTTGAT | 1987 |
| GACTTTACTC AAATTCATTA GAAAGTAAAT CGTAAAACTC TATTACTTTA | 2037 |
| TTATTTTCTT CAATTATGAA TTAAGCATTG GTTATCTGGA AGTTTCTCCA | 2087 |
| GTAGCACAGG ATCTAGTATG AAATGTATCT AGTATAGGCA CTGACAGTGA | 2137 |
| GTTATCAGAG TCT | 2150 |

(2) INFORMATION FOR SEQ ID NO: 25:

(i) SEQUENCE CHARACTERISTICS:
        (A) LENGTH: 2099 base pairs
        (B) TYPE: nucleic acid
        (C) STRANDEDNESS: single
        (D) TOPOLOGY: linear (ii) MOLECULE TYPE: genomic DNA (ix) FEATURE:
        (A) NAME/KEY: smage-II (xi) SEQUENCE DESCRIPTION: SEQ ID NO: 25:

| | |
|---|---|
| ACCTTATTGG GTCTGTCTGC ATATGCCTCC ACTTGTGTGT AGCAGTCTCA | 50 |
| AATGGATCTC TCTCTACAGA CCTCTGTCTG TGTCTGGCAC CCTAAGTGGC | 100 |
| TTTGCATGGG CACAGGTTTC TGCCCCTGCA TGGAGCTTAA ATAGATCTTT | 150 |
| CTCCACAGGC CTATACCCCT GCATTGTAAG TTTAAGTGGC TTTATGTGGA | 200 |
| TACAGGTCTC TGCCCTTGTA TGCAGGCCTA AGTTTTCTG TCTGCTTAGC | 250 |
| CCCTCCAAGT GAAGCTAGTG AAAGATCTAA CCCACTTTTG GAAGTCTGAA | 300 |
| ACTAGACTTT TATGCAGTGG CCTAACAAGT TTTAATTTCT TCCACAGGGT | 350 |
| TTGCAGAAAA GAGCTTGATC CACGAGTTCG GAAGTCCTGG TATGTTCCTA | 400 |
| GAAAGATGTT CTCCTGGAAA GCTTCAAAAG CCAGGTCTCC ATTAAGTCCA | 450 |
| AGGTATTCTC TACCTGGTAG TACAGAGGTA CTTACAGGTT GTCATTCTTA | 500 |
| TCTTTCCAGA TTCCTGTCTG CCAGCTCTTT TACTTCAGCC CTGAGCACAG | 550 |
| TCAACATGCC TAGGGGTCAA AAGAGTAAGA CCCGCTCCCG TGCAAAACGA | 600 |
| CAGCAGTCAC GCAGGGAGGT TCCAGTAGTT CAGCCCACTG CAGAGGAAGC | 650 |
| AGGGTCTTCT CCTGTTGACC AGAGTGCTGG GTCCAGCTTC CCTGGTGGTT | 700 |
| CTGCTCCTCA GGGTGTGAAA ACCCCTGGAT CTTTTGGTGC AGGTGTATCC | 750 |
| TGCACAGGCT CTGGTATAGG TGGTAGAAAT GCTGCTGTCC TGCCTGATAC | 800 |
| AAAAAGTTCA GATGGCACCC AGGCAGGGAC TTCCATTCAG CACACACTGA | 850 |
| AAGATCCTAT CATGAGGAAG CTAGTGTGC TGATAGAATT CCTGCTAGAT | 900 |
| AAGTTTAAGA TGAAAGAAGC AGTTACAAGG AGTGAAATGC TGGCAGTAGT | 950 |
| TAACAAGAAG TATAAGGAGC AATTCCCTGA GATCCTCAGG AGAACTTCTG | 1000 |
| CACGCCTAGA ATTAGTCTTT GGTCTTGAGT TGAAGGAAAT TGATCCCAGC | 1050 |

-continued

```
ACTCATTCCT ATTTGCTGGT AGGCAAACTG GGTCTTTCCA CTGAGGGAAG       1100

TTTGAGTAGT AACTGGGGGT TGCCTAGGAC AGGTCTCCTA ATGTCTGTCC       1150

TAGGTGTGAT CTTCATGAAG GGTAACCGTG CCACTGAGCA AGAGGTCTGG       1200

CAATTTCTGC ATGGAGTGGG GGTATATGCT GGGAAGAAGC ACTTGATCTT       1250

TGGCGAGCCT GAGGAGTTTA TAAGAGATGT AGTGCGGGAA AATTACCTGG       1300

AGTACCGCCA GGTACCTGGC AGTGATCCCC CAAGCTATGA GTTCCTGTGG       1350

GGACCCAGAG CCCATGCTGA ACAACCAAG ATGAAAGTCC TGGAAGTTTT        1400

AGCTAAAGTC AATGGCACAG TCCCTAGTGC CTTCCCTAAT CTCTACCAGT       1450

TGGCTCTTAG AGATCAGGCA GGAGGGGTGC AAGAAGGAG AGTTCAAGGC        1500

AAGGGTGTTC ATTCCAAGGC CCCATCCCAA AAGTCCTCTA ACATGTAGTT       1550

GAGTCTGTTC TGTTGTGTTT GAAAAACAGT CAGGCTCCTA ATCAGTAGAG       1600

AGTTCATAGC CTACCAGAAC CAACATGCAT CCATTCTTGG CCTGTTATAC       1650

ATTAGTAGAA TGGAGGCTAT TTTTGTTACT TTTCAAATGT TTGTTTAACT       1700

AAACAGTGCT TTTTGCCATG CTTCTTGTTA ACTGCATAAA GAGGTAACTG       1750

TCACTTGTCA GATTAGGACT TGTTTTGTTA TTTGCAACAA ACTGGAAAAC       1800

ATTATTTTGT TTTTACTAAA ACATTGTGTA ACATTGCATT GGAGAAGGGA       1850

TTGTCATGGC AATGTGATAT CATACAGTGG TGAAACAACA GTGAAGTGGG       1900

AAAGTTTATA TTGTTAGTTT TGAAAATTTT ATGAGTGTGA TTGCTGTATA       1950

CTTTTTTCTT TTTTGTATAA TGCTAAGTGA AATAAAGTTG GATTTGATGA       2000

CTTTACTCAA ATTCATTAGA AAGTAAATCA TAAAACTCTA TTACTTTATT       2050

ATTTTCTTCA ATTATTAATT AAGCATTGGT TATCTGGAAG TTTCTCCAG        2099
```

(2) INFORMATION FOR SEQ ID NO: 26:

(i) SEQUENCE CHARACTERISTICS:
        (A) LENGTH: 9 amino acids
        (B) TYPE: amino acids
        (D) TOPOLOGY: linear (ii) MOLECULE TYPE: protein (xi) SEQUENCE DESCRIPTION: SEQ ID NO: 26:

Glu Ala Asp Pro Thr Gly His Ser Tyr
                 5

(2) INFORMATION FOR SEQ ID NO: 27:

(i) SEQUENCE CHARACTERISTICS:
        (A) LENGTH: 20 nucleotides
        (B) TYPE: nucleic acid
        (C) STRANDEDNESS: single
        (D) TOPOLOGY: linear (xi) SEQUENCE DESCRIPTION: SEQ ID NO: 27:

ACTCAGCTCC TCCCAGATTT                          20

(2) INFORMATION FOR SEQ ID NO: 28:

(i) SEQUENCE CHARACTERISTICS:
        (A) LENGTH: 17 nucleotides
        (B) TYPE: nucleic acid
        (C) STRANDEDNESS: single
        (D) TOPOLOGY: linear

```
    (xi) SEQUENCE DESCRIPTION:  SEQ ID NO: 28:

GAAGAGGAGG GGCCAAG                                                  17

(2) INFORMATION FOR SEQ ID NO: 29:

(i) SEQUENCE CHARACTERISTICS:
        (A) LENGTH:   18 nucleotides
        (B) TYPE:     nucleic acid
        (C) STRANDEDNESS: single
        (D) TOPOLOGY:  linear (xi) SEQUENCE DESCRIPTION:  SEQ ID NO: 29:

TCTTGTATCC TGGAGTCC                                                 18

(2) INFORMATION FOR SEQ ID NO: 30:

(i) SEQUENCE CHARACTERISTICS:
        (A) LENGTH:   18 nucleotides
        (B) TYPE:     nucleic acid
        (C) STRANDEDNESS: single
        (D) TOPOLOGY:  linear (xi) SEQUENCE DESCRIPTION:  SEQ ID NO: 30:

TTGCCAAGAT CTCAGGAA                                                 18
```

US 6,235,525 B1

ISOLATED NUCLEIC ACID MOLECULES CODING FOR TUMOR REJECTION ANTIGEN PRECURSOR MAGE-3 AND USES THEREOF

RELATED APPLICATION

This application is a continuation-in-part of PCT Application PCT/US92/04354 filed on May 22, 1992 designating the United States, which is a continuation-in-part of Ser. No. 07/807,043, filed Dec. 12, 1991 now U.S. Pat. No. 5,342,774 which is a continuation-in-part of Ser. No. 07/764,365, filed Sep. 23, 1991, now abandoned, which is a continuation-in-part of Ser. No. 07/728,838, filed Jul. 9, 1991, now abandoned, which is a continuation-in-part of Ser. No. 07/705,702, filed May 23, 1991, and now abandoned.

FIELD OF THE INVENTION

This invention relates in general to the field of immunogenetics as applied to the study of oncology. More specifically, it relates to the study and analysis of mechanisms by which tumors are recognized by the organism's immune system such as through the presentation of so-called tumor rejection antigens, and the expression of what will be referred to herein as "tumor rejection antigen precursors" or "TRAPs". Most specifically, it refers to nucleic acid molecules coding for one such TRAP, i.e., MAGE-3, which is processed to a tumor rejection antigen or "TRA" presented by HLA-A1 molecules.

BACKGROUND AND PRIOR ART

The study of the recognition or lack of recognition of cancer cells by a host organism has proceeded in many different directions. Understanding of the field presumes some understanding of both basic immunology and oncology.

Early research on mouse tumors revealed that these displayed molecules which led to rejection of tumor cells when transplanted into syngeneic animals. These molecules are "recognized" by T-cells in the recipient animal, and provoke a cytolytic T-cell response with lysis of the transplanted cells. This evidence was first obtained with tumors induced in vitro by chemical carcinogens, such as methylcholanthrene. The antigens expressed by the tumors and which elicited the T-cell response were found to be different for each tumor. See Prehn, et al., J. Natl. Canc. Inst. 18: 769–778 (1957); Klein et al., Cancer Res. 20: 1561–1572 (1960); Gross, Cancer Res. 3: 326–333 (1943), Basombrio, Cancer Res. 30: 2458–2462 (1970) for general teachings on inducing tumors with chemical carcinogens and differences in cell surface antigens. This class of antigens has come to be known as "tumor specific transplantation antigens" or "TSTAs". Following the observation of the presentation of such antigens when induced by chemical carcinogens, similar results were obtained when tumors were induced in vitro via ultraviolet radiation. See Kripke, J. Natl. Canc. Inst. 53: 333–1336 (1974).

While T-cell mediated immune responses were observed for the types of tumor described supra, spontaneous tumors were thought to be generally non-immunogenic. These were therefore believed not to present antigens which provoked a response to the tumor in the tumor carrying subject. See Hewitt, et al., Brit. J. Cancer 33: 241–259 (1976).

The family of $tum^-$ antigen presenting cell lines are immunogenic variants obtained by mutagenesis of mouse tumor cells or cell lines, as described by Boon et al., J. Exp. Med. 152: 1184–1193 (1980), the disclosure of which is incorporated by reference. To elaborate, $tum^-$ antigens are obtained by mutating tumor cells which do not generate an immune response in syngeneic mice and will form tumors (i.e., "$tum^+$" cells). When these $tum^+$ cells are mutagenized, they are rejected by syngeneic mice, and fail to form tumors (thus "$tum^-$"). See Boon et al., Proc. Natl. Acad. Sci. USA 74: 272 (1977), the disclosure of which is incorporated by reference. Many tumor types have been shown to exhibit this phenomenon. See, e.g., Frost et al., Cancer Res. 43: 125 (1983).

It appears that $tum^-$ variants fail to form progressive tumors because they elicit an immune rejection process. The evidence in favor of this hypothesis includes the ability of "$tum^-$" variants of tumors, i.e., those which do not normally form tumors, to do so in mice with immune systems suppressed by sublethal irradiation, Van Pel et al., Proc. Natl, Acad. Sci. USA 76: 5282–5285 (1979); and the observation that intraperitoneally injected $tum^-$ cells of mastocytoma P815 multiply exponentially for 12–15 days, and then are eliminated in only a few days in the midst of an influx of lymphocytes and macrophages (Uyttenhove et al., J. Exp. Med. 152: 1175–1183 (1980)). Further evidence includes the observation that mice acquire an immune memory which permits them to resist subsequent challenge to the same $tum^-$ variant, even when immunosuppressive amounts of radiation are administered with the following challenge of cells (Boon et al., Proc. Natl, Acad. Sci. USA 74: 272–275 (1977); Van Pel et al., supra; Uyttenhove et al., supra). Later research found that when spontaneous tumors were subjected to mutagenesis, immunogenic variants were produced which did generate a response. Indeed, these variants were able to elicit an immune protective response against the original tumor. See Van Pel et al., J. Exp. Med. 157: 1992–2001 (1983). Thus, it has been shown that it is possible to elicit presentation of a so-called "tumor rejection antigen" in a tumor which is a target for a syngeneic rejection response. Similar results have been obtained when foreign genes have been transfected into spontaneous tumors. See Fearson et al., Cancer Res. 48: 2975–1980 (1988) in this regard.

A class of antigens has been recognized which are presented on the surface of tumor cells and are recognized by cytotoxic T cells, leading to lysis. This class of antigens will be referred to as "tumor rejection antigens" or "TRAs" hereafter. TRAs may or may not elicit antibody responses. The extent to which these antigens have been studied, has been via cytolytic T cell characterization studies, in vitro i.e., the study of the identification of the antigen by a particular cytolytic T cell ("CTL" hereafter) subset. The subset proliferates upon recognition of the presented tumor rejection antigen, and the cells presenting the antigen are lysed. Characterization studies have identified CTL clones which specifically lyse cells expressing the antigens. Examples of this work may be found in Levy et al., Adv. Cancer Res. 24: 1–59 (1977); Boon et al., J. Exp. Med. 152: 1184–1193 (1980); Brunner et al., J. Immunol. 124: 1627–1634 (1980); Maryanski et al., Eur. J. Immunol. 124: 1627–1634 (1980); Maryanski et al., Eur. J. Immunol. 12: 406–412 (1982); Palladino et al., Canc. Res. 47: 5074–5079 (1987). This type of analysis is required for other types of antigens recognized by CTLs, including minor histocompatibility antigens, the male specific H–Y antigens, and a class of antigens, referred to as "$tum^-$" antigens, and discussed herein.

A tumor exemplary of the subject matter described supra is known as P815. See DePlaen et al., Proc. Natl. Acad. Sci. USA 85: 2274–2278 (1988); Szikora et al., EMBO J 9:

1041–1050 (1990), and Sibille et al., J. Exp. Med. 172: 35–45 (1990), the disclosures of which are incorporated by reference. The P815 tumor is a mastocytoma, induced in a DBA/2 mouse with methylcholanthrene and cultured as both an in vitro tumor and a cell line. The P815 line has generated many tum⁻ variants following mutagenesis, including variants referred to as P91A (DePlaen, supra), 35B (Szikora, supra), and P198 (Sibille, supra). In contrast to tumor rejection antigens—and this is a key distinction—the tum⁻ antigens are only present after the tumor cells are mutagenized. Tumor rejection antigens are present on cells of a given tumor without mutagenesis. Hence, with reference to the literature, a cell line can be tum⁺, such as the line referred to as "P1", and can be provoked to produce tum⁻ variants. Since the tum⁻ phenotype differs from that of the parent cell line, one expects a difference in the DNA of tum⁻ cell lines as compared to their tum⁺ parental lines, and this difference can be exploited to locate the gene of interest in tum⁻ cells. As a result, it was found that genes of tum⁻ variants such as P91A, 35B and P198 differ from their normal alleles by point mutations in the coding regions of the gene. See Szikora and Sibille, supra, and Lurquin et al., Cell 58: 293–303 (1989). This has proved not to be the case with the TRAs of this invention. These papers also demonstrated that peptides derived from the tum⁻ antigen are presented by the $L^d$ molecule for recognition by CTLs. P91A is presented by $L^d$, P35 by $D^d$ and P198 by $K^d$.

Prior patent applications PCT/US92/04354, U.S. Ser. No. 07/807,043, now issued as U.S. Pat. No. 5,342,774; 07/764,365 now abandoned; 07/728,838, now abandoned, and 07/707,702, now abandoned all of which are incorporated by reference, describe inventions involving, inter alia, genes and other nucleic acid molecules which code for various TRAPs, which are in turn processed to tumor rejection antigen, or "TRAs".

The genes are useful as a source for the isolated and purified tumor rejection antigen precursor and the TRA themselves, either of which can be used as an agent for treating the cancer for which the antigen is a "marker", as well as in various diagnostic and surveillance approaches to oncology, discussed infra. It is known, for example, that tum⁻ cells can be used to generate CTLs which lyse cells presenting different tum⁻ antigens as well as tum⁺ cells. See, e.g., Maryanski et al., Eur. J. Immunol 12: 401 (1982); and Van den Eynde et al., Modern Trends in Leukemia IX (June 1990), the disclosures of which are incorporated by reference. The tumor rejection antigen precursor may be expressed in cells transfected by the gene, and then used to generate an immune response against a tumor of interest.

In the parallel case of human neoplasms, it has been observed that autologous mixed lymphocyte-tumor cell cultures ("MLTC" hereafter) frequently generate responder lymphocytes which lyse autologous tumor cells and do not lyse natural killer targets, autologous EBV-transformed B cells, or autologous fibroblasts (see Anichini et al., Immunol. Today 8: 385–389 (1987)). This response has been particularly well studied for melanomas, and MLTC have been carried out either with peripheral blood cells or with tumor infiltrating lymphocytes. Examples of the literature in this area including Knuth et al., Proc. Natl. Acad. Sci. USA 86: 2804–2802 (1984); Mukherji et al., J. Exp. Med. 158: 240 (1983); Hérin et all, Int. J. Canc. 39: 390–396 (1987); Topalian et al, J. Clin. Oncol 6: 839–853 (1988). Stable cytotoxic T cell clones ("CTLs" hereafter) have been derived from MLTC responder cells, and these clones are specific for the tumor cells. See Mukherji et al., supra, Hérin et all, supra, Knuth et al., supra. The antigens recognized on tumor cells by these autologous CTLs do not appear to represent a cultural artifact, since they are found on fresh tumor cells. Topalian et al., supra; Degiovanni et al., Eur. J. Immunol. 20: 1865–1868 (1990). These observations, coupled with the techniques used herein to isolate the genes for specific murine tumor rejection antigen precursors, have led to the isolation of nucleic acid sequences coding for tumor rejection antigen precursors of TRAs presented on human tumors. It is now possible to isolate the nucleic acid sequences which code for tumor rejection antigen precursors, including, but not being limited to those most characteristic of a particular tumor, with ramifications that are described infra.

Additional work has focused upon the presentation of TRAs by the class of molecules known as human leukocyte antigens, or "HLAs". This work has resulted in several unexpected discoveries regarding the field. Specifically in U.S. patent application Ser. No. 07/938,334, now U.S. Pat. No. 5,405,440 the disclosure of which is incorporated by reference, nonapeptides are taught which are presented by the HLA-A1 molecule. The reference teaches that given the known specificity of particular peptides for particular HLA molecules, one should expect a particular peptide to bind one HLA molecule, but not others. This is important, because different individuals possess different HLA phenotypes. As a result, while identification of a particular peptide as being a partner for a specific HLA molecule has diagnostic and therapeutic ramifications, these are only relevant for individuals with that particular HLA phenotype. There is a need for further work in the area, because cellular abnormalities are not restricted to one particular HLA phenotype, and targeted therapy requires some knowledge of the phenotype of the abnormal cells at issue.

In U.S. patent application Ser. No. 08/008,446, now abandoned filed Jan. 22, 1993 and incorporated by reference, the fact that the MAGE-1 expression product is processed to a second TRA is disclosed. This second TRA is presented by HLA-C10-molecules. The disclosure shows that a given TRAP can yield a plurality of TRAs.

In U.S. patent application Ser. No. 07/994,928, filed Dec. 22, 1992 now abandoned, and incorporated by reference herein, tyrosinase is described as a tumor rejection antigen precursor. This reference discloses that a molecule which is produced by some normal cells (e.g., melanocytes), is processed in tumor cells to yield a tumor rejection antigen that is presented by HLA-A2 molecules.

It was mentioned, supra, that different individuals possess different HLA types. It has also been found that the expression of particular MAGE genes is not always linked to particular disorders, or individuals of particular HLA types. Thus, one cannot state, e.g., that all melanoma patients will express MAGE-1 TRAP nor could one say categorically that MAGE-1 expression is limited to melanoma patients of type HLA-A1. Further, one cannot state that only one type of TRAP is expressed in individuals of a particular HLA type. No rules or guidelines can be pointed to which correlate any of these factors.

Thus, it is not expected that a second TRAP is processed to a TRAP which is presented by HLA-A1 molecules. It has now been found that in addition to MAGE-1, a TRA derived from MAGE-3 TRAP is presented by HLA-A1 molecules. This is shown in examples 37–40, which follow, together with a discussion of the ramifications of this discovery.

These and various other aspects of the invention are elaborated upon in the disclosure which follows.

BRIEF DESCRIPTION OF THE FIGURES

FIGS. 1A and 1B depicts detection of transfectants expressing antigen P815A.

FIG. 9 shows homology of sections of exon 3 from genes mage 1, 2 and 3 (see SEQ ID No. 8, residues 4040–4538; SEQ ID No. 9, residues 2778–3276; and SEQ ID No. 11, residues 352–850).

FIG. 11 presents the data of FIG. 13 in table form.

BRIEF DESCRIPTION OF SEQUENCES

Figure 1A:
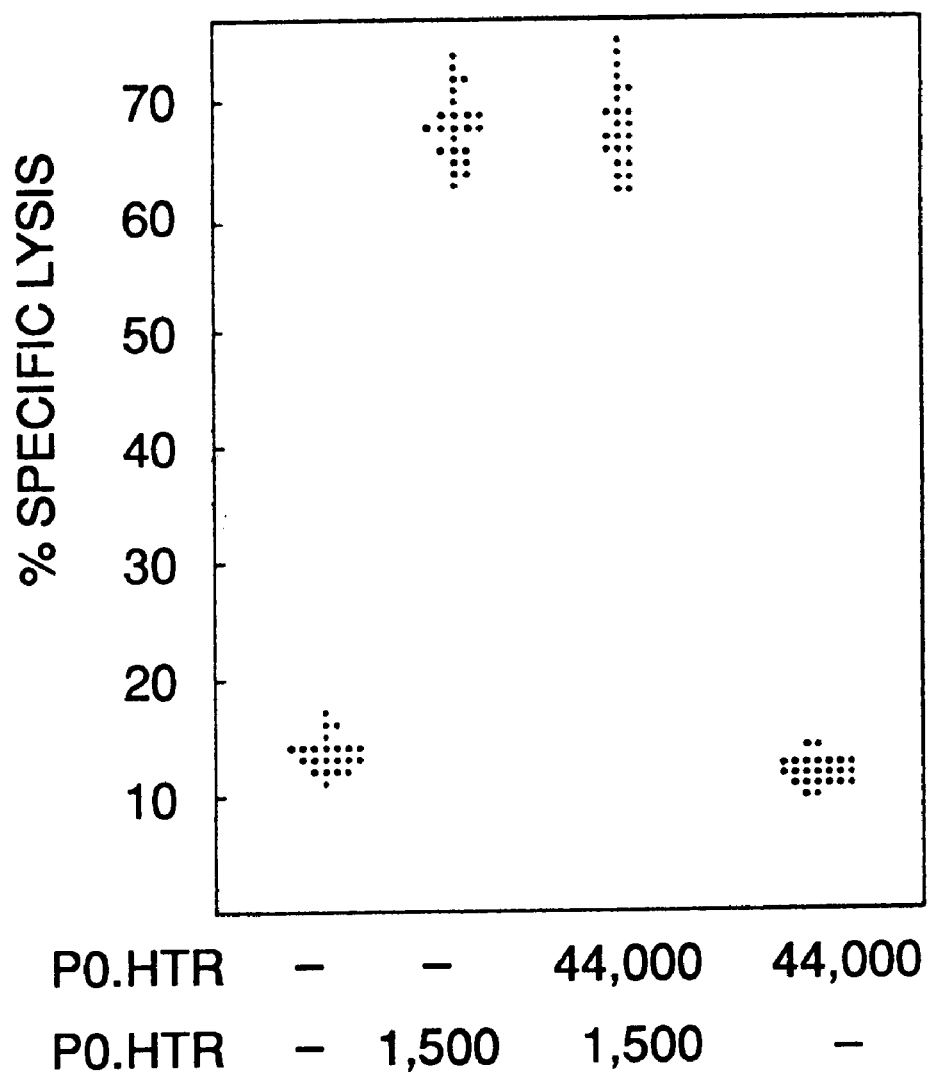

SEQ ID NO: 1 is cDNA for part of gene P1A.

SEQ ID NO: 2 presents coding region of cDNA for gene P1A.

SEQ ID NO: 3 shows non coding DNA for P1A cDNA which is 3' to the coding region of SEQ ID NO: 2.

SEQ ID NO: 4 is the entire sequence of cDNA for P1A.

SEQ ID NO: 5 is the genomic DNA sequence for P1A.

SEQ ID NO: 6 shows the amino acid sequence for the antigenic peptides for P1A TRA. The sequence is for cells which are $A^+ B^+$, i.e., express both the A and B antigens.

SEQ ID NO: 7 is a nucleic acid sequence coding for antigen E.

SEQ ID NO: 8 is a nucleic acid sequence coding for MAGE-1.

SEQ ID NO: 9 is the gene for MAGE-2.

SEQ ID NO: 10 is the gene for MAGE-21.

SEQ ID NO: 11 is cDNA for MAGE-3.

SEQ ID NO: 12 is the gene for MAGE-31.

SEQ ID NO: 13 is the gene for MAGE-4.

SEQ ID NO: 14 is the gene for MAGE-41.

SEQ ID NO: 15 is cDNA for MAGE-4.

SEQ ID NO: 16 is cDNA for MAGE-5.

SEQ ID NO: 17 is genomic DNA for MAGE-51

SEQ ID NO: 18 is cDNA for MAGE-6.

SEQ ID NO: 19 is genomic DNA for MAGE-7.

SEQ ID NO: 20 is genomic DNA for MAGE-8.

SEQ ID NO: 21 is genomic DNA for MAGE-9.

SEQ ID NO: 22 is genomic DNA for MAGE-10.

SEQ ID NO: 23 is genomic DNA for MAGE-11.

SEQ ID NO: 24 is genomic DNA for smage-I.

SEQ ID NO: 25 is genomic DNA for smage-II.

DETAILED DESCRIPTION OF PREFERRED EMBODIMENTS

Many different "MAGE" genes have been identified, as will be seen from the sequences which follow the application. The protocols described in the following examples were used to isolate these genes and cDNA sequences.

"MAGE" as used herein refers to a nucleic acid sequence isolated from human cells. The acronym "smage" is used to describe sequences of murine origin.

When "TRAP" or "TRAs" are discussed herein as being specific to a tumor type, this means that the molecule under consideration is associated with that type of tumor, although not necessarily to the exclusion of other tumor types.

EXAMPLE 1

In order to identify and isolate the gene coding for antigen P815A, gene transfection was used. This approach requires both a source of the gene, and a recipient cell line. Highly transfectable cell line P1.HTR was the starting material for the recipient, but it could not be used without further treatment, as it presents "antigen A", one of four recognized P815 tumor antigens. See Van Pel et al., Molecular Genetics 11: 467–475 (1985). Thus, screening experiments were carried out to isolate cell lines which did not express the antigen and which nonetheless possessed P1.HTR's desirable qualities.

To do this, P1.HTR was screened with CTLs which were specific for each of tumor antigens A, B, C and D. Such CTLs are described by Uyttenhove et al., J. Exp. Med. 157: 1040–1052 (1983).

To carry out the selection, $10^6$ cells of P1.HTR were mixed with $2–4\times10^6$ cells of the CTL clone in a round bottom tube in 2 ml of medium, and centrifuged for three minutes at 150 xg. After four hours at 37° C., the cells were washed and resuspended in 10 ml of medium, following Maryanski et al., Eur. J. Immunol. 12: 406–412 (1982). Additional information on the CTL assay and screening protocol, in general may be found in Boon et al., J. Exp. Med. 152: 1184–1193 (1980), and Maryanski et al., Eur. J. Immunol. 12: 406–412 (1982), the disclosure of which are incorporated by reference.

When these selections were carried out, a cell line variant was found which expressed neither antigen A or B. Additional selections with CTLs specific for antigen C then yielded a variant which also lacked antigen C. Please see FIG. 2 for a summary of the results of these screenings. The variant PO.HTR is negative for antigens A, B and C, and was therefore chosen for the transfection experiments.

The cell line PO.HTR has been deposited in accordance with the Budapest Treaty at the Institute Pasteur Collection Nationale De Cultures De Microorganismes, 28, Rue de Docteur Roux, 75724 Paris France, and has accession number I-1117.

This methodology is adaptable to secure other cell lines which are variants of a cell type which normally presents at least one of the four recognized P815 tumor antigens, i.e., antigens A, B, C and D, where the variants present none of antigens A, B and C. P1.HTR is a mastocytoma cell line, so it will be seen that the protocol enables the isolation of biologically pure mastocytoma cell lines which express none of P815 antigens A, B and C, but which are highly transfectable. Other tumor types may also be screened in this fashion to secure desired, biologically pure cell lines. The resulting cell lines should be at least as transfectable with foreign DNA as is P1.HTR, and should be selected so as to not express a specific antigen.

EXAMPLE 2

Previous work reported by DePlaen et al., Proc. Natl. Acad. Sci. USA 85: 2274–2278 (1988) the disclosure of which is incorporated by reference herein had shown the efficacy of using cosmid library transfection to recover genes coding for tum⁻ antigens.

Selective plasmid and genomic DNA of P1.HTR were prepared, following Wölfel et al., Immunogenetics 26: 178–187 (1987). The transfection procedure followed Corsaro et al., Somatic Cell Molec. Genet 7: 603–616 (1981), with some modification. Briefly, 60 $\mu$g of cellular DNA and 3 $\mu$g of DNA of plasmid pHMR272, described by Bernard et al., Exp. Cell. Biol. 158: 237–243 (1985) were mixed. This plasmid confers hygromycin resistance upon recipient cells, and therefore provides a convenient way to screen for transfectants. The mixed DNA was combined with 940 ul of 1 mM Tris-HCl (pH 7.5), 0.1 mM EDTA; and 310 ul 1 M $CaCl_2$. The solution was added slowly, and under constant agitation to 1.25 ml of 50 mM Hepes, 280 mM NaCl, 1.5 mM $Na_2HPO_4$, adjusted to pH 7.1 with NaOH. Calcium phosphate—DNA precipitates were allowed to form for 30–45 minutes at room temperature. Following this, fifteen groups of P0.HTR cells ($5 \times 10^6$) per group were centrifuged for 10 minutes at 400 g. Supernatants were removed, and pellets were resuspended directly into the medium containing the DNA precipitates. This mixture was incubated for 20 minutes at 37° C., after which it was added to an 80 cm² tissue culture flask containing 22.5 ml DMEM, supplemented with 10% fetal calf serum. After 24 hours, medium was replaced. Forty-eight hours after transfection, cells were collected and counted. Transfected cells were selected in mass culture using culture medium supplemented with hygromycin B (350 ug/ml). This treatment selected cells for hygromycin resistance.

For each group, two flasks were prepared, each containing $8 \times 10^6$ cells in 40 ml of medium. In order to estimate the number of transfectants, $1 \times 10^6$ cells from each group were plated in 5 ml DMEM with 10% fetal calf serum (FCS), 0.4% bactoagar, and 300 ug/ml hygromycin B. The colonies were then counted 12 days later. Two independent determinations were carried out and the average taken. This was multiplied by 5 to estimate the number of transfectants in the corresponding group. Correction had to be made for the cloning efficiency of P815 cells, known to be about 0.3.

EXAMPLE 3

Eight days after transfection as described in example 2, supra, antibiotic resistant transfectants were separated from dead cells, using density centrifugation with Ficoll-Paque. These cells were maintained in non-selective medium for 1 or 2 days. The cells were plated in 96 well microplates (round bottom), at 30 cells/microwell in 200 ul of culture medium. Anywhere from 100–400 microwells were prepared, depending on the number of transfectants prepared. Agar colony tests gave estimates of 500–3000. After 5 days, the wells contained about $6 \times 10^4$ cells and replicate plates were prepared by transferring 1/10 of the wells to microplates which were then incubated at 30° C. One day later, master plates were centrifuged, medium removed, and 750 CTLs against P815 antigen A (CTL-P1:5) were added to each well together with $10^6$ irradiated syngeneic feeder spleen cells in CTL culture medium containing 40 U/ml recombinant human IL-2, and HAT medium to kill stimulator cells. Six days later, plates were examined visually to identify wells where CTLs had proliferated. Where plates showed proliferating microcultures, aliquots of 100 ul of the wells were transferred to another plate containing $^{51}Cr$ labeled P1.HTR target cells ($2 \times 10^3 - 4 \times 10^3$ per well), and chromium release was measured after 4 hours. Replicate microcultures corresponding to those showing high CTL activity were expanded and cloned by limited dilution in DMEM with 10% FCS. Five days later, about 200 clones were collected and screened with the CTL.P1:5 cell line, described supra, in a visual lysis assay. See FIG. 1A for these results.

In these experiments, three of the fifteen groups of transfectants yielded a few positive microcultures. These microcultures were tested for lytic activity against P1.HTR, as described supra. Most of the microcultures where proliferation was observed showed lytic activity. This activity was well above background, as shown in FIG. 1B. This figure summarizes data wherein two groups of cells (groups "5" and "14"), 400 and 300 microwells were seeded with 30 hygromycin resistant transfected cells. Amplification and duplication of the microcultures was followed by addition of anti-A CTL P1:5. Six days later, lytic activity against P1.HTR was tested. In the figure, each point represents lytic activity of a single microculture.

Duplicate microcultures corresponding to several positive wells were subcloned, and more than 1% of the subclones were found to be lysed by anti-A CTL. Thus, three independent transfectants expressing P815A were obtained from 33,000 hygromycin resistant transfectants. One of these lines, referred to hereafter as P1A.T2 was tested further.

Figure 2:
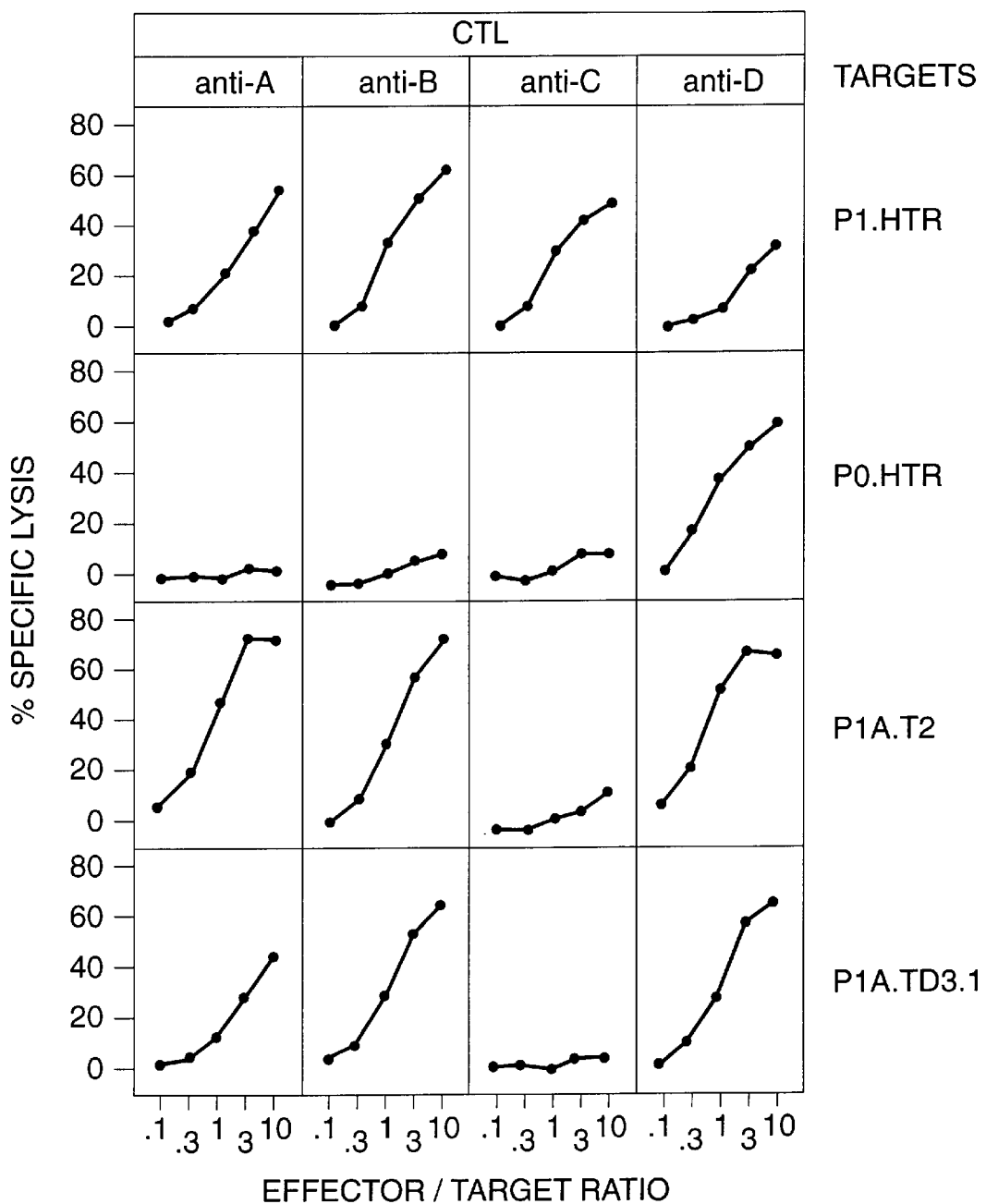
FIG. 2 shows the sensitivity of clones P1.HTR, PO.HTR, genomic transfectant P1A.T2 and cosmid transfectant P1A.TC3.1 to lysis by various CTLs, as determined by chromium release assays.

The relevant antigen profile of P1A.T2 is shown in FIG. 2, this being obtained via anti-CTL assays of the type described supra.

EXAMPLE 4

The CTL assays carried out for P1A.T2 demonstrated that it presented antigen A ("P815A"), and therefore had received the gene from P1.HTR. To that end, this cell line was used as a source for the gene for the antigen precursor in the following experiments.

Prior work had shown that genes coding for tum⁻ antigens could be recovered directly from transfectants obtained with a cosmid library. See DePlaen et al., Proc. Natl. Acad. Sci. USA 85: 2274–2278 (1988). This procedure was followed for recovery of the P815 gene.

Total genomic DNA of P1A.T2 was partially digested with restriction endonuclease Sau 3A1, and fractionated by NaCl density gradient ultracentrifugation to enrich for 35–50 kb DNA fragments, following Grosveld et al., Gene 10: 6715–6732 (1982). These fragments were ligated to cosmid arms of C2RB, described by Bates et al., Gene 26: 137–146 (1983), the disclosure of which is incorporated by reference. These cosmid arms had been obtained by cleavage with SmaI and treatment with calf intestinal phosphatase, followed by digestion with BamHI. Ligated DNA was packaged into lambda phage components, and titrated on E. coli ED 8767, following Grosveld et al., supra. Approximately $9 \times 10^5$ ampicillin resistant colonies were obtained per microgram of DNA insert.

The cosmid groups were amplified by mixing 30,000 independent cosmids with 2 ml of ED 8767 in 10 mM $MgCl_2$, incubated 20 minutes at 37° C., diluted with 20 ml of Luria Bertani ("LB") medium, followed by incubation for one hour. This suspension was titrated and used to inoculate 1 liter of LB medium in the presence of ampicillin (50 ug/ml). At a bacterial concentration of $2\times10^8$ cells/ml ($OD_{600}$=0.8), a 10 ml aliquot was frozen, and 200 ug/ml chloramphenicol was added to the culture for overnight incubation. Total cosmid DNA was isolated by alkaline lysis procedure, and purified on CsCl gradient.

In these experiments, a library of 650,000 cosmids was prepared. The amplification protocol involved the use of 21 groups of approximately 30,000 cosmids.

EXAMPLE 5

Using the twenty-one groups of cosmids alluded to supra, (60 ug) and 4 ug of pHMR272, described supra, groups of $5\times10^6$ PO.HTR cells were used as transfectant hosts. Transfection was carried out in the same manner as described in the preceding experiments. An average of 3000 transfectants per group were tested for antigen presentation, again using CTL assays as described. One group of cosmids repeatedly yielded positive transfectants, at a frequency of about 1/5,000 drug resistant transfectants. The transfectants, as with P1A.T2, also showed expression of both antigen A and B. The pattern of expression of transfectant P1A.TC3.1 is shown in FIG. 2.

EXAMPLE 6

As indicated in Example 5, supra, three independent cosmid transfected cells presenting P815A antigen were isolated. The DNA of these transfectants was isolated and packaged directly with lambda phage extracts, following DePlaen et al., Proc. Natl. Acad. Sci. USA 85: 2274–2278 (1988). The resulting product was titrated on *E. coli* ED 8767 with ampicillin selection, as in Example 5. Similarly, amplification of the cosmids and transfection followed Example 5, again using PO.HTR.

High frequencies of transfection were observed, as described in Table 1, which follows:

TABLE 1

Transfer of the expression of antigen P815A by cosmids obtained by direct packaging

| Transfectant obtained with the cosmid library | No. of cosmids obtained by direct packaging of 0.5 μg of DNA | No. of transfectants expressing P815A/ no. of HmB$^r$ transfectants |
|---|---|---|
| TC3.1 | 32 | 87/192 |
| TC3.2 | 32000 | 49/384 |
| TC3.3 | 44 | 25/72 |

The cosmids were analyzed with restriction enzymes and it was found that directly packaged transfectant P1A.TC3.1 contained 32 cosmids, 7 of which were different. Each of these 7 cosmids was transfected into PO.HTR, in the manner described supra, and again, following the protocols described above, transfectants were studied for presentation of P815A. Four of the cosmid transfectants showed P815A presentation and, as with all experiments described herein, P815B was co-expressed.

Of the four cosmids showing presentation of the two antigens, cosmid C1A.3.1 was only 16.7 kilobases long, and was selected for further analysis as described infra.

Figure 3:
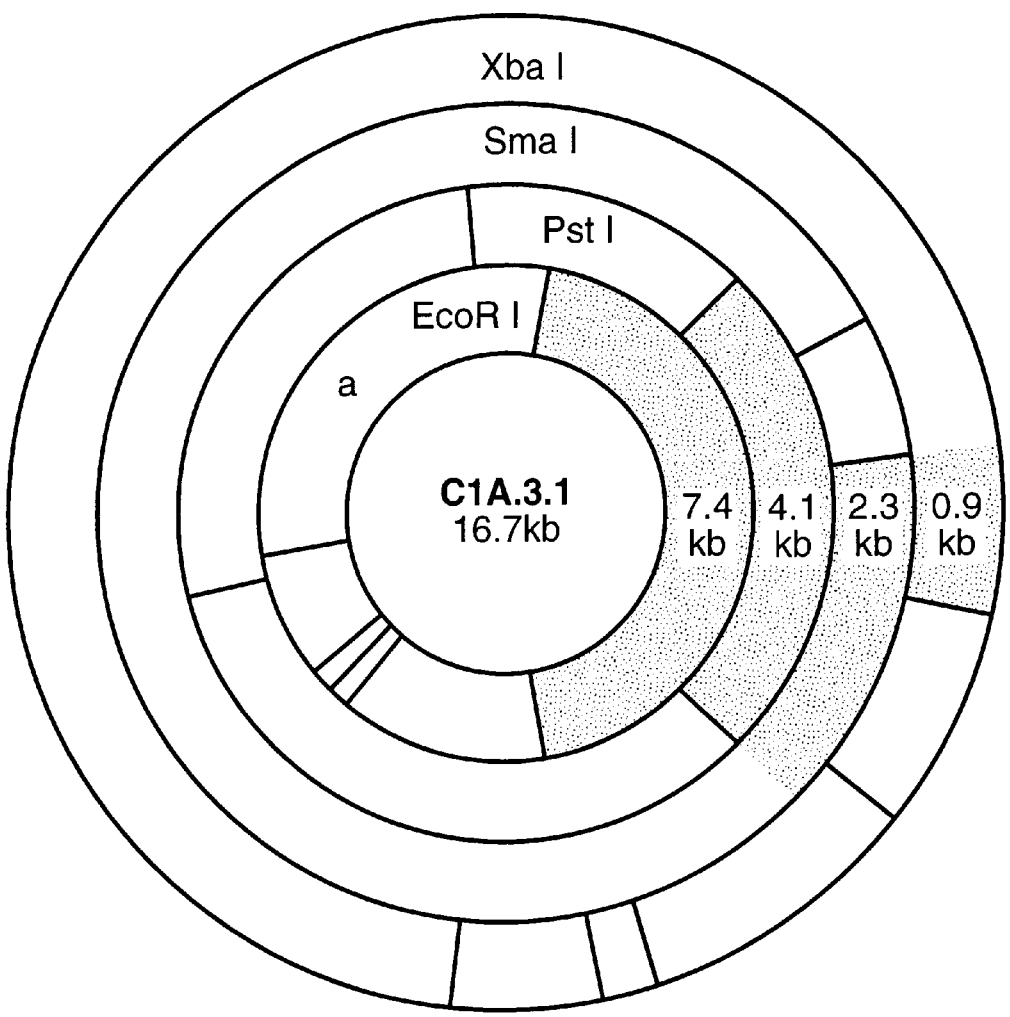
FIG. 3 is a restriction map of cosmid C1A.3.1.

The cosmid C1A.3.1 was subjected to restriction endonuclease analysis, yielding the map shown in FIG. 3.

All EcoRI fragments were transfected, again using the above described protocols, and only the 7.4 kilobase fragment produced a transfectant that anti-A CTLs could lyse. Similar experiments were carried out on the PstI fragments, and only a 4.1 kb fragment fully contained within the 7.4 kb EcoRI fragment produced lysable transfectants.

This fragment (i.e., the 4.1 kb PstI fragment), was digested with SmaI, giving a 2.3 kb fragment which also yielded host cells presenting antigens A and B after transfection. Finally, a fragment 900 bases long, secured with SmaI/XbaI, also transferred expression of the precursors of these two antigens, i.e., the transfected host cell presented both antigen A and antigen B.

EXAMPLE 7

The 900 base fragment described above was used as a probe to detect the expression of the P815A gene in parent cell line P1.HTR. To accomplish this, total cellular RNA was first isolated using the guanidine-isothiocyanate procedure of Davis et al., *Basic Methods In Molecular Biology* (Elseview Science Publishing Co, New York) (1986). The same reference was the source of the method used to isolate and purify polyA$^+$ mRNA using oligodT cellulose column chromatography.

Samples were then subjected to Northern Blot analysis. RNA samples were fractionated on 1% agarose gels containing 0.66 M formaldehyde. The gels were treated with 10×SSC (SSC: 0.15 M NaCl; 0.015 M sodium citrate, pH 7.0) for 30 minutes before overnight blotting on nitrocellulose membranes. These were baked for two hours at 80° C., after which the membranes were prehybridized for 15 minutes at 60° C. in a solution containing 10% dextran sulfate, 1% SDS and 1 M NaCl. Hybridization was then carried out using denatured probe (the 900 base fragment), together with 100 ug/ml salmon sperm DNA.

Figure 4:
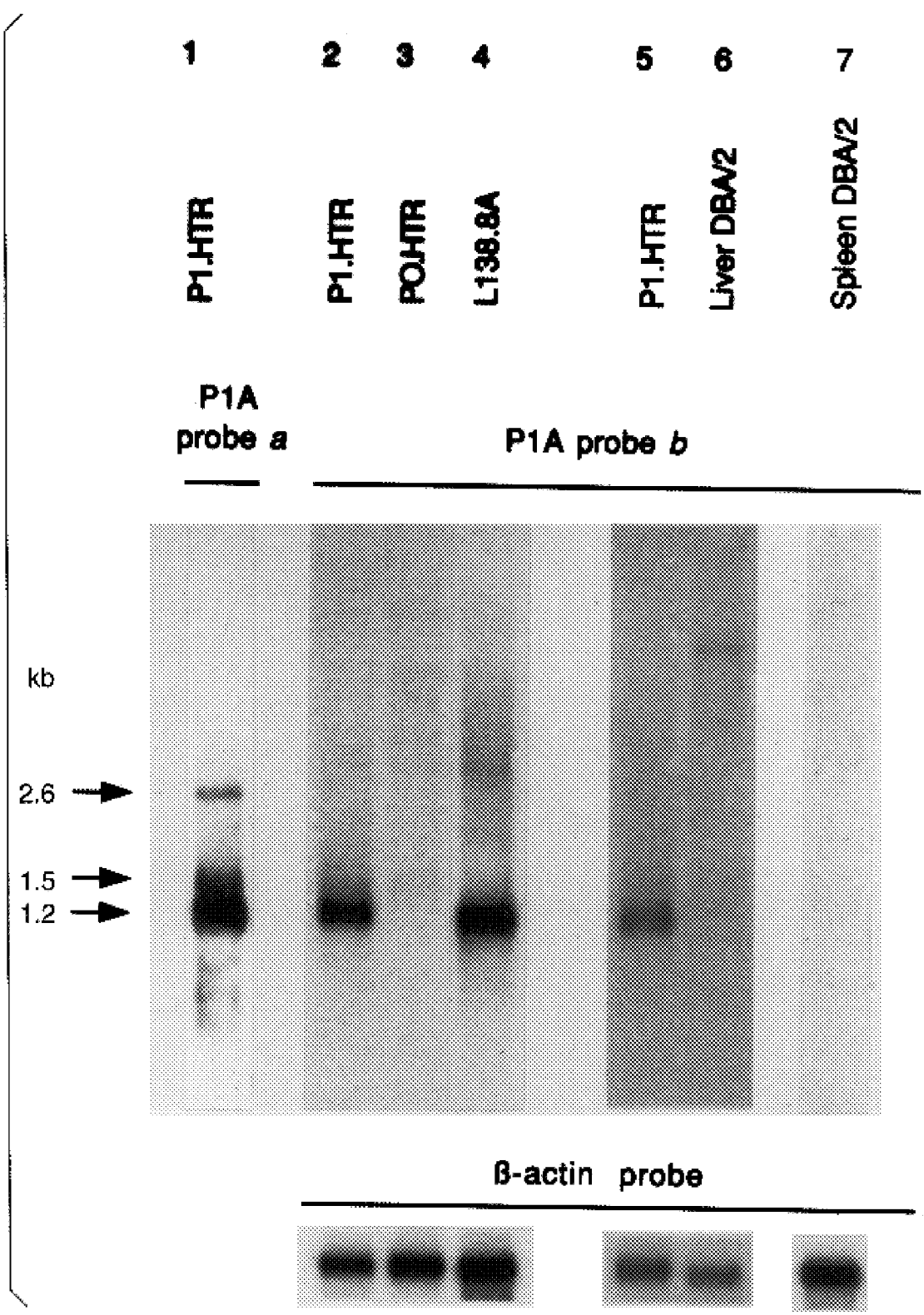
FIG. 4 shows Northern Blot analysis of expression of gene P1A.

When this protocol was carried out using P1.HTR poly A$^+$ RNA, a band of 1.2 kb and two fainter bands were identified, as shown in FIG. 4, lane 1 (6 ug of the RNA).

The same probe was used to screen a cDNA library, prepared from poly-A$^+$ RNA from the cell line. This yielded a clone with a 1 kb insert, suggesting a missing 5' end. The Northern blots for the cDNA are not shown.

Hybridization experiments in each case were carried out overnight at 60° C. The blots were washed twice at room temperature with 2×SSC and twice at 60° C. with 2×SSC supplemented with 1% SDS.

The foregoing experiments delineated the DNA expressing the P815A antigen precursor sufficiently to allow sequencing, using the well known Sanger dideoxy chain termination method. This was carried out on clones generated using a variety of restriction endonucleases and by specific priming with synthetic oligonucleotide primers. The results for exons of the gene are set forth in sequence id no: 4.

EXAMPLE 8

The Northern analysis described supra suggested that the 5' end of the cDNA was missing. To obtain this sequence, cDNA was prepared from P1.HTR RNA using a primer corresponding to positions 320–303. The sequence was then amplified using the polymerase chain reaction using a 3' primer corresponding to positions 286–266 and a 5' primer described by Frohman et al., Proc. Natl. Acad. Sci. USA 85:

8998–9002 (1988). A band of the expected size (270 bases) was found, which hybridized to the 900 bp SmaI/XbaI fragment described supra on a Southern blot. Following cloning into m13tg 130 λ tg 131, the small, 270 bp fragment was sequenced. The sequence is shown in sequence id no: 1.

EXAMPLE 9

Following the procurement of the sequences described in Examples 7 and 8 and depicted in seq id no: 4, a 5.7 kb region of cosmid C1A.3.1 was sequenced. This fragment was known to contain the 900 base fragment which expressed P815A in transfectants. This experiment permitted delineation of introns and exons, since the cosmid is genomic in origin.

Figure 5:
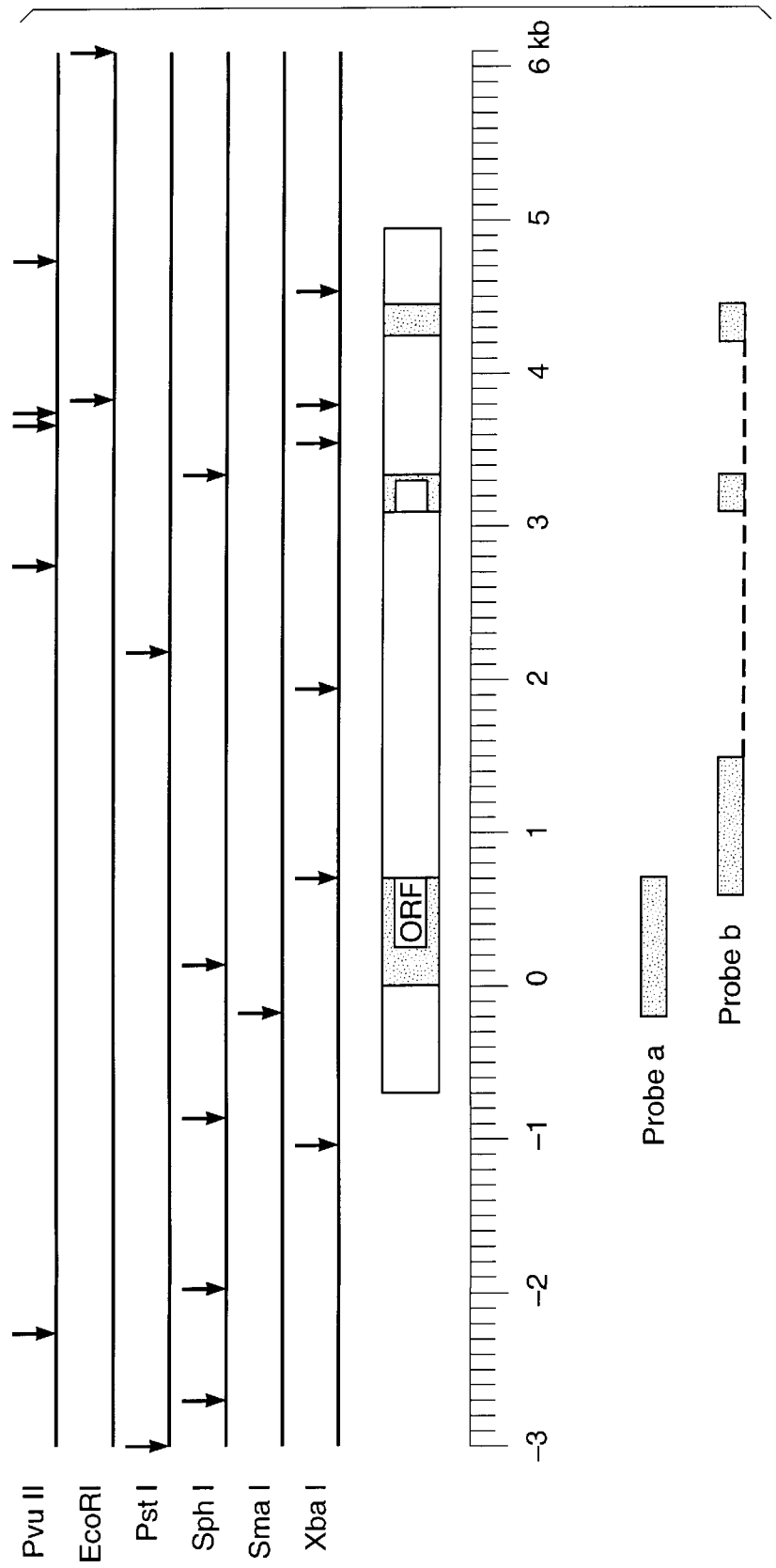
FIG. 5 sets forth the structure of gene P1A with its restriction sites.
Figure 6:
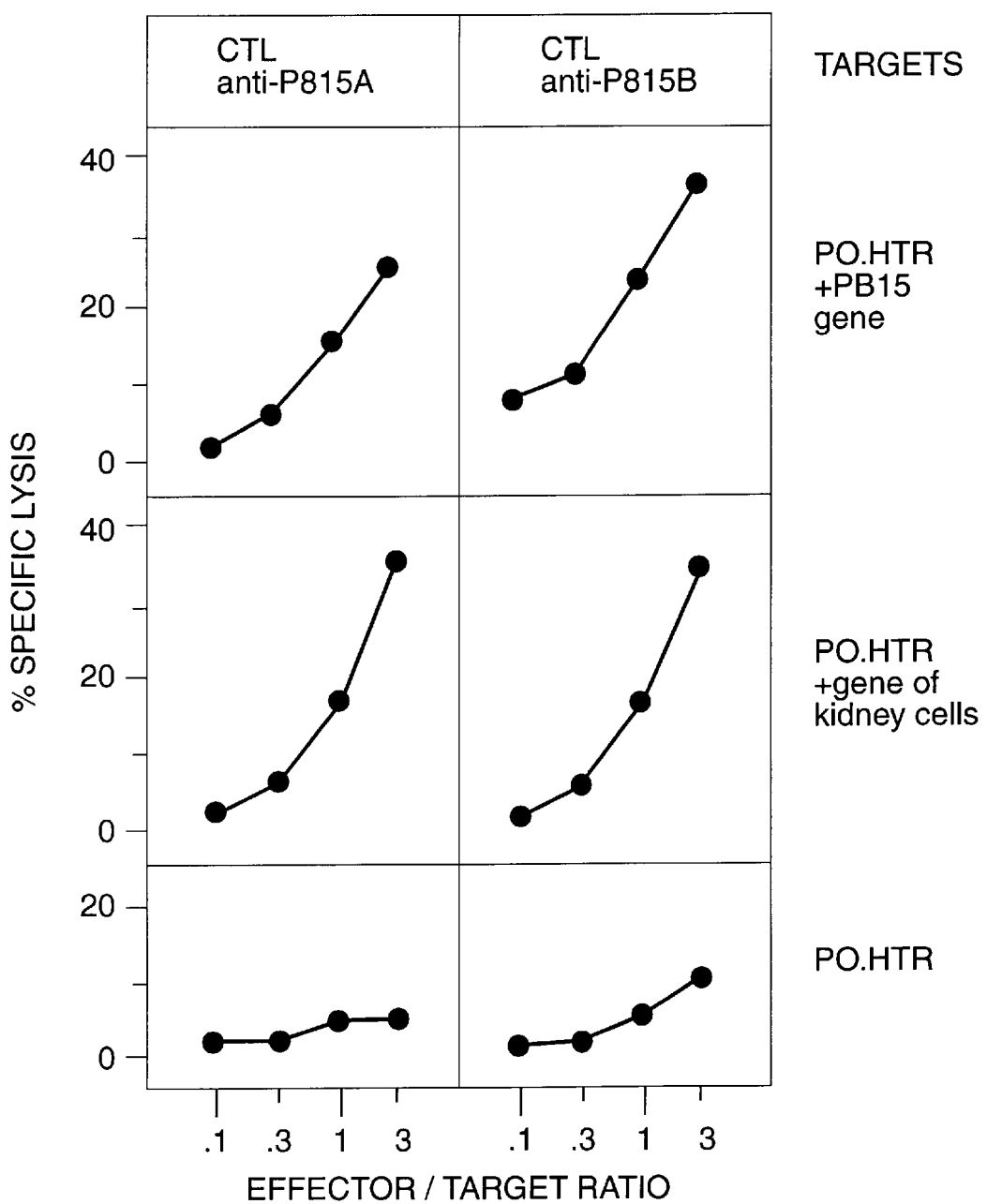
FIG. 6 shows the results obtained when cells were transfected with the gene from P1A, either isolated from P815 or normal cells and then tested with CTL lysis.

The delineated structure of the gene is shown in FIG. 5. Together with seq id no: 4, these data show that the gene for the antigen precursor, referred to as "P1A" hereafter, is approximately 5 kilobases long and contains 3 exons. An ORF for a protein of 224 amino acids starts in exon 1, ending in exon 2. The 900 base pair fragment which transfers expression of precursors for antigens A and B only contains exon 1. The promoter region contains a CAAT box, as indicated in seq. id no: 1, and an enhancer sequence. This latter feature has been observed in promoters of most MHC class I genes, as observed by Geraghty et al., J. Exp. Med 171: 1–18 (1990); Kimura et al., Cell 44: 261–272 (1986).

A computer homology search was carried out, using program FASTA with K-triple parameters of 3 and 6, as suggested by Lipman et al., Science 227: 1435–1441 (1985), and using Genbank database release 65 (October 1990). No homology was found except for a stretch of 95 bases corresponding to part of an acid region coded by exon 1 (positions 524–618), which is similar to sequences coding for acidic regions in mouse nucleolar protein NO38/B23, as described by Bourbon et al., Mol. Biol. 200: 627–638 (1988), and Schmidt-Zachmann et al., Chromosoma 96: 417–426 (1988). Fifty six of 95 bases were identical. In order to test whether these homologies were the reason for cross hybridizing, experiments were carried out using a mouse spleen cDNA library screened with the 900 base fragment. cDNA clones corresponding closely to the sizes of the cross hybridizing bands were obtained. These were partially sequenced, and the 2.6 kb cDNA was found to correspond exactly to reported cDNA sequence of mouse nucleolin, while the 1.5 kb cDNA corresponded to mouse nucleolar protein NO38/B23.

Analysis of the nucleotide sequence of the gene, referred to as "P1A" hereafter, suggests that its coded product has a molecular mass of 25 kd. Analysis of the sequence id no: 4 shows a potential nuclear targeting signal at residues 5–9 (Dingwall et al., Ann. Rev. Cell Biol. 2: 367–390 (1986)), as well as a large acidic domain at positions 83–118. As indicated supra, this contains the region of homology between P1A and the two nucleolar proteins. A putative phosphorylation site can be found at position 125 (serine). Also, a second acidic domain is found close to the C-terminus as an uninterrupted stretch of 14 glutamate residues. A similar C-terminal structure has been found by Kessel et al. Proc. Natl. Acad. Sci. USA 84: 5306–5310 (1987), in a murine homeodomain protein having nuclear localization.

In studies comparing the sequence of gene P1A to the sequences for P91A, 35B and P198, no similarities were found, showing that P1A is indicative of a different class of genes and antigens.

EXAMPLE 10

With the P1A probe and sequence in hand, investigations were carried out to determine whether the gene present in normal tissue was identical to that expressed by the tumor. To do this, phage libraries were prepared, using lambda zapII 10 and genomic DNA of DBA2 murine kidney cells. P1A was used as a probe. Hybridization conditions were as described supra, and a hybridizing clone was found. The clone contained exons one and two of the P1A gene, and corresponded to positions −0.7 to 3.8 of FIG. 5. Following localization of this sequence, PCR amplification was carried out to obtain the sequence corresponding to 3.8 to 4.5 of FIG. 5.

Sequence analysis was carried out, and no differences were found between the gene from normal kidneys and the P1A gene as obtained from the P815 tumor cells.

Figure 7:
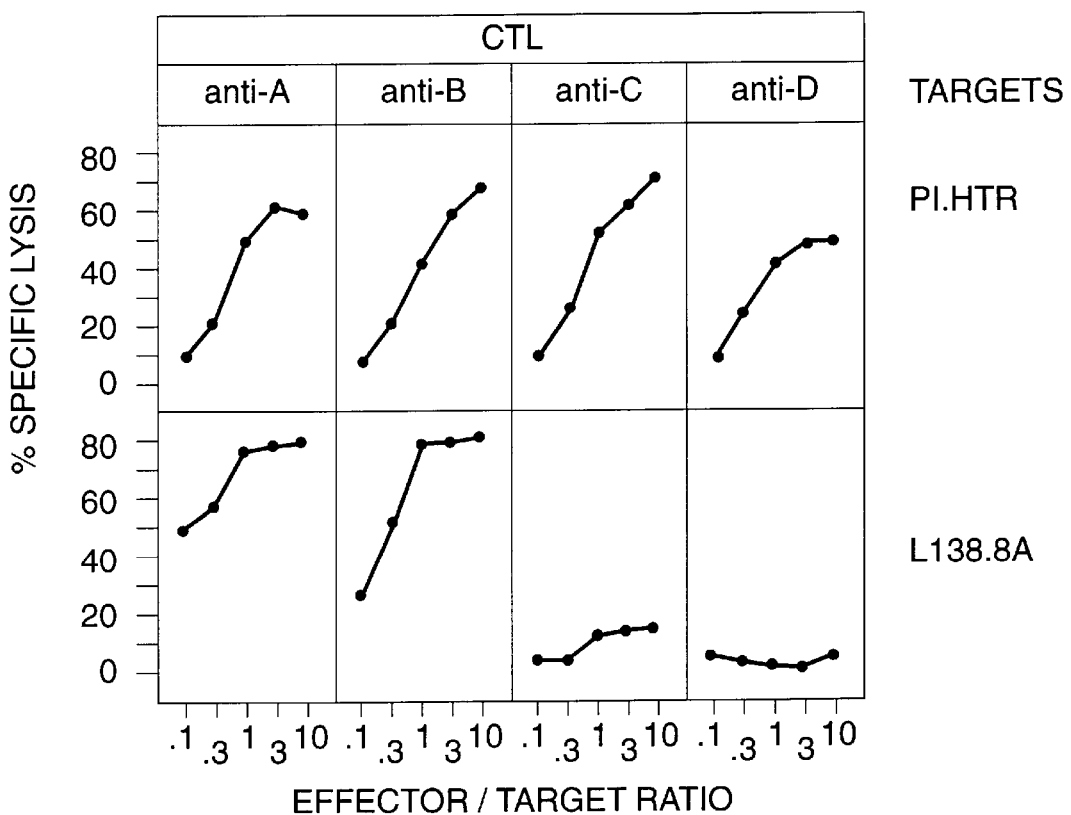
FIG. 7 shows lytic studies using mast cell line L138.8A.

In further experiments, the gene as found in DBA/2 kidney cells was transfected into PO.HTR, as described supra. These experiments, presented pictorially in FIG. 7, showed that antigens A and B were expressed as efficiently by the kidney gene isolated from normal kidney cells as with the P1A gene isolated from normal kidney cells.

These experiments lead to the conclusion that the gene coding for the tumor rejection antigen precursor is a gene that does not result from a mutation; rather, it would appear that the gene is the same as one present in normal cells, but is not expressed therein. The ramifications of this finding are important, and are discussed infra.

In studies not elaborated upon herein, it was found that variants of the gene were available. Some cells were "P1A⁻ B⁺", rather than the normal "P1A". The only difference between these is a point mutation in exon 1, with the 18th triplet coding for Ala in the variant instead of Val.

EXAMPLE 11

Additional experiments were carried out with other cell types. Following the protocols described for Northern blot hybridizations supra, RNA of normal liver and spleen cells was tested to determine if a transcript of the PIA gene could be found. The Northern blot data are presented in FIG. 4 and, as can be seen, there is no evidence of expression.

The murine P815 cell line from which P1A was isolated is a mastocytoma. Therefore, mast cell lines were studied to determine if they expressed the gene. Mast cell line MC/9, described by Nabel et al., Cell 23: 19–28 (1981), and short term cultures of bone marrow derived mast cells were tested in the manner described supra (Northern blotting), but no transcript was found. In contrast when a Balb/C derived IL-3 dependent cell line L138.8A (Hultner et al., J. Immunol. 142: 3440–3446 (1989)) was tested, a strong signal was found. The mast cell work is shown in FIG. 4.

Figure 8:
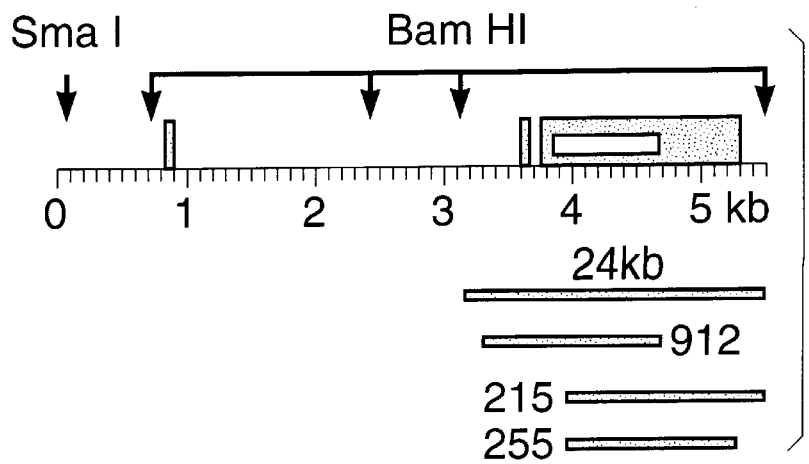
FIG. 8 is a map of subfragments of the 2.4 kb antigen E fragment sequence which also express the antigen.

It is known that both BALB/C and DBA/2 mice share H-$2^d$ haplotype, and thus it was possible to test sensitivity to lysis using the CTLs described supra. FIG. 8 shows these results, which essentially prove that anti-A and anti-B CTLs lysed the cells strongly, whereas anti-C and anti-D lines did not.

Further tests were carried out on other murine tumor cell lines, i.e., teratocarcinoma cell line PCC4 (Boon et al., Proc. Natl. Acad. Sci. USA 74: 272–275 (1977), and leukemias LEC and WEH1-3B. Expression could not be detected in any of these samples.

EXAMPLE 12

The actual presentation of the P1A antigen by MHC molecules was of interest. To test this, cosmid C1A.3.1 was transfected into fibroblast cell line DAP, which shows phenotype H-$2^k$. The cell lines were transfected with genes expressing one of the $K^d$, $D^d$, and $L^d$ antigen. Following transfection with both the cosmid and the MHC gene, lysis with CTLs was studied, again as described supra. These studies, summarized in Table 2, show that $L^d$ is required for presentation of the P1A antigens A and B.

TABLE 2

H-2-restriction of antigens P815A and P815B

| | No. of clones lysed by the CTL/no. of HmB$^r$ clones" | |
|---|---|---|
| Recipient cell* | CTL anti-A | CTL anti-B |
| DAP (H-2$^k$) | 0/208 | 0/194 |
| DAP + K$^d$ | 0/165 | 0/162 |
| DAP + D$^d$ | 0/157 | 0/129 |
| DAP + L$^d$ | 25/33 | 15/20 |

*Cosmid C1A.3.1 containing the entire P1A gene was transfected in DAP cells previously transfected with H-2$^d$ class I genes as indicated.
"Independent drug-resistant colonies were tested for lysis by anti-A or anti-B CTL in a visual assay.

The observation that one may associate presentation of a tumor rejection antigen with a particular MHC molecule was confirmed in experiments with human cells and HLA molecules, as elaborated upon infra.

EXAMPLE 13

Using the sequence of the P1A gene as well as the amino acid sequence derivable therefrom, antigenic peptides which were A$^+$ B$^+$ (i.e., characteristic of cells which express both the A and B antigens), and those which are A$^-$B$^+$ were identified. The peptide is presented in FIG. 10. This peptide when administered to samples of PO.HTR cells in the presence of CTL cell lines specific to cells presenting it, led to lysis of the PO.HTR cells, lending support to the view that peptides based on the product expressed by the gene can be used as vaccines.

EXAMPLE 14

The human melanoma cell line referred to hereafter as MZ2-MEL is not a clonal cell line. It expresses four stable antigens recognized by autologous CTLs, known as antigens "D, E, F, and A". In addition, two other antigens "B" and "C" are expressed by some sublines of the tumor. CTL clones specific for these six antigens are described by Van den Eynde et al., Int. J. Canc. 44: 634–640 (1989). Among the recognized subclones of MZ2-MEL are MEL.43, MEL3.0 and MEL3.1. (Van den Eynde et al., supra). Cell line MEL3.1 expresses antigen E, as determined by CTL studies as described for P815 variants, supra, so it was chosen as a source for the nucleic acid sequence expressing the antigen precursor.

In isolating the pertinent nucleic acid sequence for a tumor rejection antigen precursor, the techniques developed supra, showed that a recipient cell is needed which fulfills two criteria: (i) the recipient cell must not express the TRAP of interest under normal conditions, and (ii) it must express the relevant class I HLA molecule. Also, the recipient cell must have a high transfection frequency, i.e., it must be a "good" recipient.

In order to secure such a cell line, the clonal subline ME3.1 was subjected to repeated selection with anti-E CTL 82/30 as described by Van den Eynde, supra. The repeated cycles of selection led to isolation of subclone MZ2-MEL-2.2 isc E$^-$. This subclone is also HPRT$^-$, (i.e., sensitive to HAT medium: $10^{-4}$ M hypoxanthine, $3.8 \times 10^{-7}$ aminopterine, $1.6 \times 10^{-5}$ M 2-deoxythymidine). The subclone is referred to as "MEL-2.2" for simplicity hereafter.

EXAMPLE 15

The genomic DNA of MEL3.0 was prepared following Wölfel et al., Immunogenetics 26: 178–187 (1987), the disclosure of which is incorporated by reference. The plasmid pSVtkneoβ, as described by Nicolas et al., Cold Spring Harb., Conf. Cell Prolif. 10: 469–485 (1983) confers geneticin resistance, so it can be used as a marker for cotransfection, as it was in this experiment.

Following a procedure similar but not identical to that of Corsao et al., Somatic Cell Molec. Genet 7: 603–616 (1981), total genomic DNA and the plasmid were cotransfected. The genomic DNA (60 µg) and plasmid DNA (6 µg) were mixed in 940 µl of 1 mM Tris-HCl (pH 7.5), 0.1 mM EDTA, after which 310 µg. of 1M $CaCl_2$ was added. This solution was slowly added, under constant agitation, to 1.25 ml of 2×HBS (50 mM HEPES, 280 mM NaCl 1.5 mM $Na_2HPO_4$, adjusted to pH 7.1 with NaOH). The calcium phosphate DNA precipitates were allowed to form for 30–45 minutes at room temperature, after which they were applied to 80 cm$^2$ tissue culture flasks which had been seeded 24 hours previously with $3 \times 10^6$ MEL2.2 cells, in 22.5 ml of melanoma culture medium (Dulbecco's Modified Eagle's Medium) supplemented with 10% fetal calf serum. After 24 hours, the medium was replaced. Forty eight hours after transfection, the cells were harvested and seeded at $4 \times 10^6$ cells per 80 cm$^2$ flask in melanoma culture medium supplemented with 2 mg/ml of geneticin. The geneticin serves as a selection marker.

EXAMPLE 16

Thirteen days after transfection, geneticin-resistant colonies were counted, harvested, and cultured in nonselective medium for 2 or 3 days. Transfected cells were then plated in 96-well microplates at 200 cells/well in 200 ul of culture medium with 20% fetal calf serum (FCS) in order to obtain approximately 30 growing colonies per well. The number of microcultures was aimed at achieving redundancy, i.e., such that every independent transfectant should be represented at least four times.

After 10 days, wells contained approximately $6 \times 10^4$ cells. These cells were detached, and ⅓ of each microculture was transferred to a duplicate plate. After 6 hours, i.e., after readherence, medium was removed and 1500 anti-E CTL (CTL 82/30), were added to each well in 100 µl of CTL culture medium with 35 U/ml of IL-2. One day later, the supernatant (50 µg) was harvested and examined for TNF concentration, for reasons set forth in the following example.

EXAMPLE 17

The size of the mammalian genome is $6 \times 10^6$ kb. As the average amount of DNA integrated in each drug-resistant transfectant was expected to be about 200 kb, a minimum of 30,000 transfectants would need to be examined to ascertain whether antigen E had been transfected. Prior work with murine cells had shown that when a CTL stimulation assay was used, groups containing only 3% of cells expressing the antigen of interested could be identified. This should reduce the number of assays by a factor of 30. While an anti-E CTL assay, as described supra, in mixed E$^+$/E$^-$ cells was helpful, it was not sufficient in that consistent results could not be obtained.

As a result, an alternative test was devised. Stimulation of CTLs was studied by release of tumor necrosis factor ("TNF") using well known methodologies which need not be repeated here. As described in Example 15, 1500 CTL 82/30 cells had been added per well of transfectants. These CTLs were collected 6 days after stimulation. As indicated supra, after ⅓ of the cells in each well had been removed and the remaining ⅔ ($4\times10^4$) had readhered, the CTLs and IL-2 were added thereto. The 50 µl of supernatant was removed 24 hours later and transferred to a microplate containing $3\times10^4$ W13 (WEHI-164 clone 13; Espevik et al., J. Immunol. Meth. 95: 99–105 (1986)) cells in 50 µl of W13 culture medium (RPMI-1640, supplemented with L-arginine (116 mg/l), L-asparagine (36 mg/l), L-glutamine (216 mg/l), and 10% FCS supplemented with 2 µg of actinomycin D at 37% in an 8% $CO_2$ atmosphere. The cell line W13 is a mouse fibrosarcoma cell line sensitive to TNF. Dilutions of recombinant TNF-β in RPMI 1640 were added to target cell controls.

The W13 cultures were evaluated after 20 hours of incubation, and dead cell percentage was measured using an adaptation of the colorimetric assay of Hansen et al., J. Immunol. Meth. 119: 203–210 (1989). This involved adding 50 ml of (3-(4,5-dimethylthiazol-2-yl)-2,5-diphenyl tetrazolium bromide at 2.5 mg/ml in PBS, followed by two hours of incubation at 37° C. Dark blue formazan crystals were dissolved by adding 100 µl of lysis solution (1 volume N,N dimethyl formamide mixed at 37° C. with two volumes of water containing 30% (w/v) sodium dodecyl sulphate, at pH 4.7 from 1.6% acetic acid and 2.5% 1N HCl). Plates were incubated at 37° C. overnight, and ODs were taken at 570 nm using 650 nm as control. Dead cell percentage was determined via the formula:

$$100\times\left[1-\frac{100-(OD_{570} \text{ sample well})}{OD_{570} \text{ well + medium}}\right]$$

following Espevik et al., J. Immunol. Meth. 95: 99–105 (1986). The results showed that even when the ratio of $E^+/E^-$ cells was as low as ⅟45, significant production of TNF was observed, thus showing active CTLs. This led to the decision to test the drug resistant transfectants in groups of 30.

EXAMPLE 18

Cells were tested for TNF production as discussed in Example 17, supra. A total of 100 groups of $E^-$ cells ($4\times10^6$ cells/group) were tested following transfection, and $7\times10^4$ independent geneticin resistant transfectants were obtained, for an average of 700 per group. only one group of transfected cells led to a microculture which caused anti-E antigen CTL clone 82/30 to produce TNF. Of 300 clones tested, 8 were positive. These clones were then tested for lysis by anti-E CTL, using the standard $^{51}$Cr release assay, and were found to be lysed as efficiently as the original $E^+$ cell line. The transfectant E.T1, discussed herein, had the same lysis pattern as did MEL2.2 for CTLs against antigens B,C,D and F.

The fact that only one transfectant presented the antigen out of 70,000 geneticin resistance transfectants may at first seem very low, but it is not. The work described supra for P815 showed an average frequency of 1/13,000. Human DNA recipient MEL2.2 appears to integrate 5 times less DNA than P1.HTR.

EXAMPLE 19

Once transfectant E.T1 was found, analysis had to address several questions including whether an $E^+$ contaminant of the cell population was the cause. The analysis of antigen presentation, described supra, shows that E.T1 is $B^-$ and $C^-$, just like the recipient cell MEL2.2. It was also found to be HPRT$^-$, using standard selection procedures. All $E^+$ cells used in the work described herein, however, were HPRT+.

It was also possible that an $E^+$ revertant of MEL2.2 was the source for E.T1. To test this, the observation by Perucho et al., Cell 22: 309–317 (1980), that cotransfected sequences usually integrate together at a single location of recipient genome was employed. If antigen E in a transfectant results from cotransfection with pSVtkneoβ, then sequences should be linked and deletion of the antigen might also delete the neighboring pSVtkneoβ sequences. Wölfel et al., supra, has shown this to be true. If a normally $E^-$ cell is transfected with pSVtkneoβ, then sequences should be linked and deletion of the antigen might also delete the neighboring pSVtkneoβ sequences. If a normally $E^+$ cell transfected with pSVtkneoβ is E.T1, however, "co-deletion" should not take place. To test this, the transfectant E.T1 was subjected to immunoselection with 82/30, as described supra. Two antigen loss variants were obtained, which resisted lysis by this CTL. Neither of these had lost geneticin resistance; however, Southern blot analysis showed loss of several neor sequences in the variants, showing close linkage between the E gene and neo$^r$ gene in E.T1, leading to the conclusion that E.T1 was a transfectant.

EXAMPLE 20

The $E^+$ subclone MZ2-MEL4B was used as a source of DNA for preparation of a cosmid library. This library of nearly 700,000 cosmids was transfected into MZ2-MEL 2.2 cells, following the cosmid transfection protocols described supra.

By packaging the DNA of cosmid transfectants directly into lambda phase components, it is sometimes possible to retrieve cosmids that contain the sequences of interest. This procedure was unsuccessful here, so we rescued the transfected sequence by ligating DNA of the transfectant to appropriate restriction fragments of cosmid vector pTL6. This was tried with two transfectants and was successful with one of them. One cosmid, referred to as B3, was recovered from this experiment, and subjected to restriction endonuclease digestion via XmaI, or by BamHI digestion of a large, 12 kb XmaI transfected fragment. The fragments were cloned into vector pTZ 18R, and then transfected into MEL2.2. Again, TNF production was the measure by which successful transfection was determined. The experiments led to the determination of a gene sequence capable of transfecting antigen E on the 12 kb XmaI fragment, and then on the 2.4 kb fragment of BamHI digestion of the 12 kb segment.

Figure 12:
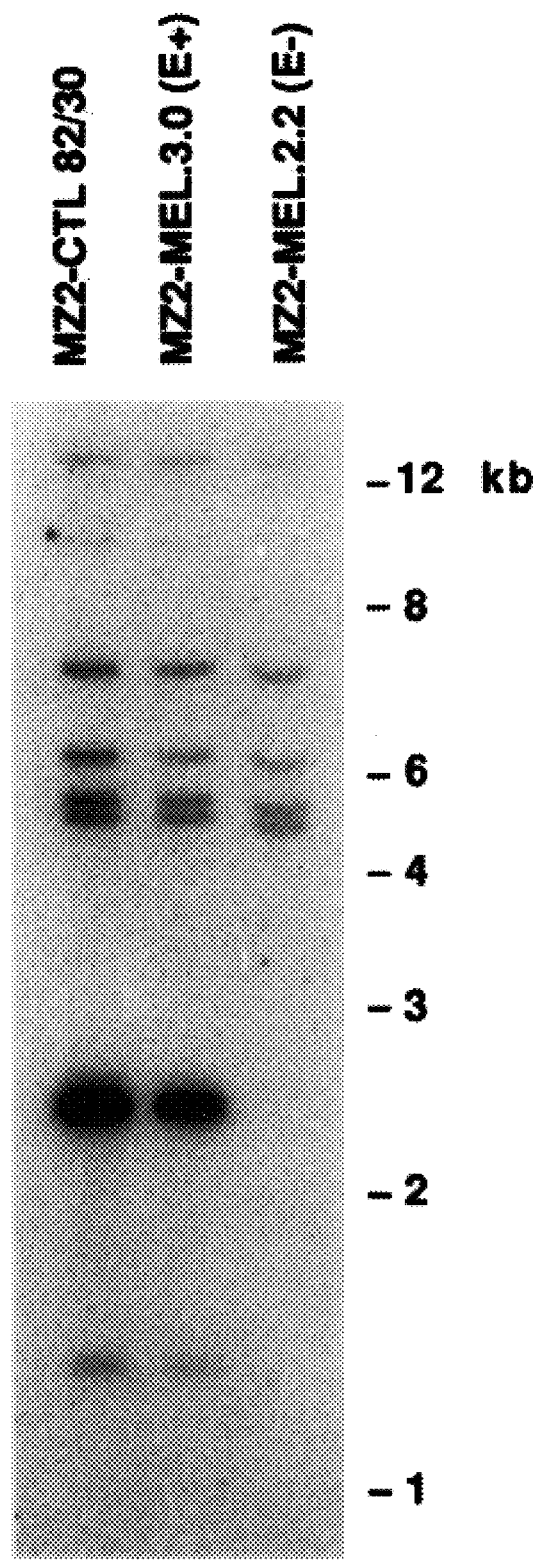
FIG. 12 shows Southern Blot experiments using the various human melanoma cell lines employed in this application.

The 2.4 kb fragment hybridizes with a 2.4 kb fragment from MZ2-MEL and with a T cell clone of patient MZ-2, as determined by Southern Blots (BamHI/SmaI digested DNA). The band is absent from $E^-$ antigen loss variants of MZ2-MEL, as seen in FIG. 12.

The sequence for the E antigen precursor gene has been determined, and is presented herein: (See SEQ ID NO: 7)

```
            |    10       |    20       |    30       |    40       |    50       |    60
   1  GGATCCAGGC  CCTGCCAGGA  AAAATATAAG  GGCCCTGCGT  GAGAACAGAG  GGGGTCATCC    60
  61  ACTGCATGAG  AGTGGGGATG  TCACAGAGTC  CAGCCCACCC  TCCTGGTAGC  ACTGAGAAGC   120
 121  CAGGGCTGTG  CTTGCGGTCT  GCACCCTGAG  GGCCCGTGGA  TTCCTCTTCC  TGGAGCTCCA   180
 181  GGAACCAGGC  AGTGAGGCCT  TGGTCTGAGA  CAGTATCCTC  AGCTCACAGA  GCAGAGGATG   240
 241  CACAGGGTGT  GCCAGCAGTG  AATGTTTGCC  CTGAATGCAC  ACCAAGGGCC  CCACCTGCCA   300
 301  CAGGACACAT  AGGACTCCAC  AGAGTCTGGC  CTCACCTCCC  TACTGTCAGT  CCTGTAGAAT   360
 361  CGACCTCTGC  TGGCCGGCTG  TACCCTGAGT  ACCCTCTCAC  TTCCTCCTTC  AGGTTTTCAG   420
 421  GGGACAGGCC  AACCCAGAGG  ACAGGATTCC  CTGGAGGGCA  CAGAGGAGCA  CCAAGGAGAA   480
 481  GATCTGTAAG  TAGGCCTTTG  TTAGAGTCTC  CAAGGTTCAG  TTCTCAGCTG  AGGCCTCTCA   540
 541  CACACTCCCT  CTCTCCCCAG  GCCTCTGGGT  CTTCATTGCC  CAGCTCCTGC  CCACACTCCT   600
 601  GCCTGCTGCC  CTGACGAGAG  TCATCATGTC  TCTTGAGCAG  AGGAGTCTGC  ACTGCAAGCC   660
 661  TGAGGAAGCC  CTTGAGGCCC  AACAAGAGGC  CCTGGGCCTG  GTGTGTGTGC  AGGCTGCCAC   720
 721  CTCCTCCTCC  TCTCCTCTCG  TCCTGGGCAC  CCTGGAGGAG  GTGCCCACTG  CTGGGTCAAC   780
 781  AGATCCTCCC  CAGAGTCCTC  AGGGAGCCTC  CGCCTTTCCC  ACTACCATCA  ACTTCACTCG   840
 841  ACAGAGGCAA  CCCACTGAGG  GTTCCAGCAG  CCGTGAAGAG  GAGGGGCCAA  GCACCTCTTG   900
 901  TATCCTGGAG  TCCTTGTTCC  GAGCAGTAAT  CACTAAGAAG  GTGGCTGATT  TGGTTGGTTT   960
 961  TCTGCTCCTC  AAATATCGAG  CCAGGGAGCC  AGTCACAAAG  GCAGAAATGC  TGGAGAGTGT  1020
1021  CATCAAAAAT  TACAAGCACT  GTTTTCCTGA  GATCTTCGGC  AAAGCCTCTG  AGTCCTTGCA  1080
1081  GCTGGTCTTT  GGCATTGACG  TGAAGGAAGC  AGACCCCACC  GGCCACTCCT  ATGTCCTTGT  1140
1141  CACCTGCCTA  GGTCTCTCCT  ATGATGGCCT  GCTGGGTGAT  AATCAGATCA  TGCCCAAGAC  1200
1201  AGGCTTCCTG  ATAATTGTCC  TGGTCATGAT  TGCAATGGAG  GGCGGCCATG  CTCCTGAGGA  1260
1261  GGAAATCTGG  GAGGAGCTGA  GTGTGATGGA  GGTGTATGAT  GGGAGGGAGC  ACAGTGCCTA  1320
1321  TGGGGAGCCC  AGGAAGCTGC  TCACCCAAGA  TTTGGTGCAG  GAAAAGTACC  TGGAGTACCG  1380
1381  GCAGGTGCCG  GACAGTGATC  CCGCACGCTA  TGAGTTCCTG  TGGGGTCCAA  GGGCCCTCGC  1440
1441  TGAAACCAGC  TATGTGAAAG  TCCTTGAGTA  TGTGATCAAG  GTCAGTGCAA  GAGTTCGCTT  1500
1501  TTTCTTCCCA  TCCCTGCGTG  AAGCAGCTTT  GAGAGAGGAG  GAAGAGGGAG  TCTGAGCATG  1560
1561  AGTTGCAGCC  AAGGCCAGTG  GGAGGGGGAC  TGGGCCAGTG  CACCTTCCAG  GGCCGCGTCC  1620
1621  AGCAGCTTCC  CCTGCCTCGT  GTGACATGAG  GCCCATTCTT  CACTCTGAAG  AGAGCGGTCA  1680
1681  GTGTTCTCAG  TAGTAGTTTT  CTGTTCTATT  GGGTGACTTC  GAGATTTATC  TTTGTTCTCT  1740
1741  TTTGGAATTG  TTTCAATGTT  TTTTTTTAAG  GGATGGTTGA  ATGAACTTCA  GCATCCAAGT  1800
1801  TTATGAATGA  CAGCAGTCAC  ACAGTTCTGT  GTATATAGTT  TAAGGGTAAG  AGTCTTGTGT  1860
1861  TTTATTCAGA  TTGGGAAATC  CATTCTATTT  TGTGAATTGG  GATAATAACA  GCAGTGCAAT  1920
1921  AAGTACTTAG  AAATGTGAAA  AATGAGCAGT  AAAATAGATG  AGATAAAGAA  CTAAAGAAAT  1980
1981  TAAGAGATAG  TCAATTCTTG  CCTTATACCT  CAGTCTATTC  TGTAAAATTT  TTAAAGATAT  2040
2041  ATGCATACCT  GGATTTCCTT  GGCTTCTTTG  AGAATGTAAG  AGAAATTAAA  TCTGAATAAA  2100
2101  GAATTCTTCC  TGTTCACTGG  CTCTTTTCTT  CTCCATGCAC  TGAGCATCTG  CTTTTTGGAA  2160
2161  GGCCCTGGGT  TAGTAGTGGA  GATGCTAAGG  TAAGCCAGAC  TCATACCCAC  CCATAGGGTC  2220
2221  GTAGAGTCTA  GGAGCTGCAG  TCACGTAATC  GAGGTGGCAA  GATGTCCTCT  AAAGATGTAG  2280
2281  GGAAAAGTGA  GAGAGGGGTG  AGGCTGTGGG  GCTCCGGGTG  AGAGTGGTGG  AGTGTCAATG  2340
2341  CCCTGAGCTG  GGGCATTTTG  GGCTTTGGGA  AACTGCAGTT  CCTTCTGGGG  GAGCTGATTG  2400
2401  TAATGATCTT  GGGTGGATCC                                                  2420
            |    10       |    20       |    30       |    40       |    50       |    60
```

EXAMPLE 21

After the 2.4 kb genomic segment had been identified, studies were carried out to determine if an "E+" subline expressed any homologous DNA. Cell line MZ2-MEL 3.0 was used as a source, and a cDNA library was prepared from its mRNA, using art known techniques. The 2.4 kb segment was used as a probe, and mRNA of about 1.8 kb was identified as homologous, using Northern blot analysis. When cDNA was screened, clones were obtained showing almost complete identity to parts of the 2.4 kb fragment. Two exons were thus identified. An additional exon was located upstream of these, via sequencing segments of cosmid B3 located in front of the 2.4 kb BamHI fragment. The gene extends over about 4.5 kb, as shown in FIG. 8. The starting point of the transcribed region was confirmed using PCR for the 5' end of the cDNA. The three exons comprise 65, 73, and 1551 base pairs. An ATG is located at position 66 of exon 3, followed by an 828 base pair reading frame.

EXAMPLE 22

To determine if smaller segments of the 2.4 kb fragment could transfer the expression of antigen E, smaller pieces corresponding to the larger gene were prepared, using art recognized techniques, and transferred into E⁻ cells. FIG. 8 shows the boundaries of the three segments.

Transfer of antigen expression in this manner indicates that the gene codes for the antigen precursor, rather than coding for a protein which activates the antigen.

EXAMPLE 23

The probing of cDNA described supra revealed, surprisingly, two different but closely related cDNAs. These cDNAs, when tested, did not transfer expression of antigen E, but they do show substantial homology to the first cDNA segment. The three segments, appear to indicate a newly recognized family of genes, referred to as "MAGE" for "melanoma antigen". In FIG. 9, "mage-1" directs expression of the antigen from MZ2 cells. Portions of the third exon of each gene are presented in FIG. 9. The second and third sequences are more closely related to each other than the first (18.1 and 18.9% difference compared to the first; 12% with each other). Out of 9 cDNA clones obtained, three of each type were obtained, suggesting equal expression. "MAGE" as used hereafter refers to a family of molecules, and the nucleic acids coding for them. These nucleic acids share a certain degree of homology and are expressed in tumor cells including several types of human tumor cells as well as in human tumors. The family is referred to as "MAGE" because the first members were identified in human melanoma cells. As the experiments which follow indicate, however, the members of the MAGE family are not at all restricted to melanoma tumors; rather, MAGE refers to a family of tumor rejection antigen precursors and the nucleic acid sequences coding therefore. The antigens resulting therefrom are referred to herein as "MAGE TRAs" or "melanoma antigen tumor rejection antigens"

EXAMPLE 24

Experiments with mouse tumors have demonstrated that new antigens recognized by T cells can result from point mutations that modify active genes in a region that codes for the new antigenic peptide. New antigens can also arise from the activation of genes that are not expressed in most normal cells. To clarify this issue for antigen MZ2-E, the mage-1 gene present in the melanoma cells was compared to that present in normal cells of patient MZ2. Amplification by polymerase chain reaction (PCR) of DNA of phytohemagglutinin-activated blood lymphocytes using primers surrounding a 1300 bp stretch covering the first half of the 2.4 kb fragment was carried out. As expected, a PCR product was obtained whereas none was obtained with the DNA of the E$^-$ variant. The sequence of this PCR product proved identical to the corresponding sequence of the gene carried by the E$^+$ melanoma cells. Moreover, it was found that antigen MZ2-E was expressed by cells transfected with the cloned PCR product. This result suggests that the activation of a gene normally silent is responsible for the appearance of tumor rejection antigen MZ2-E.

EXAMPLE 25

Figure 10:
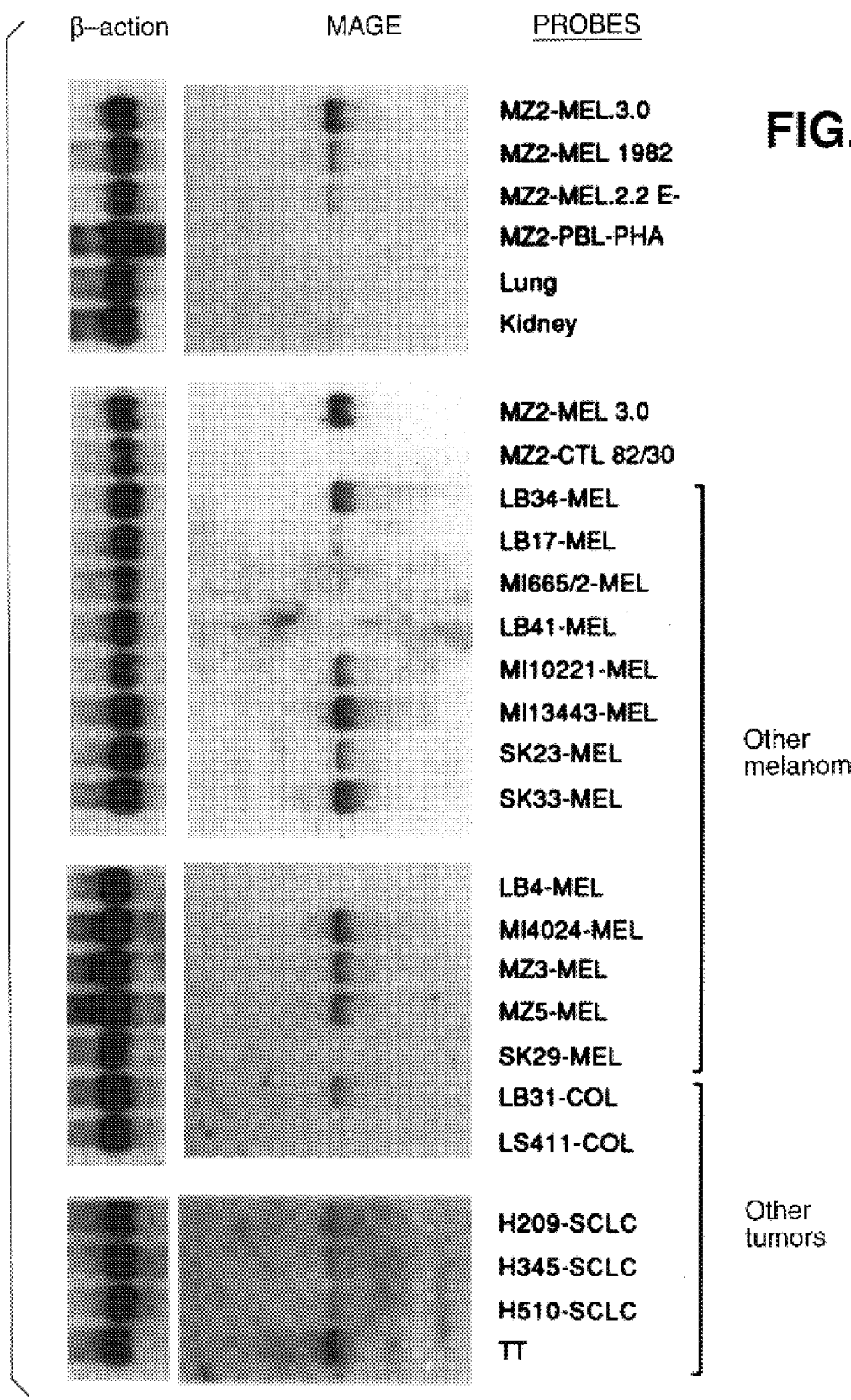
FIG. 10 shows the result of Northern blots for MAGE genes on various tissues.

In order to evaluate the expression of gene mage-1 by various normal and tumor cells, Northern blots were hybridized with a probe covering most of the third exon. In contrast with the result observed with human tumor cell line MZ2-MEL 3.0, no band was observed with RNA isolated from a CTL clone of patient MZ2 and phytohemagglutinin-activated blood lymphocytes of the same patient. Also negative were several normal tissues of other individuals (FIG. 10 and FIG. 11). Fourteen melanoma cell lines of other patients were tested. Eleven were positive with bands of varying intensities. In addition to these culture cell lines, four samples of melanoma tumor tissue were analyzed. Two samples, including a metastasis of patient MZ2 proved positive, excluding the possibility that expression of the gene represented a tissue culture artefact. A few tumors of other histological types, including lung tumors were tested. Most of these tumors were positive (FIGS. 10 and 11). These results indicated that the MAGE gene family is expressed by many melanomas and also by other tumors. However, they provided no clear indication as to which of genes mage-1, 2 or 3 were expressed by these cells, because the DNA probes corresponding to the three genes cross-hybridized to a considerable extent. To render this analysis more specific, PCR amplification and hybridization with highly specific oligonucleotide probes were used. cDNAs were obtained and amplified by PCR using oligonucleotide primers corresponding to sequences of exon 3 that were identical for the three MAGE genes discussed herein. The PCR products were then tested for their ability to hybridize to three other oligonucleotides that showed complete specificity for one of the three genes (FIG. 9). Control experiments carried out by diluting RNA of melanoma MZ2-MEL 3.0 in RNA from negative cells indicated that under the conditions used herein the intensity of the signal decreased proportionally to the dilution and that positive signals could still be detected at a dilution of $\frac{1}{300}$. The normal cells (lymphocytes) that were tested by PCR were confirmed to be negative for the expression of the three MAGE genes, suggesting therefore a level of expression of less than $\frac{1}{300}^{th}$ that of the MZ2 melanoma cell line (FIG. 11). For the panel of melanoma cell lines, the results clearly showed that some melanomas expressed MAGE genes mage 1, 2 and 3 whereas other expressed only mage-2 and 3 (FIGS. 11 and 10). Some of the other tumors also expressed all three genes whereas others expressed only mage-2 and 3 or only mage-3. It is impossible to exclude formally that some positive PCR results do not reflect the expression of one of the three characterized MAGE genes but that of yet another closely related gene that would share the sequence of the priming and hybridizing oligonucleotides. It can be concluded that the MAGE gene family is expressed by a large array of different tumors and that these genes are silent in the normal cells tested to this point.

EXAMPLE 26

Figure 13:
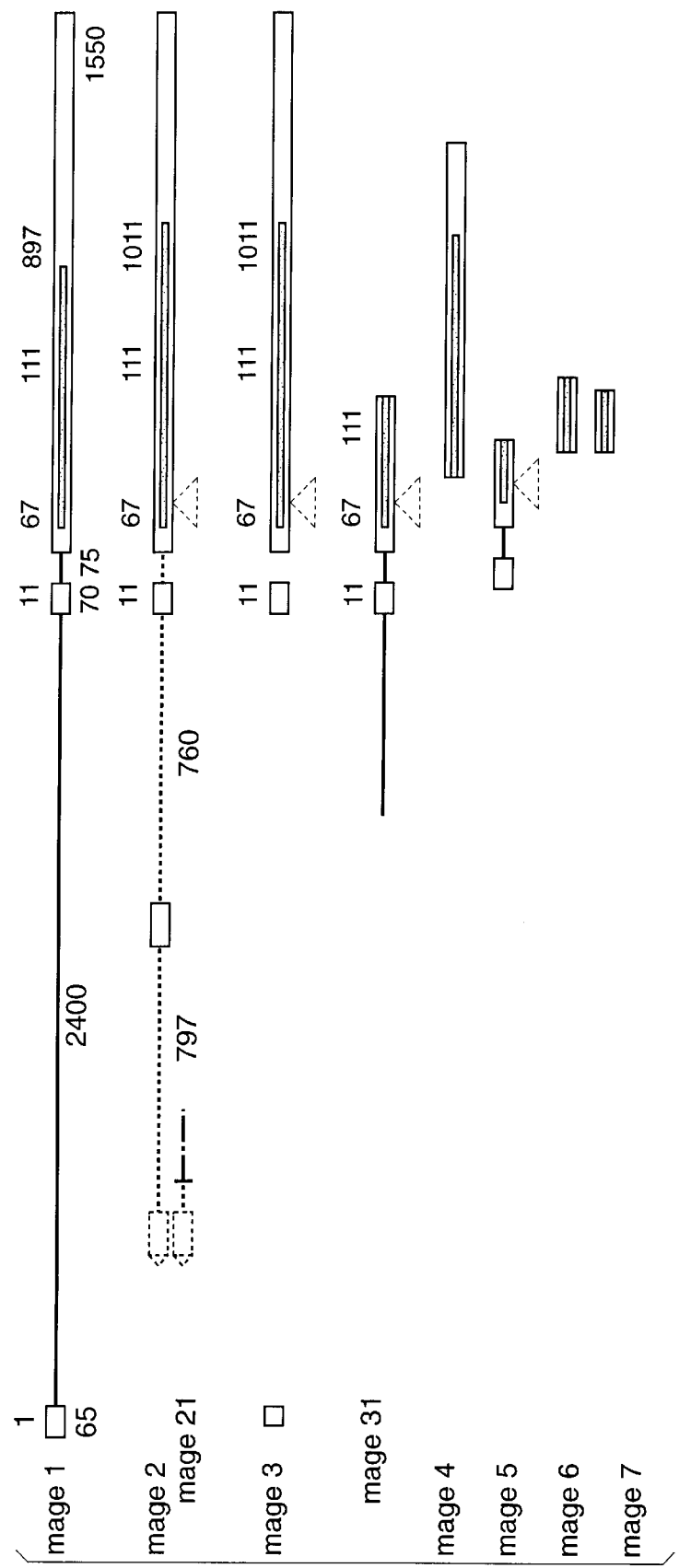
FIG. 13 is a generalized schematic of the expression of MAGE 1, 2 and 3 genes by tumor and normal tissues.
Figure 14B:
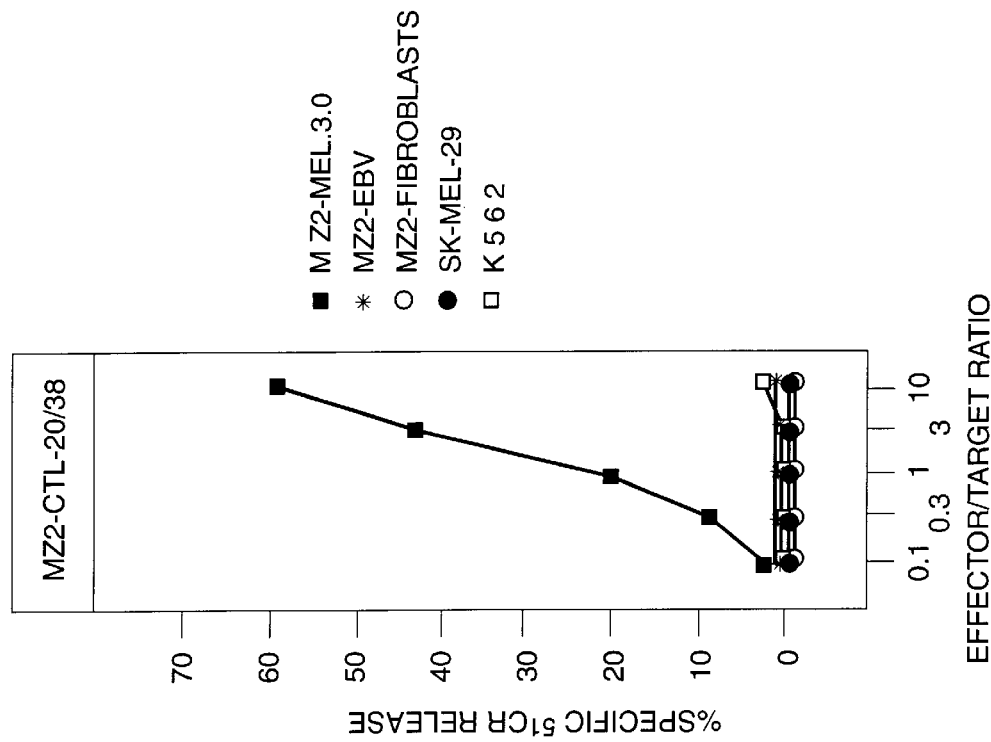
FIG. 14 shows results from a chromium release assay using CTL clone 20/38 on various cell lines.
Figure 14A:
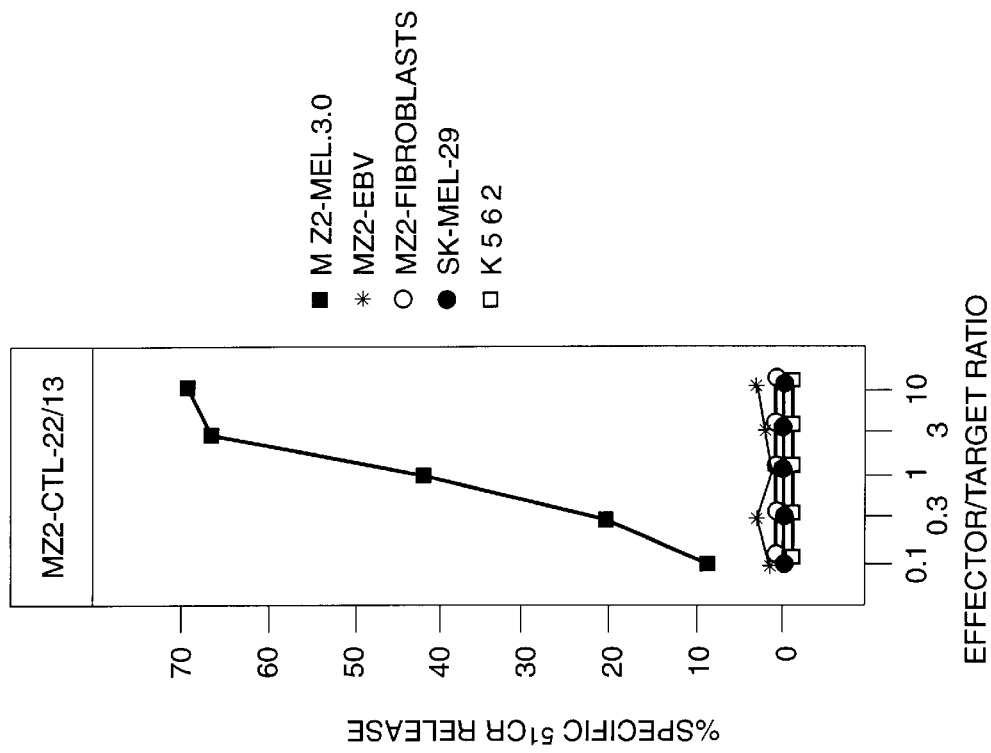
Figure 15A:
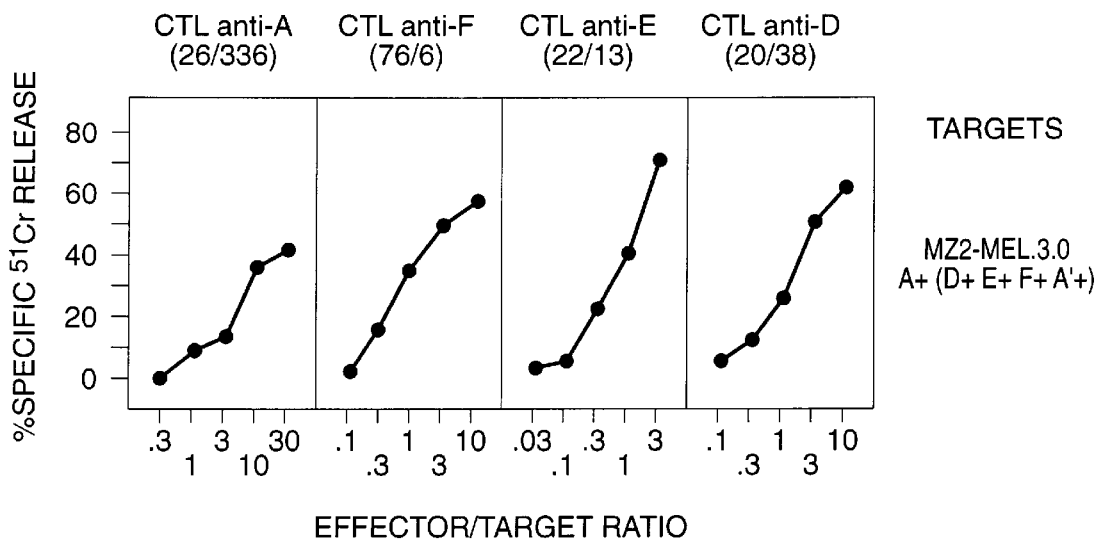
FIG. 15 presents the result of assays undertaken to determine antigenic specificity of CTL clone 20/38.
Figure 15B:
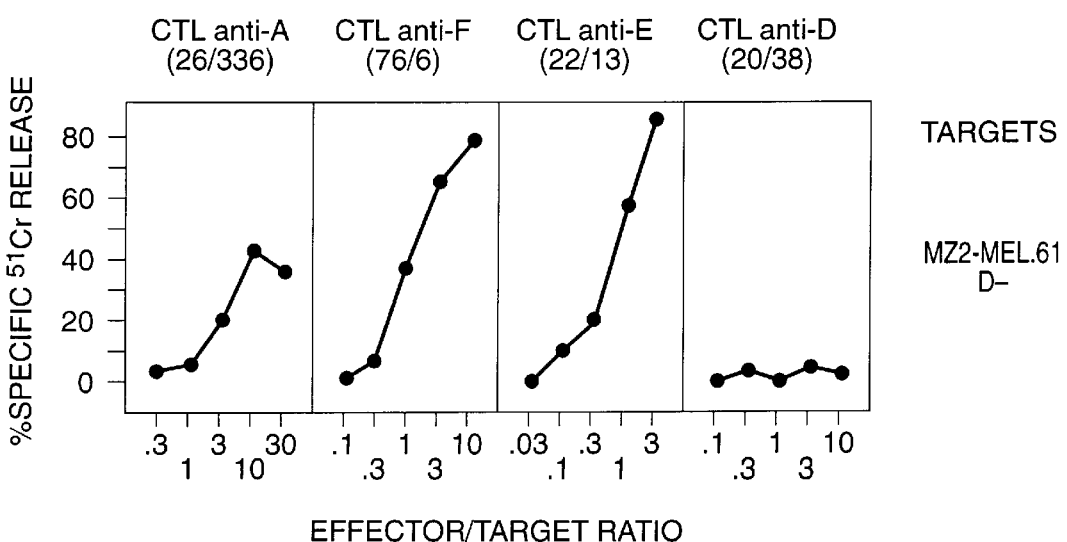
Figure 15C:
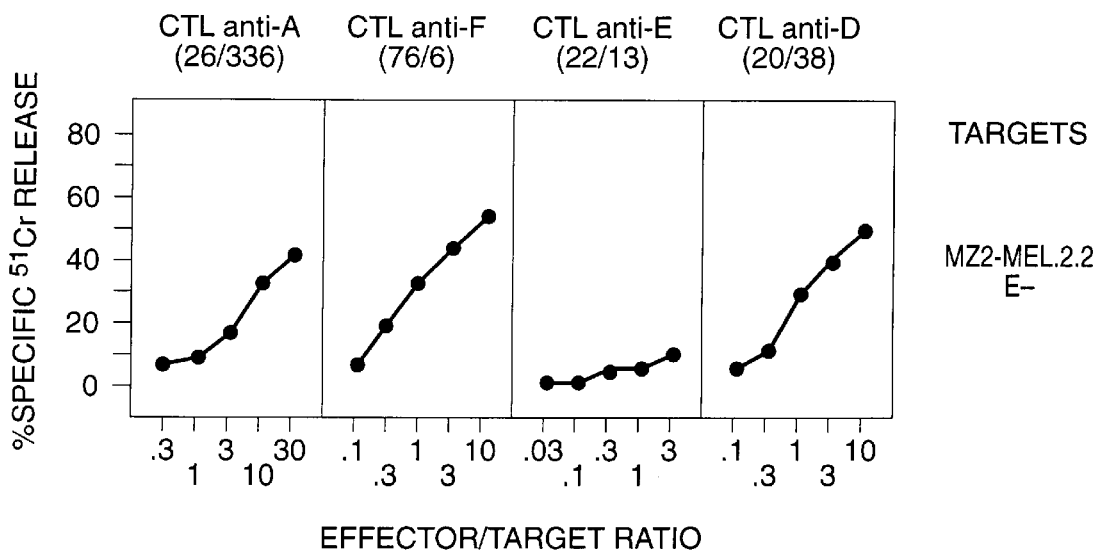
Figure 15D:
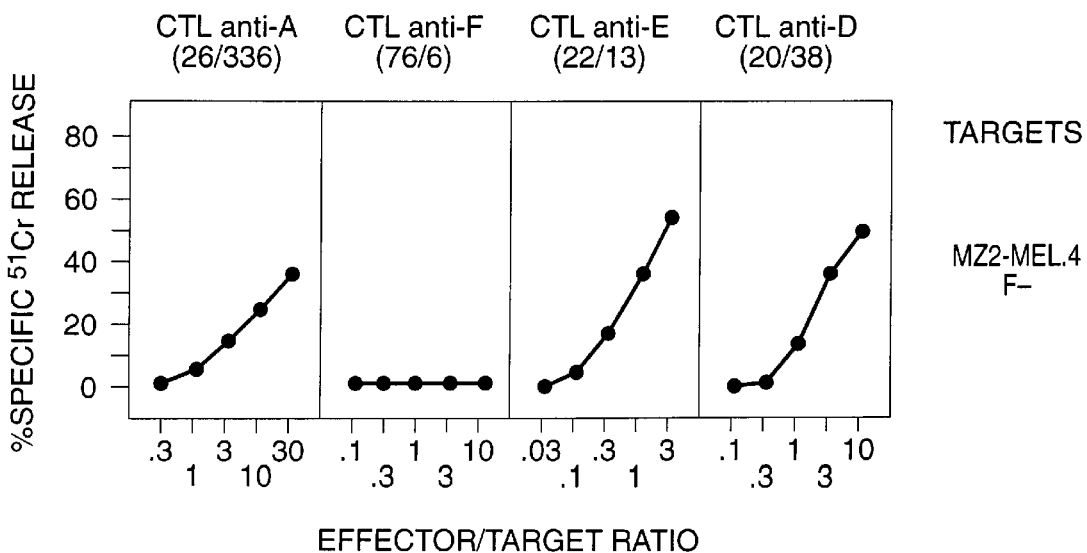

The availability of a sequence that transfects at high efficiency and efficiently expresses a TRAP made it possible to search for the associated major histocompatibility complex (MHC) class I molecule. The class I specificities of patient MZ2 are HLA-A1, A29, B37, B44 and C6. Four other melanomas of patients that had A1 in common with MZ2 were cotransfected with the 2.4 kb fragment and pSVtkneoβ. Three of them yielded neo$^r$ transfectants that stimulated TNF release by anti-E CTL clone 82/30, which is CD8+ (FIG. 10). No E– transfectant was obtained with four other melanomas, some of which shared A29, B44 or C6 with MZ2. This suggests that the presenting molecule for antigen MZ2-E is HLA-A1. In confirmation, it was found that, out of 6 melanoma cell lines derived from tumors of HLA-A1 patients, two stimulated TNF release by anti-E CTL clone 82/30 of patient MZ2. One of these tumor cell lines, MI13443-MEL also showed high sensitivity to lysis by these anti-E CTL. These two melanomas were those that expressed mage-1 gene (FIG. 13). Eight melanomas of patients with HLA haplotypes that did not include A1 were examined for their sensitivity to lysis and for their ability to stimulate TNF release by the CTL. None was found to be positive. The ability of some human anti-tumor CTL to lyse allogeneic tumors sharing an appropriate HLA specificity with the original tumor has been reported previously (Darrow, et al., J. Immunol. 142: 3329 (1989)). It is quite possible that antigenic peptides encoded by genes mage 2 and 3 can also be presented to autologous CTL by HLA-A1 or other class I molecules, especially in view of the similar results found with murine tumors, as elaborated upon supra.

EXAMPLE 27

As indicated supra, melanoma MZ2 expressed antigens F, D and A', in addition to antigen E. Following the isolation of the nucleic acid sequence coding for antigen E, similar experiments were carried out to isolate the nucleic acid sequence coding for antigen F.

To do this, cultures of cell line MZ2-MEL2.2, an E$^-$ cell line described supra, were treated with anti-F CTL clone 76/6, in the same manner described for treatment with anti-E CTL clones. This resulted in the isolation of an F antigen loss variant, which was then subjected to several rounds of selection. The resulting cell line, "MZ2-MEL2.2.5" was completely resistant to lysis by anti-F CTLs, yet proved to be lysed by anti-D CTLs.

Again, following the protocols set forth for isolation of antigen –E precursor DNA, the F⁻ variant was transfected with genomic DNA from F⁺ cell line MZ2-MEL3.0. The experiments yielded 90,000 drug resistant transfectants. These were tested for MZ2-F expression by using pools of 30 cells in the TNF detection assay elaborated upon supra. One pool stimulated TNF release by anti-F CTLs, and was cloned. Five of 145 clones were found to stimulate anti-F CTLs. Lysis assays, also following protocols described supra, confirmed (i) expression of the gene coding for antigen F, and (ii) presentation of antigen F itself.

EXAMPLE 28

Following identification of F⁺ cell lines, the DNA therefrom was used to transfect cells. To do this, a cosmid library of F⁺ cell line MZ2-MEL.43 was prepared, again using the protocols described supra. The library was divided into 14 groups of about 50,000 cosmids, and DNA from each group was transfected into MZ2-MEL2.2.5. Transfectants were then tested for their ability to stimulate TNF release from anti-F CTL clone 76/6. Of 14 groups of cosmids, one produced two independent transfectants expressing antigen F; a yield of two positives out of 17,500 geniticin resistant transfectants.

EXAMPLE 29

The existence of a gene family was suggested by the pattern observed on the Southern blot (FIG. 12). To do this, the 2.4 kb BamHI fragment, which transferred the expression of antigen M22-E, was labelled with 32p and used as a probe on a Southern Blot of BamHI digested DNA of E+cloned subclone M22-MEL2.2. Hybridization conditions included 50 $\mu$l/cm² of 3.5×SSC, 1×Denhardt's solution; 25 mM sodium phosphate buffer (pH 7.0), 0.5% SDS, 2 mM EDTA, where the 2.4 kb probes had been labelled with [$\alpha^{32}$p]dCTP (2–3000 Ci/mole), at 3×10⁶ cpm/ml. Hybridization was carried out for 18 hours at 65° C. After this, the membranes were washed at 65° C. four times for one hour each in 2×SSC, 0.1% SDS, and finally for 30 minutes in 0.1×SSC, 0.1% SDS. To identify hybridization, membranes were autoradiographed using Kodak X-AR film and Kodak X-Omatic fine intensifying screens.

In the following examples, whenever "hybridization" is referred to, the stringency conditions used were similar to those described supra. "Stringent conditions" as used herein thus refers to the foregoing conditions; subject to routine, art recognized modification.

EXAMPLE 30

The cDNA coding for mage 4 was identified from a sample of the human sarcoma cell line LB23-SAR. This cell line was found to not express mage 1, 2 or 3, but the mRNA of the cell line did hybridize to the 2.4 kb sequence for mage 1. To study this further, a cDNA library was prepared from total LB23-SAR mRNA, and was then hybridized to the 2.4 kb fragment. A cDNA sequence was identified as hybridizing to this probe, and is identified hereafter as mage 4.

EXAMPLE 31

Experiments were carried out using PHA-activated lymphocytes from patient "MZ2", the source of the "MZ" cells discussed supra. An oligonucleotide probe which showed homology to mage 1 but not mage 2 or 3 was hybridized with a cosmid library derived from the PHA activated cells. The size of the hybridizing BamHI cosmid fragment, however, was 4.5 kb, thus indicating that the material was not mage 1; however, on the basis of homology to mage 1–4, the fragment can be referred to as "mage 5". The sequence of MAGE 5 is presented in SEQ ID NO: 16.

EXAMPLE 32

Melanoma cell line LB-33-MEL was tested. Total mRNA from the cell line was used to prepare cDNA, which was then amplified with oligos CHO9: (ACTCAGCTCCTCCCAGATTT) (SEQ ID NO: 27), and CHO10: (GAAGAGGAGGGGCCAAG) (SEQ ID NO: 28). These oligos correspond to regions of exon 3 that are common to previously described mage 1, 2 and 3.

To do this, 1 $\mu$g of RNA was diluted to a total volume of 20 $\mu$l, using 2 $\mu$l of 10× PCR buffer, 2 $\mu$l of each of 10 mM dNTP, 1.2 $\mu$l of 25 mM MgCl₂, 1 $\mu$l of an 80 mM solution of CHO9, described supra, 20 units of RNAsin, and 200 units of M-MLV reverse transcriptase. This was followed by incubation for 40 minutes at 42° C. PCR amplification followed, using 8 $\mu$l of 10× PCR buffer, 4.8 $\mu$l of 25 mM MgCl₂, 1 $\mu$l of CHO10, 2.5 units of Thermus acquaticus ("Taq") polymerase, and water to a total volume of 100 $\mu$l. Amplification was then carried out for 30 cycles (1 minute 94° C.; 2 minutes at 52° C., 3 minutes at 72° C.). Ten $\mu$l of each reaction were then size fractionated on agarose gel, followed by nitrocellulose blotting. The product was found to hybridize with oligonucleotide probe CHO18 (TCTTGTATCCTGGAGTCC) (SEQ ID NO: 80). This probe identified mage 1 but not mage 2 or 3. However, the product did not hybridize to probe SEQ 4 (TTGCCAAGATCTCAGGAA). This probe also binds mage 1 but not 2 and 3. This indicated that the PCR product contained a sequence that differed from mage 1, 2 and 3. Sequencing of this fragment also indicated differences with respect to mage 4 and 5. These results indicate a sequence differing from previously identified mage 1, 2, 3, 4 and 5, and is named mage 6.

EXAMPLE 33

In additional experiments using cosmid libraries from PHA-activated lymphocytes of MZ2, the 2.4 kb mage 1 fragment was used as a probe and isolated a complementary fragment. This clone, however, did not bind to oligonucleotides specific for mage 1, 2, 3 or 4. The sequence obtained shows some homology to exon 3 of mage 1, and differs from mages 1–6. It is referred to as mage 7 hereafter. Additional screenings yielded mage 8–11.

EXAMPLE 34

The usefulness of the TRAPs, as well as TRAs derived therefrom, was exemplified by the following.

Exon 3 of mage 1 was shown to transfer expression of antigen E. As a result, it was decided to test whether synthetic peptides derived from this exon 3 could be used to confer sensitivity to anti-E CTL.

To do this, and using standard protocols, cells normally insensitive to anti-E/CTLs were incubated with the synthetic peptides derived from Exon 3.1. Using the CTL lytic assays described supra on P815A, and a peptide concentration of 3 mM, the peptide Glu-Ala-Asp-Pro-Thr-Gly-His-Ser-Tyr (See SEQ ID NO: 26) was shown to be best. The assay showed lysis of 30%, indicating conferring of sensitivity to the anti-E CTL.

EXAMPLE 35

Nucleic acid sequences referred to as "smage" were isolated from murine cells. Using the protocols described supra, a cosmid library was prepared from the DNA of normal DBA/2 kidney cells, using cosmid vector C2RB. As a probe, the 2.4 kb BamHI fragment of MAGE-1 was used. The DNA was blotted to nylon filters, and these were washed in 2×SSC at 65° C. to identify the smage material.

EXAMPLE 36

Further tissue samples were tested for the presence of MAGE genes, using the protocols discussed supra. Some of these results follow.

There was no expression of the MAGE genes in brain or kidney tumor tissue. Colon tumor tissue showed expression of MAGE 1, 2, 3 and 4, although not all tumors tested showed expression of all MAGE genes. This is also true for pancreatic tumor (MAGE 1); non-small cell lung (MAGE 1, 2, 3 and 4), prostate (MAGE 1), sarcomas (MAGE 1, 2, 3 and 4), breast (MAGE 1, 2 and 3), and larynx (MAGE 1 and 4).

EXAMPLE 37

A cytolytic CTL clone "20/38" was obtained from peripheral blood lymphocytes of melanoma patient MZ2. This clone is described by Van den Eynde et al., Int. J. Cancer 44: 634–640 (1989), the disclosure of which is incorporated by reference. The CTL clone has isolated following Herin et al., Int. J. Cancer 39: 390–396 (1987), which is incorporated by reference. The assay is described herein, however. Autologous melanoma cells were grown in vitro, and then resuspended at $10^7$ cells/ml in DMEM, supplemented with 10% HEPES and 30% FCS, and incubated for 45 minutes at 37° C. with 200 μCi/ml of Na($^{51}$Cr)O$_4$. Labelled cells were washed three times with DMEM, supplemented with 10 mM HEPES. These were then resuspended in DMEM supplemented with 10 mM HEPES and 10% FCS, after which 100 μl aliquots containing $10^3$ cells, were distributed into 96 well microplates. Samples of the CTL clone were added in 100 ul of the same medium, and assays were carried out in duplicate. Plates were centrifuged for four minutes at 100 g, and incubated for four hours at 37° C. in a 5.5% CO$_2$ atmosphere.

Plates were centrifuged again, and 100 ul aliquots of supernatant were collected and counted. Percentage of $^{51}$Cr release was calculated as follows:

$$\%^{51}\text{Cr release} = \frac{(ER - SR)}{(MR - SR)} \times 100$$

where ER is observed, experimental $^{51}$Cr release, SR is spontaneous release measured by incubating $10^3$ labeled cells in 200 ul of medium alone, and MR is maximum release, obtained by adding 100 ul 0.3% Triton X-100 to target cells.

Those mononuclear blood samples which showed high CTL activity were expanded and cloned via limiting dilution, and were screened again, using the same methodology.

The same method was used to test target K562 cells. When EBV-B cells were used, the only change was the replacement of DMEM medium by Hank's medium, supplemented with 5% FCS.

These experiments led to isolation of CTL clone 20/38.

FIG. 1 presents the results of these assays. Specifically, it will be seen that the CTL clone lysed autologous melanoma cell line MZ2-MEL.3.0, but did not lyse EBV-B cell lines, fibroblasts, K562 or non-autologous melanoma cell line SK-MEL-29.

EXAMPLE 38

Once the CTL clone was recognized as being specific for the autologous cell line, it was tested for antigenic specificity. To do this, antigen loss variants derived from patient MZ2 were tested in the same type of chromium release assay described above. These target lines were MZ2-MEL 3.0, which is D$^+$, E$^+$, F$^+$, A$^+$, MZ2-MEL.61, which is D$^-$, MZ2-MEL 2.2, which is E$^-$, and MZ2-MEL.4, which is F$^-$. In addition to CTL clone 20/38, clones which are known to be anti-A (CTL 28/336), anti-F (CTL 76/6), and anti-E (CTL 22/13) were tested.

These results are set forth in FIG. 15. It will be seen that CTL clone 20/38 lysed all the cell lines leading to chromium release except D$^-$ cell line MZ2-MEL.61, thus indicating that the CTL clone is anti-D. This result was confirmed, in experiments not included herein, by experiments where TNF release by the CTL clone was observed only in the presence of melanoma lines presenting antigen D.

EXAMPLE 39

Once antigen D was identified as the target molecule, studies were carried out to determine the HLA type which presented it. The experiments described in example A showed that antigen D was presented by MZ2-MEL, and this cell line's HLA specificity is known (i.e., A1, A29, B37, B44, Cw6, C.cl.10). It was also known, however, that a variant of MZ2-MEL which had lost HLA molecules A29, B44 and C.cl.10 still expressed antigen D, so these could be eliminated from consideration. Studies were not carried out on lines expressing B37, as none could be found.

In all, 13 allogeneic lines were tested, which expressed either HLA-A1 (10 of 13), or Cw6 (3 of 13). The cell lines were tested for their ability to stimulate release of TNF by CTL clone 20/38, using the method of Traversari et al., Immunogenetics 35: 145–152 (1992), the disclosure of which is incorporated by reference. This assay measures TNF release via testing toxicity of supernatants on WEHI 164-13 cells.

In the assays, cell samples (3000, 10,000 or 30,000 cells) from the allogeneic lines were cultured in the presence of 1500 cells of the CTL clone, and 25 u/ml of IL-2. Twenty-four hours later, the supernatant from the culture was tested against the WEHI cells for toxicity. The results are presented in Table 1, which follows.

Eight cell lines were found to stimulate TNF release from the CTL clone 20/38. All of these lines were HLA-A1. None of the Cw6 presenting lines did so.

The cell lines were also assayed to determine MAGE expression. All eight of the lines which stimulated TNF release expressed MAGE-3, whereas the two HLA-A1 lines which were negative did not.

cells were incubated overnight at 37° C., medium was removed and then replaced by 30 μl/well of DMEM medium containing 10% Nu serum, 400 μg/ml DEAE-dextran, 100 μM chloroquine, and the plasmids described above. Follow-

TABLE 3

|  |  | TNF pg/ml | | | | |
|---|---|---|---|---|---|---|
|  |  | Exp 1 | | Exp 2 | | |
| Melanoma | Number of Cells | +CTL 20/38 | | +CTL 20/38 | Expression of Mage-3 | Expression of HLA-A-1 |
| MZ2-MEL.61.2 | 50000 |  | 1 |  | 4 | +++ | + |
| MZ2-MEL-ET1 | 50000 |  | >120 |  | >120 | +++ | + |
|  | 1666 |  | 66 |  | >120 |  |  |
| LY-1-MEL | 30000 | 1 | >120 | 1 | >120 | +++ | + |
|  | 10000 | 1 | >120 | 1 | >120 |  |  |
|  | 3000 | <1 | 114 | 2 | >120 |  |  |
| MI-10221 | 30000 | <1 | >120 |  |  | +++ | + |
|  | 10000 | <1 | 71 |  |  |  |  |
|  | 3000 | <1 | 74 |  |  |  |  |
| LY-2-MEL | 30000 | 1 | 57 |  |  | +++ | + |
|  | 10000 | 1 | 86 |  |  |  |  |
|  | 3000 | 1 | 91 |  |  |  |  |
| LY-4-MEL | 30000 | 1 | >120 |  |  | +++ | + |
|  | 10000 | 1 | >120 |  |  |  |  |
|  | 3000 | 1 | >120 |  |  |  |  |
| SK23-MEL | 30000 | 1 | 112 |  |  | +++ | + |
|  | 10000 | 1 | 116 |  |  |  |  |
|  | 3000 | 1 | 105 |  |  |  |  |
| MI-665/2-MEL | 30000 | 1 | 3 | 2 | 4 | − | + |
|  | 10000 | 1 | 2 | 2 | 5 |  |  |
|  | 3000 | 1 | 5,2 | 1 | 5 |  |  |
| LB34-MEL | 30000 | 1 | >120 |  |  | +++ | + |
|  | 10000 | 1 | >120 |  |  |  |  |
|  | 3000 | 1 | >120 |  |  |  |  |
| LB45-MEL | 30000 | 1 | 11 | 1 | 30 | − | + |
|  | 10000 | 1 | 6 | 1 | 12 |  |  |
|  | 3000 | 1 | 2 | <1 | 7 |  |  |
| NA-6-MEL | 30000 | 1 | 77 | 5 | 98 | +++ | + |
|  | 10000 | 1 | 104 | 5 | >120 |  |  |
|  | 3000 | 1 | 110 | 4 | >120 |  |  |
| MI-13443-MEL | 30000 | 1 | >120 |  |  | +++ | + |
|  | 10000 | 1 | >120 |  |  |  |  |
|  | 3000 | 1 | >120 |  |  |  |  |
| LB5-MEL | 30000 | 1 | 8 | 4 | 9 | + | − |
|  | 10000 | <1 | 5 | 4 | 11 |  |  |
|  | 3000 | <1 | 5 | 1 | 5 |  |  |
| SK64-MEL | 30000 | 1 | 4 | 2 | 5 | ? | − |
|  | 10000 | 1 | 2 | 1 | 5 |  |  |
|  | 3000 | 1 | 1 | 1 | 4 |  |  |
| LB33-MEL | 30000 |  |  | 1 | 3,5 | +++ | − |
|  | 10000 |  |  | 1 | 4 |  |  |
|  | 3000 |  |  | 1 | 3 |  |  |
| LB73-MEL | 50000 |  | 16 |  |  | − | − |

1500 CTL 20/38 and 25μ/ml IL2 were mixed with the indicated number of cells of the different allogeneic melanomas. 24 hours later, the amount of TNF present in the supernatant was assayed by testing its cytotoxicity for WEHI-164-13 cells.

EXAMPLE 40

In view of the results set forth in example C, experiments were carried out to determine if antigen D was in fact a tumor rejection antigen derived from MAGE-3. To do this, recipient COS7 cells were transfected with 100 ng of the gene for HLA-A1 cloned into pcDNA I/Amp, and 100 ng of one of (a) cDNA for MAGE-1 cloned into pcDNA I/Amp, (b) cDNA for MAGE-2 cloned into pcDSRa, or (c) cDNA for MAGE-3 cloned into pcDSRα. The transfecting sequences were ligated into the plasmids in accordance with manufacturer's instructions. Samples of COS-7 cells were seeded, at 15,000 cells/well into tissue culture flat bottom microwells, in Dulbeco's modified Eagles Medium ("DMEM") supplemented with 10% fetal calf serum. The ing four hours of incubation at 37° C., the medium was removed, and replaced by 50 μl of PBS containing 10% DMSO. This medium was removed after two minutes and replaced by 200 μl of DMEM supplemented with 10% of FCS.

Figure 16:
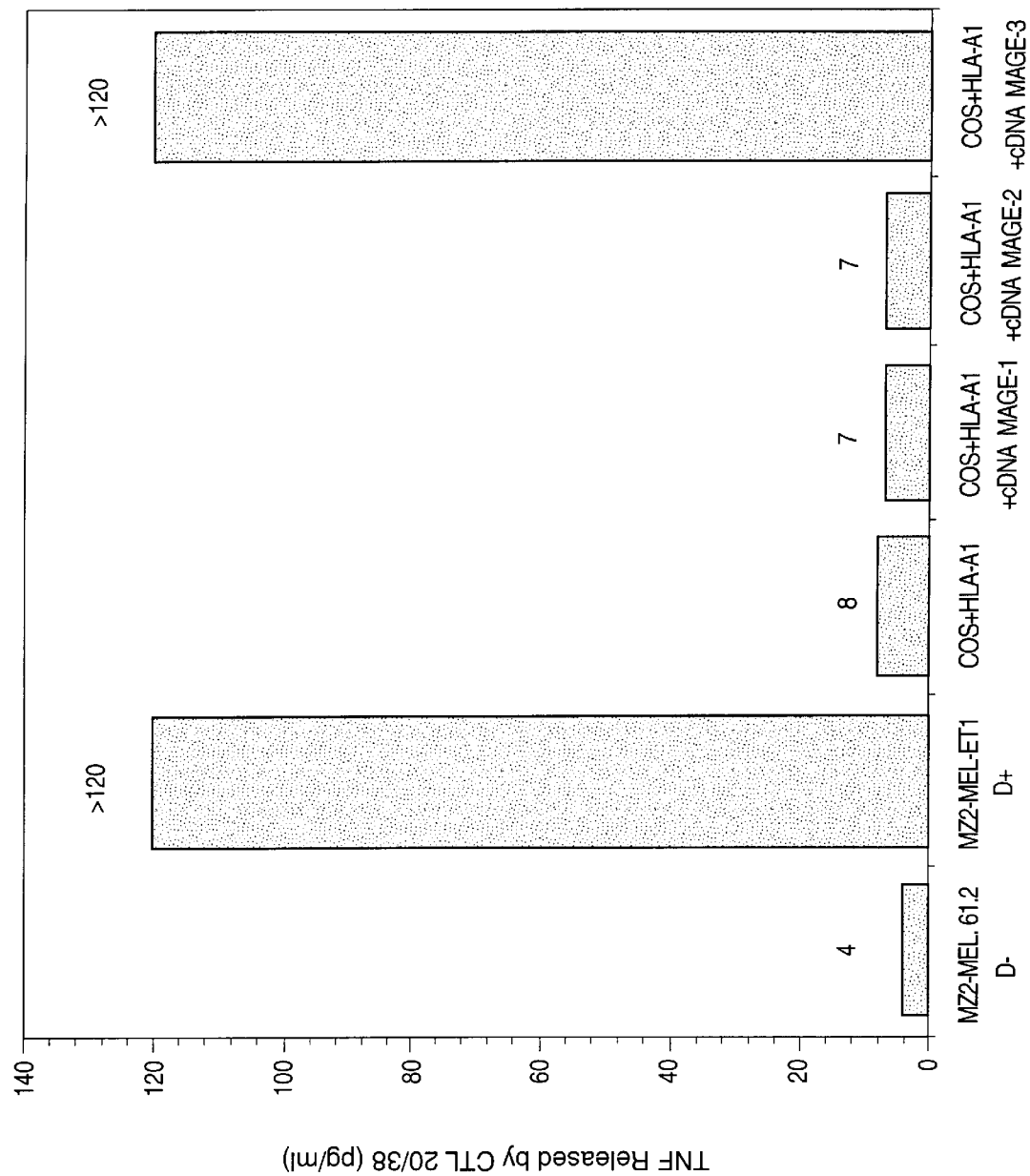
FIG. 16 shows the results obtained when a TNF release assay was carried out on various transfected cells.

Following this change in medium, COS cells were incubated for 24 hours at 37° C. Medium was then discarded, and 1500 cells of CTL clones 20/38 were added, in 100 μl of Iscove medium containing 10% pooled human serum, supplemented with 25 u/ml of IL-2. Supernatant was removed after 24 hours, and TNF content was determined in an assay on WEHI cells, as described by Traversari et al., Immunogenetics 35: 145–152 (1992), the disclosure of which is incorporated by reference. These results are shown in FIG. 16.

It will be seen that the CTL clone was strongly stimulated by COS7 cells transfected with HLA-A1 and MAGE-3, but not by the cells transfected with the other mage genes. This leads to the conclusion that antigen D is a tumor rejection antigen derived from the tumor rejection antigen precursor coded by gene MAGE-3, and that this TRA is presented by HLA-A1 molecules.

The foregoing disclosure, including the examples, places many tools of extreme value in the hands of the skilled artisan. To begin, the examples identify and provide a methodology for isolating nucleic acid molecules which code for tumor rejection antigen precursors as well as the nucleic acid molecules complementary thereto. It is known that DNA exists in double stranded form, and that each of the two strands is complementary to the other. Nucleic acid hybridization technology has developed to the point where, given a strand of DNA, the skilled artisan can isolate its complement, or synthesize it. "Nucleic acid molecule" as used herein refers to all species of DNA and RNA which possess the properties discussed sutra. Genomic and complementary DNA, or "cDNA" both code for particular proteins, and as the examples directed to isolation of MAGE coding sequences show, this disclosure teaches the artisan how to secure both of these.

Similarly, RNA molecules, such as mRNA can be secured. Again, with reference to the skilled artisan, once one has a coding sequence in hand, mRNA can be isolated or synthesized.

Complementary sequences which do not code for TRAP, such as "antisense DNA" or mRNA are useful, e.g., in probing for the coding sequence as well as in methodologies for blocking its expression.

It will also be clear that the examples show the manufacture of biologically pure cultures of cell lines which have been transfected with nucleic acid sequences which code for or express the TRAP molecules. Such cultures can be used as a source for tumor rejection antigens, e.g., or as therapeutics. This aspect of the invention is discussed infra.

Cells transfected with the TRAP coding sequences may also be transfected with other coding sequences. Examples of other coding sequences include cytokine genes, such as interleukins (e.g., IL-2 or IL-4), or major histocompatibility complex (MHC) or human leukocyte antigen (HLA) molecules. Cytokine gene transfection is of value because expression of these is expected to enhance the therapeutic efficacy of the biologically pure culture of the cells in vivo. The art is well aware of therapies where interleukin transfectants have been administered to subjects for treating cancerous conditions. In a particularly preferred embodiment, cells are transfected with sequences coding for each of (i) a TRAP molecule, (ii) an HLA/MHC molecule, and (iii) a cytokine.

Transfection with an MHC/HLA coding sequence is desirable because certain of the TRAs may be preferentially or specifically presented only by particular MHC/HLA molecules. Thus, where a recipient cell already expresses the MHC/HLA molecule associated with presentation of a TRA, additional transfection may not be necessary although further transformation could be used to cause over-expression of the antigen. On the other hand, it may be desirable to transfect with a second sequence when the recipient cell does not normally express the relevant MHC/HLA molecule. It is to be understood, of course, that transfection with one additional sequence does not preclude further transfection with other sequences.

The term "biologically pure" as used in connection with the cell line described herein simply means that these are essentially free of other cells. Strictly speaking, a "cell line" by definition is "biologically pure", but the recitation will establish this fully.

Transfection of cells requires that an appropriate vector be used. Thus, the invention encompasses expression vectors where a coding sequence for the TRAP of interest is operably linked to a promoter. The promoter may be a strong promoter, such as those well known to the art, or a differential promoter, i.e., one which is operative only in specific cell types. The expression vectors may also contain all or a part of a viral or bacterial genome, such as vaccinia virus or BCG. Such vectors are especially useful in preparing vaccines.

The expression vectors may incorporate several coding sequences, as long as the TRAP sequence is contained therein. The cytokine and/or MHC/HLA genes discussed supra may be included in a single vector with the TRAP sequence. Where this is not desired, then an expression system may be provided, where two or more separate vectors are used where each coding sequence is operably linked to a promoter. Again, the promoter may be a strong or differential promoter. Co-transfection is a well known technique, and the artisan in this field is expected to have this technology available for utilization. The vectors may be constructed so that they code for the TRA molecule directly, rather than the TRAP molecule. This eliminates the need for post-translational processing.

As the foregoing discussion makes clear, the sequences code for "tumor rejection antigen precursors" ("TRAPs") which, in turn, are processed into tumor rejection antigens ("TRAs"). Isolated forms of both of these categories are described herein, including specific examples of each. Perhaps their most noteworthy aspect is as vaccines for treating various cancerous conditions. The evidence points to presentation of TRAs on tumor cells, followed by the development of an immune response and deletion of the cells. The examples show that when various TRAs are administered to cells, a CTL response is mounted and presenting cells are deleted. This is behavior characteristic of vaccines, and hence TRAPs, which are processed into TRAs, and the TRAs themselves may be used, either alone or in pharmaceutically appropriate compositions, as vaccines. Similarly, presenting cells may be used in the same manner, either alone or as combined with ingredients to yield pharmaceutical compositions. Additional materials which may be used as vaccines include isolated cells which present the TRA molecule on their surface, as well as TRAP fragments, mutated viruses, especially etiolated forms, and transfected bacteria. "Fragments" as used herein refers to peptides which are smaller than the TRA, but which possess the properties required of a vaccine, as discussed supra. Another vaccine comprises or consists of complexes of TRA and HLA molecule. Vaccines of the type described herein may be used preventively, i.e., via administration to a subject in an amount sufficient to prevent onset of a cancerous condition.

The generation of an immune response, be it T-cell or B-cell related, is characteristic of the effect of the presented tumor rejection antigen. With respect to the B-cell response, this involves, inter alia, the generation of antibodies to the TRA, i.e., which specifically bind thereto. In addition, the TRAP molecules are of sufficient size to render them immunogenic, and antibodies which specifically bind thereto are a part of this invention. These antibodies may be polyclonal or monoclonal, the latter being prepared by any of the well recognized methodologies for their preparation which need not be repeated here. For example, mAbs may be prepared using an animal model, e.g., a Balb/C mouse or in a test tube, using, e.g., EBV transformants. In addition, antiserum may be isolated from a subject afflicted with a cancerous condition where certain cells present a TRA. Such antibodies may also be generated to epitopes defined by the interaction of TRA and HLA/MHC molecules.

Review of the foregoing disclosure will show that there are a number of facets to the system which may be referred to as "tumor rejection antigen presentation and recognition". Recognition of these phenomena has diagnostic consequences. For example, the existence of specific CTL clones, or antibodies to the TRA makes it possible to diagnose or monitor cancerous conditions (explained infra), by monitoring the CTLs in a sample from a subject, binding of antibodies to TRAs, or the activity of anti-TRA CTLs in connection with subject samples. Similarly, the expression of nucleic acid molecules for TRAPs can be monitored via amplification (e.g., "polymerase chain reaction"), anti-sense hybridization, probe technologies, and so forth. Various subject samples, including body fluids (blood, serum, and other exudates, e.g.), tissues and tumors may be so assayed.

A particular manner of diagnosis is to use an adaptation of the standard "tuberculin test" currently used for diagnosis of tuberculosis. This standard skin test administers a stable form of "purified protein derivative" or "PPD" as a diagnostic aid. In a parallel fashion, TRAs in accordance with this invention may be used in such a skin test as a diagnostic aid or monitoring method.

The term "cancerous condition" is used herein to embrace all physiological events that commence with the initiation of the cancer and result in final clinical manifestation. Tumors do not spring up "ab initio" as visible tumors; rather there are various events associated with the transformation of a normal cell to malignancy, followed by development of a growth of biomass, such as a tumor, metastasis, etc. In addition, remission may be conceived of as part of "a cancerous condition" as tumors seldom spontaneously disappear. The diagnostic aspects of this invention include all events involved in carcinogenesis, from the first transformation to malignancy of a single cell, through tumor development and metastasis, as well as remission. All are embraced herein.

Where "subject" is used, the term embraces any species which can be afflicted with a cancerous condition. This includes humans and non-humans, such as domesticated animals, breeding stock, and so forth.

There are therapeutic aspects of this invention as well. The efficacy of administration of effective amounts of TRAPs and TRAs as vaccines has already been discussed supra. Similarly, one may develop the specific CTLs in vitro and then administer these to the subject. Antibodies may be administered, either polyclonal or monoclonal, which specifically bind to cells presenting the TRA of interest. These antibodies may be coupled to specific antitumor agents, including, but not being limited to, methotrexate radioiodinated compounds, toxins such as ricin, other cytostatic or cytolytic drugs, and so forth. Thus, "targeted" antibody therapy is included herein, as is the application of deletion of the cancerous cells by the use of CTLs.

The data from examples 37–40 show that a tumor rejection antigen derived from MAGE-3 is presented by HLA-A1 molecules. As such, in addition to the nucleic acid molecules coding for this TRAP, the TRAP itself as coded for by the sequences, vectors, cell lines, etcetera which incorporate this nucleic acid molecule, the invention also encompasses combination of the molecules coding for the MAGE-3 TRAP and HLA-A1. Thus, co-transfectants, vectors containing coding sequences for both, expression systems such as kits, or separate vectors, and so forth, are all embraced by the invention. Similarly, the vaccines discussed supra can be made by incorporating the TRAP from MAGE-3 and an adjuvant.

It is to be understood that a given TRAP may yield more than one TRA. In the case of MAGE-3, it has been shown that antigen D, as the term is used herein, derives therefrom, and one aspect of the invention is this isolated tumor rejection antigen. Another is isolated complexes of the TRA and its presenting molecule, i.e., HLA-A1.

The identification of MAGE-3 derived TRAs as being presented by HLA-A1 molecules suggests various therapeutic and diagnostic approaches. In a therapeutic context, e.g., the treatment of a disorder characterized by MAGE-3 expression may be treated in a number of ways, "disorder" being used to refer to any pathological condition where MAGE-3 TRAP is expressed, such as cancer (e.g., melanoma).

Therapeutic approaches based upon the disclosure are premised on a response by a subject's immune system, leading to lysis of TRA presenting cells, such as HLA-A1 cells. One such approach is the administration of CTLs specific to the complex to a subject with abnormal cells of the phenotype at issue. it is within the skill of the artisan to develop such CTLs in vitro. Specifically, a sample of cells, such as blood cells, are contacted to a cell presenting the complex and capable of provoking a specific CTL to proliferate. The target cell can be a transfectant, such as a COS cell of the type described supra. These transfectants present the desired complex on their surface and, when combined with a CTL of interest, stimulate its proliferation. COS cells, such as those used herein are widely available, as are other suitable host cells.

To detail the therapeutic methodology, referred to as adoptive transfer (Greenberg, J. Immunol. 136(5): 1917 (1986); Reddel et al., Science 257: 238 (Jul. 10, 1992); Lynch et al., Eur. J. Immunol. 21: 1403–1410 (1991); Kast et al., Cell 59: 603–614 (Nov. 17, 1989)), cells presenting the desired complex are combined with CTLs leading to proliferation of the CTLs specific thereto. The proliferated CTLs are then administered to a subject with a cellular abnormality which is characterized by certain of the abnormal cells presenting the particular complex. The CTLs then lyse the abnormal cells, thereby achieving the desired therapeutic goal.

The foregoing therapy assumes that at least some of the subject's abnormal cells present the HLA/TRA complex. This can be determined very easily, as the art is very familiar with methods for identifying cells which present a particular HLA molecule, as well as how to identify cells expressing DNA containing the indicated sequences. Once isolated, such cells can be used with a sample of a subject's abnormal cells to determine lysis in vitro. If lysis is observed, then the use of specific CTLs in such a therapy may alleviate the condition associated with the abnormal cells. A less involved methodology examines the abnormal cells for HLA phenotyping, using standard assays, and determines expression via amplification using, e.g., PCR.

Adoptive transfer is not the only form of therapy that is available in accordance with the invention. CTLs can also be provoked in vivo, using a number of approaches. One approach, i.e., the use of non-proliferative cells expressing the complex, has been elaborated upon supra. The cells used in this approach may be those that normally express the complex, such as irradiated melanoma cells or cells transfected with one or both of the genes necessary for presentation of the complex. Chen et al., Proc. Natl. Acad. Sci. USA 88: 110–114 (Jan., 1991) exemplifies this approach, showing the use of transfected cells expressing HPVE7 peptides in a therapeutic regime. Various cell types may be used. Similarly, vectors carrying one or both of the genes of interest may be used. Viral or bacterial vectors are especially preferred. In these systems, the gene of interest is carried by, e.g., a Vaccinia virus or the bacteria BCG, and the materials de facto "infect" host cells. The cells which result present the complex of interest, and are recognized by autologous CTLs, which then proliferate. A similar effect can be achieved by combining the tumor rejection antigen or the precursor itself with an adjuvant to facilitate incorporation into HLA-A1 presenting cells which present the HLA molecule of interest. The TRAP is processed to yield the peptide partner of the HLA molecule while the TRA is presented without the need for further processing. Thus, one may treat disorders where a MAGE-3 derived TRA is presented by HLA-A1 molecules, or by any HLA molecule.

In a diagnostic context, one may determine a disorder, as the term is used herein, by assaying for expression of the TRAP. This can be done directly (via, e.g., a PCR assay for TRAP sequences), or indirectly, via assaying for a MAGE-3 derived TRA, as the TRA's presence means that the TRAP is or was expressed.

It will be noted that two nucleic acid molecules are presented herein, i.e., MAGE-3 and MAGE-31, each of which code for TRAP MAGE-3. It is to be understood that when the epxression "nucleic acid molecule which codes for MAGE-3 TRAP" is used, all molecules are covered which yield this molecule upon expression. Any number of variations, such as those showing codon degeneracy within the coding region, or variation within the introns, are covered by the invention.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. An isolated cDNA molecule consisting of a nucleotide sequence, which codes for tumor rejection antigen precursor MAGE-3, the complementary, sequence of which hybridizes, under stringent conditions to SEQ ID NO: 11 or SEQ ID NO: 12.

2. Isolated cDNA molecule wherein said molecule codes for tumor rejection antigen precursor MAGE-3 and consists of the nucleotide sequence set forth in SEQ ID NO: 11 or SEQ ID NO: 12.

3. Expression vector comprising the cDNA molecule of claim 1 operably linked to a promoter.

4. The expression vector of claim 3, further comprising a nucleic acid molecule which codes for HLA-A1.

5. Cell line transfected with the expression vector of claim 3.

6. The cell line of claim 5, wherein said cell line expresses HLA-A1.

7. The cell line of claim 5, wherein said cell line is further transfected with a nucleic acid molecule which codes for HLA-A1.

8. Isolated mRNA molecule complementary to the isolated cDNA molecule of claim 1.

9. Isolated mRNA molecule complementary to the isolated cDNA molecule of claim 2.

10. Isolated cDNA molecule which encodes tumor rejection antigen precursor protein MAGE-3, said protein having the amino acid sequence of the protein encoded by SEQ ID NO: 11 or SEQ ID NO: 12.

* * * * *